United States Patent
Rouviere et al.

(10) Patent No.: US 7,252,942 B2
(45) Date of Patent: Aug. 7, 2007

(54) PARALLEL CHROMOSOMAL STACKING OF TRAITS IN BACTERIA

(75) Inventors: Pierre E. Rouviere, Wilmington, DE (US); Wonchul Suh, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 453 days.

(21) Appl. No.: 10/734,778

(22) Filed: Dec. 12, 2003

(65) Prior Publication Data

US 2004/0209365 A1 Oct. 21, 2004

Related U.S. Application Data

(60) Provisional application No. 60/434,773, filed on Dec. 19, 2002.

(51) Int. Cl.
*C12Q 1/68* (2006.01)
(52) U.S. Cl. ............................ 435/6; 435/471; 435/472
(58) Field of Classification Search .................... None
See application file for complete search history.

(56) References Cited

U.S. PATENT DOCUMENTS 6,287,862 B1 9/2001 DelCardayre et al.

6,534,315 B1 3/2003 Bauer et al.

FOREIGN PATENT DOCUMENTS

WO WO 01/18222 3/2001
WO WO 03/089605 A2 10/2003

OTHER PUBLICATIONS

Datsenko, Kirill A. et al., One-step inactivation of chromosomal genes in *Escherichia coli* K-12 using PCR Products, Proceedings of the National Academy of Sciences of USA, 2000, pp. 6640-6645, vol. 97, No. 12., Washington, DC.
Zhou, Shengde et al., Production of Optically Pure D-Lactic Acid in Mineral Salts Medium by Metabolically Engineered *Escherichia coli* W3110, Applied Environmental Microbiology, Jan. 2003, pp. 399-407, vol. 69, No. 1, American Society for Microbiology.
Yuan, Luke Z. et al., Chromosomal promoter replacement of the isoprenoid pathway for enhancing carotenoid production of *E. coli*, Metabolic Engineering, Jan. 2006, pp. 79-90, vol. 8, Elsevier Inc.
Perdelchuk, M.Y. et al., Gene, vol. 187, pp. 231-238, 1997.

*Primary Examiner*—Nancy Vogel

(57) ABSTRACT

The invention describes a method for the stacking of traits in a recombination proficient host using a phage transduction system. The method makes use of a nucleic acid integration cassette that has homology to a specific site on a host chromosome for the insertion of genetic elements and the stacking of traits. Repetition of the method results in the stacking of traits on a single genetic element.

8 Claims, 9 Drawing Sheets

Figure 8
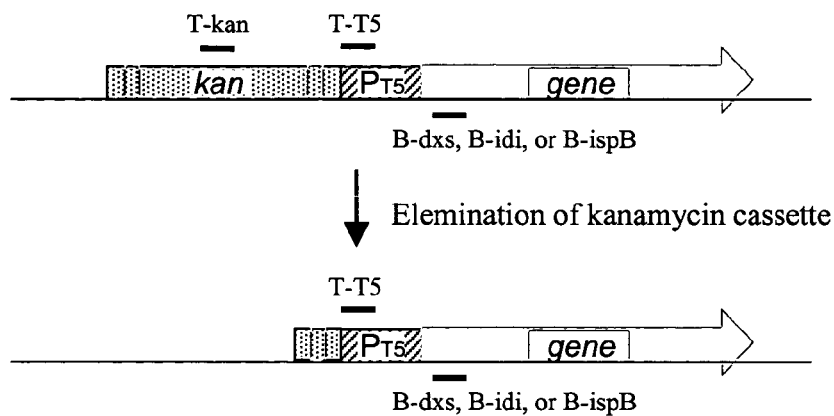
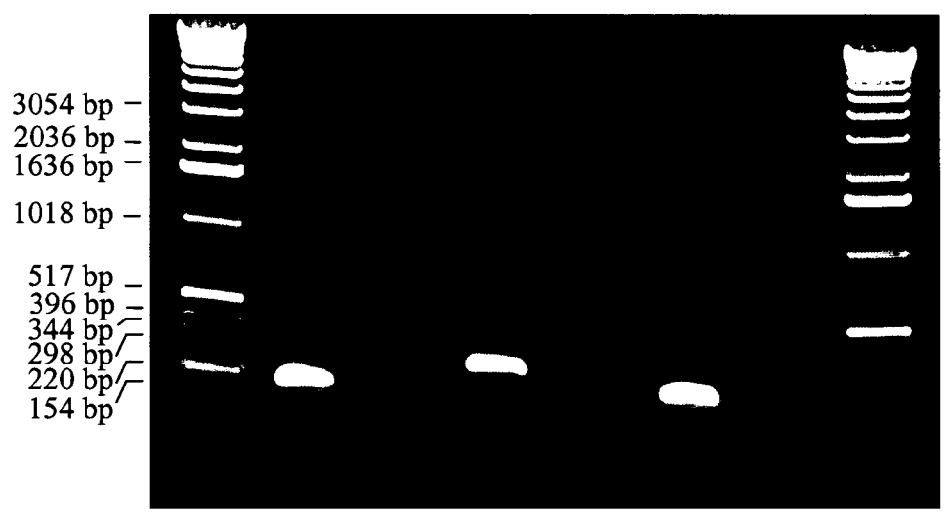

Control: *E. coli* pPCB15 containing carotenoid
biosynthsis gene cluster (*crtEXYIB*)

PARALLEL CHROMOSOMAL STACKING OF TRAITS IN BACTERIA

This application claims the benefit of U.S. Provisional Application No. 60/434,773 filed Dec. 19, 2002.

FIELD OF THE INVENTION

This invention is in the field of microbiology. More specifically, this invention pertains to methods associated with in vivo chromosomal engineering.

BACKGROUND OF THE INVENTION

The availability of complete bacterial genome sequences and the elucidation of metabolic pathways have resulted in the use of such knowledge to engineer microorganisms for the production of compounds of industrial interest. Microbial production of industrial compounds requires the ability to efficiently engineer changes to the genomes of the organisms. Engineering changes such as adding, removing, or modifying genetic elements have often proven to be challenging and time consuming exercises. One such modification is genetically engineering modulations to the expression of relevant genes in a metabolic pathway.

There are a variety of ways to modulate gene expression. Microbial metabolic engineering generally involves the use of multi-copy vectors to express a gene of interest under the control of a strong or conditional promoter. This method of metabolic engineering for industrial use has several drawbacks. It is sometimes difficult to maintain the vector due to segregational instability. Deleterious effects on cell viability and growth are often observed due to the vector burden. It is also difficult to control the optimal expression level of desired genes on a vector. To avoid the undesirable effects of using a multi-copy vector, a general approach using homologous recombination via a single insertion of bacteriophage λ, transposes, or other suitable vectors containing the gene of interest has been used. However, this method also has drawbacks such as the need for multiple cloning steps in order to get the gene of interest into a suitable vector prior to recombination. Another drawback is the instability associated with the inserted genes, which can be lost due to excision. Lastly, these methods have a limitation associated with multiple insertions and the inability to control the location of the insertion site on a chromosome.

Although previous methods have been developed for making multiple DNA modifications in the chromosome, these have used transposes that are randomly integrated and require multiple cloning steps to insert genes of interest (Perdelchuk, M. Y., and Bennett, G. N. 1997. *Gene.* 187: 231-238), or vectors that also require multiple cloning steps (PCT WO01/18222) and have not been applicable to all types of chromosomal modifications including insertions of whole genes or promoter sequences, deletions, and integrated transposes. Further, these methods have utilized a systematic approach to making multiple alterations at undefined loci as opposed to a combinatorial approach to making directed modifications on the chromosome.

The problem to be solved, therefore, is to define methods and materials to easily combine chromosomal modifications, created by any number of methods for chromosomal engineering, in one strain in a fashion that facilitates reaching optimum levels of product formation in bacteria, such as *E. coli*. The present invention has solved this problem by providing a method using P1 transduction and site-specific recombinase mediated marker excision to combine, in a linear, step-wise, and parallel combinatorial fashion chromosomal alterations. The present method allows for easy and efficient in vivo chromosomal engineering associated with biosynthetic pathway optimization.

SUMMARY OF THE INVENTION

The present method is a genetic tool useful for redesigning biosynthetic pathways, optimizing metabolic flux, and creating novel pathways by targeted in vivo chromosomal engineering. The method utilizes a homologous recombination system to introduce an integration cassette into a chromosome of a recombination proficient host cell and subsequently utilizes a phage transducing system to transfer the multiple integration cassettes into a single host cell in parallel combinatorial fashion. The "integration cassette" used to engineer the chromosomal modification includes a promoter and/or gene, and a selection marker flanked by site-specific recombinase sequences. After selection of the optimized transductants, a helper plasmid carrying a site-specific recombinase is introduced into the cells to excise the selectable markers bounded by site-specific recombinase sites. Repetition of the method facilitates combinatorial (multiple gene) trait stacking, necessary for biosynthetic pathway optimization.

The method can be used to engineer a variety of genetic elements, in addition to promoters, in the custom design of biosynthetic pathways. The approach is suitable for constructing industrially useful microbial strains, rather than just high expression of a specific single gene. In terms of metabolic balance, productivity, control, stability, and optimal expression of the genes of a particular pathway, the approach has many advantages and benefits when compared to metabolic engineering based on just a recombinant vector approach. The present method is illustrated using *E. coli* by example, but the method should prove to be useful in other bacterial strains as well.

The present method enables quick chromosomal trait stacking for optimal production of the desired genetic end product. A method that facilitates multiple chromosomal modifications is essential when engineering biosynthetic pathways for industrial purposes. The utility of the present method in engineering bacterial biosynthetic pathways is exemplified by altering isoprenoid and carotenoid biosynthesis. The promoters of the key genes encoding rate-limiting enzymes involved in the isoprenoid pathway (FIG. 1) were engineered via the novel method. The genetic modifications accomplished by the present invention resulted in increased β-carotene production.

Accordingly the invention provides a method for the optimization of the production of a genetic end product comprising:

a) providing a multiplicity of integration cassettes, each cassette comprising:
   (i) a nucleic acid integration fragment;
   (ii) a selectable marker bounded by specific recombinase sites responsive to a recombinase;
   (iii) homology arms having homology to different portions of a donor cell chromosome;

b) transforming at least one donor cell with the integration cassettes of (a) for its chromosomal integration;

c) infecting the transformed donor cell of (b) with a phage wherein the phage replicates and the donor cell is lysed;

d) isolating phage released by the lysis of the donor cell of (c);

e) mixing isolated phage released by the lysis the of donor cells of (c) carrying different integration cassettes of (a);

f) infecting a recipient cell with the mixture of the isolated phage of (e) wherein the integration cassettes each integrate into the recipient cell chromosome at the point of homology to the homology arms to generate a transduced recipient cell;

g) selecting transduced recipient cells on the basis of the selectable marker;

h) screening the recipient cell of (g) for the highest level of the genetic end product to identify a first overproducing strain;

i) activating a recombinase in the first overproducing strain of (h) which excises the selectable marker from the chromosomally integrated integration cassette;

j) infecting the first over producing strain of (i) with the mixture of the isolated phage of (e) wherein the integration cassettes each integrate into the recipient cell chromosome at the point of homology on the homology arms;

k) screening the infected first overproducing strain of (j) for the highest level of the genetic end product to identify a second overproducing strain; and l) comparing the levels of genetic end product produced by the first and second over producing strains whereby the production of the genetic end product is optimized.

In another embodiment the invention provides a method for the optimization of the production of a genetic end product comprising:

a) providing a multiplicity of integration cassettes, each cassette comprising:
  (i) a promoter;
  (ii) a selectable marker bounded by specific recombinase sites responsive to a recombinase;
  (iii) regions of homology to different portions of a P1 donor cell chromosome;

b) transforming at least one donor cell with the integration cassette of (a) for its chromosomal integration;

c) infecting the transformed donor cell of (b) with a P1 phage wherein the phage replicates and the donor cell is lysed;

d) isolating phage released by the lysis of the donor cell of (c);

e) mixing equal number of isolating phage released by the lysis of a set of donor cells of (c) carrying different integration cassettes of (a);

f) infecting a recipient cell with the mixture of the isolated phage of (e) wherein the integration cassettes each integrate into the recipient cell chromosome at the point of homology to the homology arms;

g) selecting transduced recipient cells on the basis of the selectable marker;

h) screening the recipient cell of (f) for the highest level of the genetic end product to identify a first overproducing strain;

i) activating a recombinase in the first over producing strain of (h) which excises the selectable marker from the chromosomally integrated integration cassette;

j) infecting the first over producing strain of (i) with the mixture of the isolated phage of (e) wherein the integration cassettes each integrate into the recipient cell chromosome at the point of homology on the homology arms;

k) screening the first over producing strain of (j) for the highest level of the genetic end product to identify a second overproducing strain; and l) comparing the levels of genetic end product produced by the first and second over producing strains whereby the production of the genetic end product is optimized.

BRIEF DESCRIPTION OF THE DRAWINGS SEQUENCE DESCRIPTIONS, AND BIOLOGICAL DEPOSITS

FIG. 8 illustrates elimination of the kanamycin resistance marker from the chromosome and an agarose gel verifying chromosomal integrations.

Figure 1:
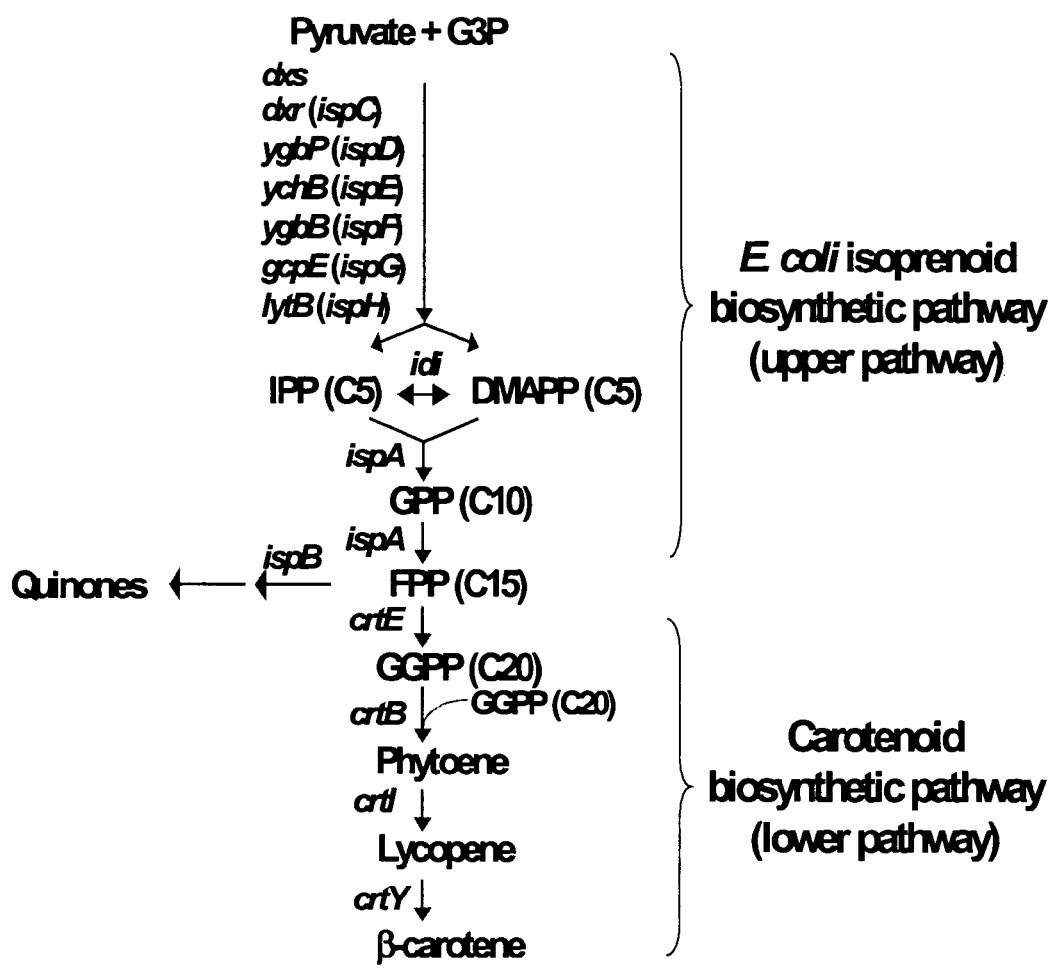
FIG. 1 illustrates the isoprenoid/carotenoid biosynthetic pathway.

The following biological deposit has been made under the terms of the Budapest Treaty on the International Recognition of the Deposit of Microorganisms for the purposes of Patent Procedure:

| Depositor Identification Reference | Int'l. Depository Designation | Date of Deposit |
| --- | --- | --- |
| Plasmid pCP20 | ATCC# PTA-4455 | Jun. 13, 2002 |

As used herein, "ATCC" refers to the American Type Culture Collection International Depository Authority located at ATCC, 10801 University Blvd., Manassas, Va. 20110-2209, USA. The "International Depository Designation" is the accession number to the culture on deposit with ATCC.

The listed deposits will be maintained in the indicated international depository for at least thirty (30) years and will be made available to the public upon the grant of a patent disclosing it. The availability of a deposit does not constitute a license to practice the subject invention in derogation of patent rights granted by government action.

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-12 are nucleic acid and amino acid sequences encoding genes from the *Pantoea stewartii* carotenoid gene cluster.

SEQ ID NOs:13-32 are oligonucleotide primers used to create integrative fragments.

SEQ ID NOs:33-34 are oligonucleotide primers designed to amplify the carotenoid gene cluster from *Pantoea stewartii*.

SEQ ID NOs:35-39 are oligonucleotide primers used for screening for the presence of chromosomally integrated fragments.

SEQ ID NO:40 is the nucleotide sequence for plasmid pPCB15

SEQ ID NO:41 is the nucleotide sequence for plasmid pKD46.

SEQ ID NO:42 is the nucleotide sequence for plasmid pSUH5.

SEQ ID NO:43 is the nucleotide sequence for the bacteriophage T5 promoter "$P_{T5}$".

The invention can be more fully understood from the following detailed description and the accompanying sequence descriptions, which form a part of this application.

DETAILED DESCRIPTION OF THE INVENTION

The invention provides a process to efficiently combine multiple chromosomal modifications into a microorganism in order to optimize the production of a desired genetic end product. The process begins with chromosomally engineering alterations to individual genes known to be associated with a biosynthetic pathway. This first step is exemplified by chromosomally engineering changes to genes in the isoprenoid biosynthetic pathway by replacing the native gene promoters with the strong phage T5 promoter ($P_{T5}$) using λ-Red mediated homologous recombination.

The λ-Red recombinase system facilitates efficient homologous recombination using linear DNA fragments having short regions (10-100 base pairs) of homology ("homology arms") to the targeted integration site. The integration fragment, termed "integration cassette", used to engineer the chromosomal modification includes a promoter and/or gene, and a selection marker flanked by site-specific recombinase sequences. Transformants are identified by incorporation of the selectable marker.

In a preferred embodiment, the bacteriophage P1 transduction system is used. Conventional P1 transduction can move only one genetic trait (i.e. gene) at a time from one host to another host. The present invention provides for a method moving multiple genetic traits into an E. coli host in a parallel combinatorial fashion using pooled mixtures of bacteriophage P1 in combination with a site-specific recombinase for removal of selection markers (FIG. 2).

Figure 2:
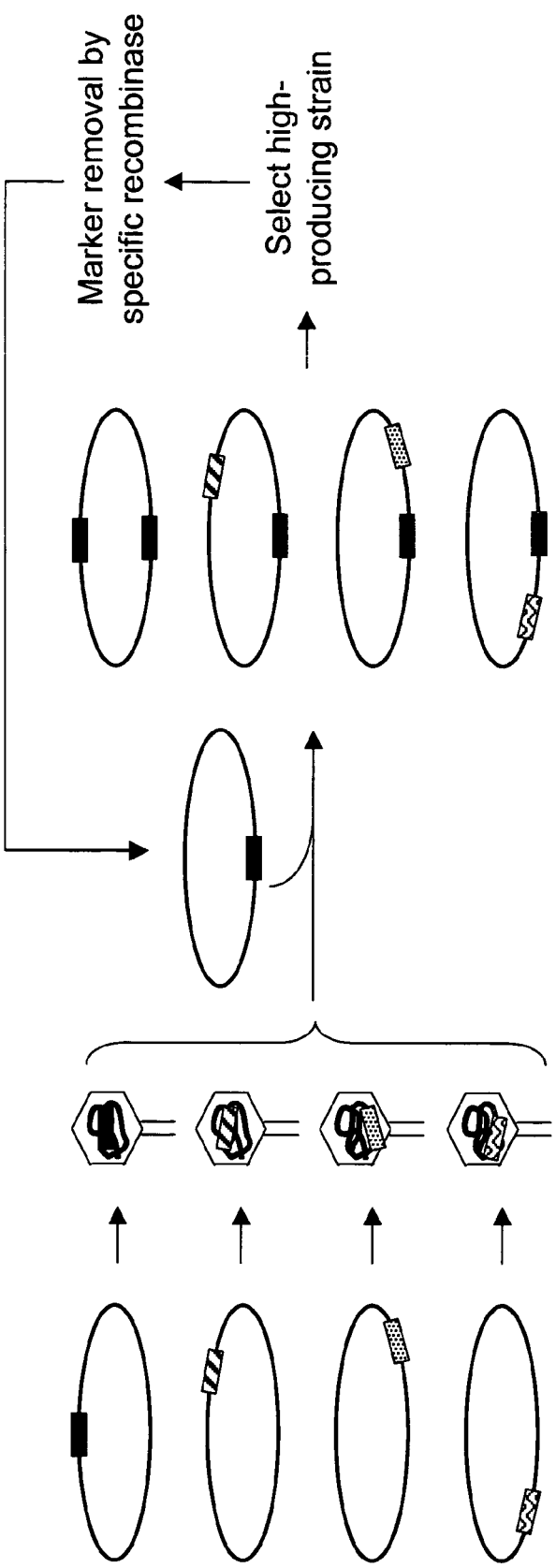
FIG. 2 illustrates method of the invention for in vivo chromosomal engineering of stacking traits in a parallel combinatorial fashion.

Referring to FIG. 2, the various transformants (donor cells) are infected with phage P1. The resultant P1 lysates made from the various individual transformants are mixed. The integration fragments are randomly packed into phage particles which are subsequently used to infect a recipient cell, usually of the same species as that of the donor cell. Transduction and homologous recombination occurs, creating colonies containing various chromosomal integrations of the previously modified promoter and/or gene. The transduced recipient cells are screened for antibiotic resistance and assayed for increased production of the desired genetic end product. After selection of the optimized transductants, the antibiotic resistance marker is removed by a site-specific recombinase. The selected transductants can be used again as a recipient cell in additional rounds of P1 transduction in order to engineer multiple chromosomal modifications, optimizing the production of the desired genetic end product.

In this disclosure, a number of terms and abbreviations are used. The following definitions are provided.

The term "genetic end product" means the substance, chemical or material that is produced as the result of the activity of a gene product. Typically a gene product is an enzyme and a genetic end product is the product of that enzymatic activity on a specific substrate. A genetic end product may be the result of a single enzyme activity or the result of a number of linked activities (i.e. an enzyme pathway).

The terms "stacking", "stacking traits", "parallel chromosomal stacking", and "trait stacking" are used interchangeably and refer to the repeated process of stacking multiple genetic traits into one E. Coli host in parallel using bacteriophage P1 mixtures in combination with the site-specific recombinase system for removal of the selection markers (FIG. 2).

The term "parallel combinatorial fashion" refers to the P1 transduction with the P1 lysate mixture made from various donor cells containing various genetic traits so that multiple genetic traits can be moved to the recipient cell in parallel.

The term "integration cassette" refers to a linear nucleic acid construct useful for the transformation of a recombination proficient bacterial host. Integration cassettes of the invention may include a variety of genetic elements such as selectable markers, expressible DNA fragments, and recombination regions having homology to regions on a bacterial chromosome or on other integration cassettes. Within the context of the present invention typically two integration cassettes are used for integration each with a single region of homology or "homology arm" to a portion if a bacterial chromosomal region.

The term "expressible DNA fragment" means any DNA that influences phenotypic changes in the host cell. An "expressible DNA fragment" may include for example, DNA comprising regulatory elements, isolated promoters, open reading frames, genes, or combinations thereof.

The terms "homology arm" and "recombination region" are used interchangeably and refer to a nucleotide sequence that enables homologous recombination between two nucleic acids having substantially the same nucleotide sequence in a particular region of two different nucleic acids. The preferred size range of the nucleotide sequence of the homology arm is from about 10 to about 100 nucleotides, where about 50 bp is preferred. Typically the level of base identity (defined herein as a one to one correspondence between the bases of each region) between the homology arm and the region of homology on the chromosome is at least about 70% where at least about 80% is preferred and where at least about 90% identity is most preferred.

The term "site-specific recombinase" is used in the present invention to describe a system comprised of one or more enzymes which recognize specific nucleotide sequences (recombination target sites) and which catalyze recombination between the recombination target sites. Site-specific recombination provides a method to rearrange, delete, or introduce exogenous DNA. Examples of site-specific recombinases and their associated recombination target sites include, but are not limited to Cre-lox, FLP/FRT, R/RS, Gin/gix, Xer/dif, Int/att, a pSR1 system, a cer system, and a fim system. The present invention illustrates the use of a site-specific recombinase to remove selectable markers. Antibiotic resistance markers, flanked on both sides by FRT recombination target sites, are removed by expression of the FLP site-specific recombinase.

The term "donor cell" refers to a bacterial strain susceptible to infection by a bacteriophage or virus, and which serves as a source for the nucleic acid fragments packaged into the transducing particles. Typically the genetic make up of the donor cell is similar or identical to the "recipient cell" which serves to receive lysate containing transducing phage or virus produced by the donor cell. As used herein, "P1 donor cell" is a bacterial strain susceptible to infection by a P1 bacteriophage.

The term "recipient cell" refers to a bacterial strain susceptible to infection by a bacteriophage or virus and which serves to receive lysate containing transducing phage or virus produced by the donor cell. A "P1 recipient cell" is a bacterial strain susceptible to infection by a P1 bacteriophage.

The term "selectable marker" means a gene encoding a gene product that, when present, enables one to identify and preferentially propagate a particular cell type.

The term "recombination proficient bacterial host" is used to describe a bacterial host which is capable of homologous recombination at rates useful for genetic engineering.

The term "homology" as applied to recombination regions and corresponding regions on a bacterial chromosome means nucleotide sequences sharing identical or nearly identical sequences. Complementary sequences between regions on the bacterial chromosome and recombination regions can associate and undergo homologous recombination in the presence of a recombinase system (i.e. λ-Red recombinase).

The terms "λ-Red recombination system", and "λ-Red system" are used interchangeably to describe a group of enzymes residing on a set of plasmids encoded by the bacteriophage λ genes exo, bet, and gam. The enzymes encoded by the three genes work together to increase the rate of homologous recombination in E. coli, an organism generally considered to have a relatively low rate of homologous recombination; especially when using linear integration cassettes. The λ-Red system facilitates the ability to use short regions of homology (10-50 bp) flanking linear dsDNA fragments for homologous recombination (Datsenko and Wanner, PNAS, 97:6640-6645 (2000)).

As used herein, the term "upstream" (when used in reference to a region of DNA) means the 5' side of a particular gene or sequence of nucleotides.

As used herein, the term "downstream" (when used in reference to a region of DNA) means the 3' side of a particular gene or sequence of nucleotides.

"Open reading frame" is abbreviated ORF.

"Polymerase chain reaction" is abbreviated PCR.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. The present invention illustrates the ability to genetically engineer replacement of a native gene's promoter with the phage T5 ("$P_{T5}$") strong promoter. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Operon", in bacterial DNA, is a cluster of contiguous genes transcribed from one promoter that gives rise to a polycistronic mRNA.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed only in response to different environmental or physiological conditions are commonly referred to as "inducible promoters". Promoters that cause a gene to be expressed in most cell types at most times are commonly referred to as "constitutive promoters". Promoters can also be categorized by the relative strength of their observed expression pattern (i.e. "weak", "moderate", "strong"). It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include sequences encoding regulatory signals capable of affecting mRNA processing or gene expression.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. Host organisms containing the transformed nucleic acid fragments are referred to as "transgenic", "recombinant" or "transformed" organisms.

The terms "transduction", "generalized transduction" and "P1 transduction" are used interchangeably and refer to a phenomenon in which bacterial DNA is transferred from one bacterial cell (the donor) to another (the recipient) by a phage particle containing bacterial DNA.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "isoprenoid" or "terpenoid" refers to the compounds and any molecules derived from the isoprenoid pathway including 10 carbon terpenoids and their derivatives, such as carotenoids and xanthophylls.

The term "Dxs" refers to the enzyme D-1-deoxyxylulose 5-phosphate encoded by the dxs gene that catalyzes the condensation of pyruvate and D-glyceraldehyde 3-phosphate to D-1-deoxyxylulose 5-phosphate (DOXP).

The terms "Dxr" or "IspC" refer to the enzyme DOXP reductoisomerase encoded by the dxr or ispC gene that catalyzes the simultaneous reduction and isomerization of DOXP to 2-C-methyl-D-erythritol-4-phosphate. The names of the gene, dxr or ispC, are used interchangeably in this application. The names of gene product, dxr or IspC are used interchangeably in this application.

The term "YgbP" or "IspD" and refers to the enzyme encoded by the ygbB or ispD gene that catalyzes the CTP-dependent cytidylation of 2-C-methyl-D-erythritol-4-phosphate to 4-diphosphocytidyl-2C-methyl-D-erythritol. The names of the gene, ygbP or ispD, are used interchangeably in this application. The names of gene product, YgbP or IspD are used interchangeably in this application.

The term "YchB" or "IspE" and refers to the enzyme encoded by the ychB or ispE gene that catalyzes the ATP-dependent phosphorylation of 4-diphosphocytidyl-2C-methyl-D-erythritol to 4-diphosphocytidyl-2C-methyl-D-erythritol-2-phosphate. The names of the gene, ychB or ispE, are used interchangeably in this application. The names of gene product, YchB or IspE are used interchangeably in this application.

The term "YgbB" or "IspF" refers to the enzyme encoded by the ybgB or ispF gene that catalyzes the cyclization with loss of CMP of 4-diphosphocytidyl-2C-methyl-D-erythritol to 4-diphosphocytidyl-2C-methyl-D-erythritol-2-phosphate to 2C-methyl-D-erythritol-2,4-cyclodiphosphate. The names of the gene, ygbB or ispF, are used interchangeably in this application. The names of gene product, YgbB or IspF are used interchangeably in this application.

The term "GcpE" or "IspG" refers to the enzyme encoded by the gcpE or ispG gene that is involved in conversion of 2C-methyl-D-erythritol-2,4-cyclodiphosphate to 1-hydroxy-2-methyl-2-(E)-butenyl 4-diphosphate. The names of the gene, gcpE or ispG, are used interchangeably in this application. The names of gene product, GcpE or IspG are used interchangeably in this application.

The term "LytB" or "IspH" refers to the enzyme encoded by the lytB or ispH gene and is involved in conversion of 1-hydroxy-2-methyl-2-(E)-butenyl 4-diphosphate to isopentenyl diphosphate (IPP) and dimethylallyl diphosphate (DMAPP). The names of the gene, lytB or ispH, are used interchangeably in this application. The names of gene product, LytB or IspH are used interchangeably in this application.

The term "idi" refers to the enzyme isopentenyl diphosphate isomerase encoded by the idi gene that converts isopentenyl diphosphate to dimethylallyl diphosphate.

The term "ispA" refers to the enzyme farnesyl pyrophosphate (FPP) synthase encoded by the ispA gene.

The term "ispB" refers to the enzyme octaprenyl diphosphate synthase, which supplies the precursor of the side chain of the isoprenoid quinones encoded by the ispB gene (FIG. 1).

Figure 6:
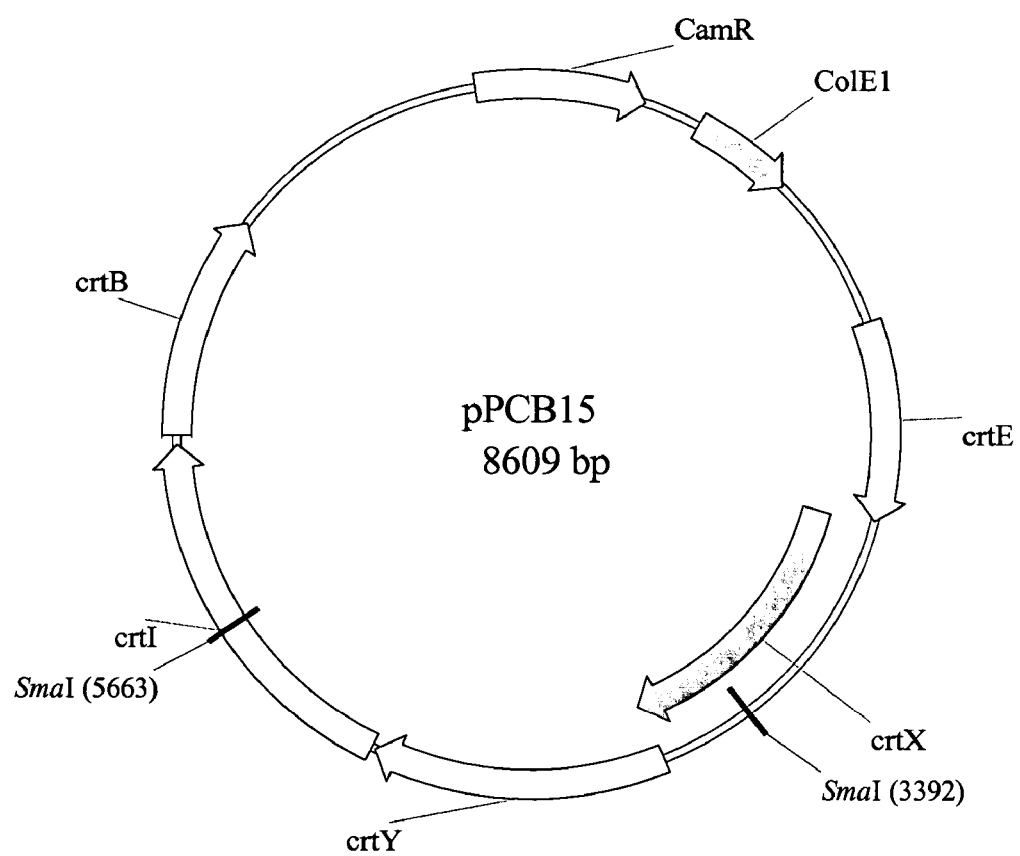
FIG. 6 illustrates the features of plasmid pPCB15.

The term "pPCB15" refers to the plasmid (FIG. 6; SEQ ID NO:40) containing β-carotene synthesis genes Pantoea crtEXYIB, using as a reporter plasmid for monitoring β-carotene production in E. coli that is genetically engineered via the invented method.

Figure 5:
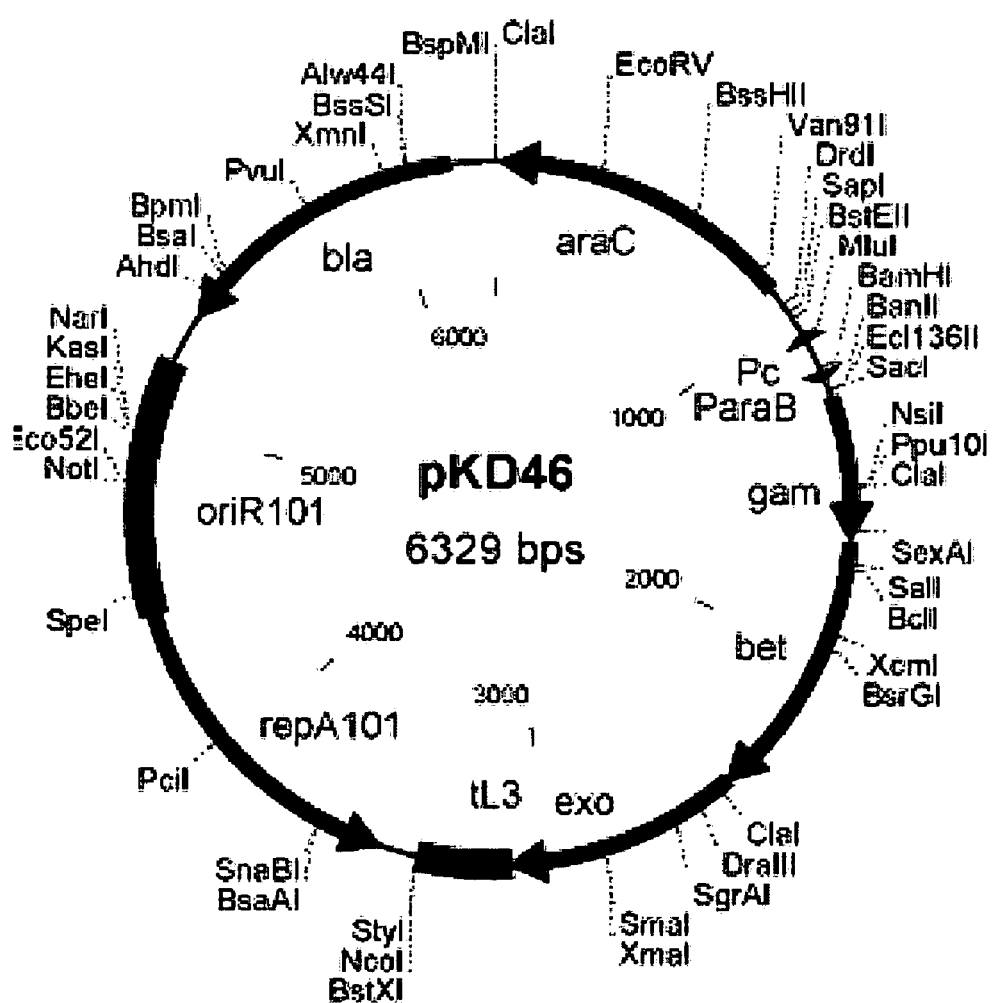
FIG. 5 illustrates the features of plasmid pKD46.

The term "pKD46" refers to the helper plasmid expressing the λ-Red recombinase system comprising three essential genes, exo, bet, and gam (FIG. 5; Datsenko and Wanner, supra; SEQ ID NO:41).

The term "pCP20" is a helper plasmid encoding the FLP site-specific recombinase (ATCC PTA-4455; Cherepanov and Wackernagel, Gene, 158:9-14 (1995); Datsenko and Wanner, supra).

Figure 4:
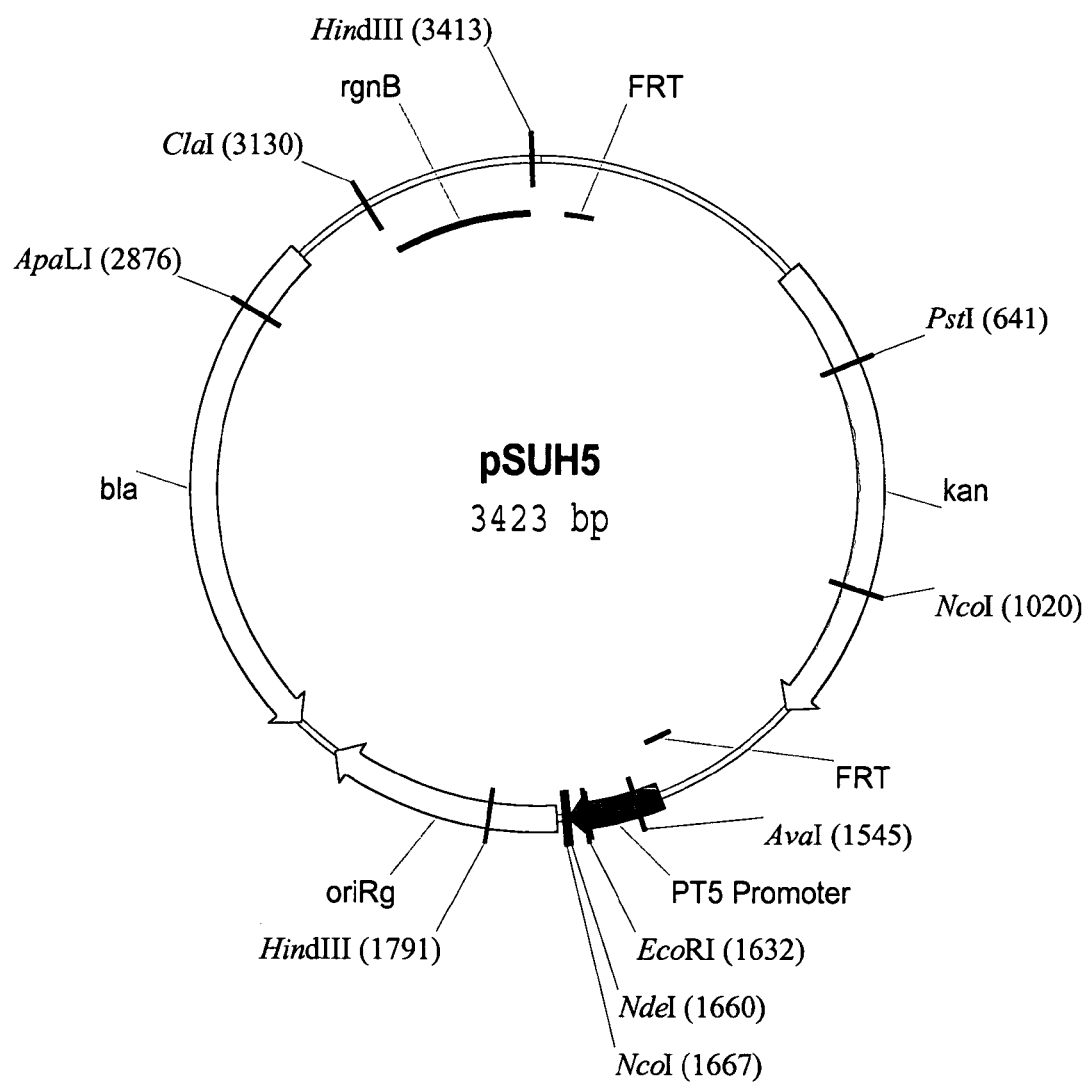
FIG. 4 illustrates the features of plasmid pSUH5.

The term "pSUH5" refers to the plasmid (FIG. 4; SEQ ID NO:42) that was constructed in this invention by cloning a phage T5 promoter ($P_{T5}$) region into the NdeI restriction endonuclease site of pKD4 (Datsenko and Wanner, supra). It was used as a template plasmid for PCR amplification of a fused kanamycin selectable marker/phage T5 promoter linear DNA nucleotide.

The terms "$P_{T5}$ promoter", "phage T5 promoter", and "$P_{T5}$" refer to the nucleotide sequence that comprises the −10 and −35 consensus sequences, lactose operator (lacO), and ribosomal binding site (rbs) from phage T5 (SEQ ID NO:43).

The term "helper plasmid" refers to either pKD46 encoding λ-Red recombinase or pCP20 (ATCC PTA-4455) encoding FLP site-specific recombinase (Cherepanov and Wackernagel, supra; Datsenko and Wanner, supra).

The term "E. coli" refers to Escherichia coli strain K-12 derivatives, such as MG1655 (ATCC 47076) and MC1061 (ATCC 53338).

The term "Pantoea stewartii subsp. stewartii" is abbreviated as "Pantoea stewartii" and is used interchangeably with Erwinia stewartii (Mergaert et al., Int J. Syst. Bacteriol., 43:162-173 (1993)).

The term "Pantoea ananatas" is used interchangeably with Erwinia uredovora (Mergaert et al., supra).

The term "Pantoea crtEXYIB cluster" refers to a gene cluster containing carotenoid synthesis genes crtEXYIB amplified from Pantoea stewartii ATCC 8199. The gene cluster contains the genes crtE, crtX, crtY, crtI, and crtB. The cluster also contains a crtZ gene organized in opposite direction and adjacent to crtB gene.

The term "CrtE" refers to geranylgeranyl pyrophosphate (GGPP) synthase enzyme encoded by crtE gene which converts trans-trans-farnesyl diphosphate+isopentenyl diphosphate to pyrophosphate+geranylgeranyl diphosphate.

The term "CrtY" refers to lycopene cyclase enzyme encoded by crtY gene which converts lycopene to β-carotene.

The term "CrtI" refers to phytoene dehydrogenase enzyme encoded by crtI gene which converts phytoene into lycopene via the intermediaries of phytofluene, zeta-carotene and neurosporene by the introduction of 4 double bonds The term "CrtB" refers to phytoene synthase enzyme encoded by crtB gene which catalyzes reaction from prephytoene diphosphate (geranylgeranyl pyrophosphate) to phytoene.

The term "CrtX" refers to zeaxanthin glucosyl transferase enzyme encoded by crtX gene which converts zeaxanthin to zeaxanthin-β-diglucoside.

The term "CrtZ" refers to the β-carotene hydroxylase enzyme encoded by crtZ gene which catalyses hydroxylation reaction from β-carotene to zeaxanthin.

The term "isoprenoid biosynthetic pathway" refers to those genes comprising members of the upper and/or lower isoprenoid pathways of the present invention as illustrated in FIG. 1. In the present invention, the terms "upper isoprenoid pathway" and "upper pathway" will be use interchangeably and will refer the enzymes involved in converting pyruvate and glyceraldehyde-3-phosphate to farnesyl pyrophosphate (FPP). These enzymes include, but are not limited to Dxs, Dxr (IspC), YgpP (IspD), YchB (IspE), YgbB (IspF), GcpE (IspG), LytB (IspH), Idi, lspA, and optionally IspB. In the present invention, the terms "lower isoprenoid pathway", "carotenoid biosynthetic pathway", and "lower pathway" will be used interchangeably and refer to those enzymes which convert FPP to carotenes, especially β-carotene (FIG. 1). The enzymes in this pathway include, but are not limited to CrtE, CrtY, Crtl, CrtB, CrtX, and CrtZ. In the present invention, the "lower pathway" genes are expressed on a reporter plasmid, pPCB15.

The terms "carotenoid biosynthetic enzyme" is an inclusive term referring to any and all of the enzymes encoded by the *Pantoea* crtEXYIB cluster. The enzymes include CrtE, CrtY, Crtl, CrtB, and CrtX.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res., [Proc. Int. Symp.]* (1994), Meeting Date 1992, 111-120. Editor(s): Suhai, Sandor. Publisher: Plenum, New York, N.Y. Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al. *Current Protocols in Molecular Biology*, published by Greene Publishing Assoc. and Wiley-Interscience (1987).

Integration Cassettes

Figure 3:
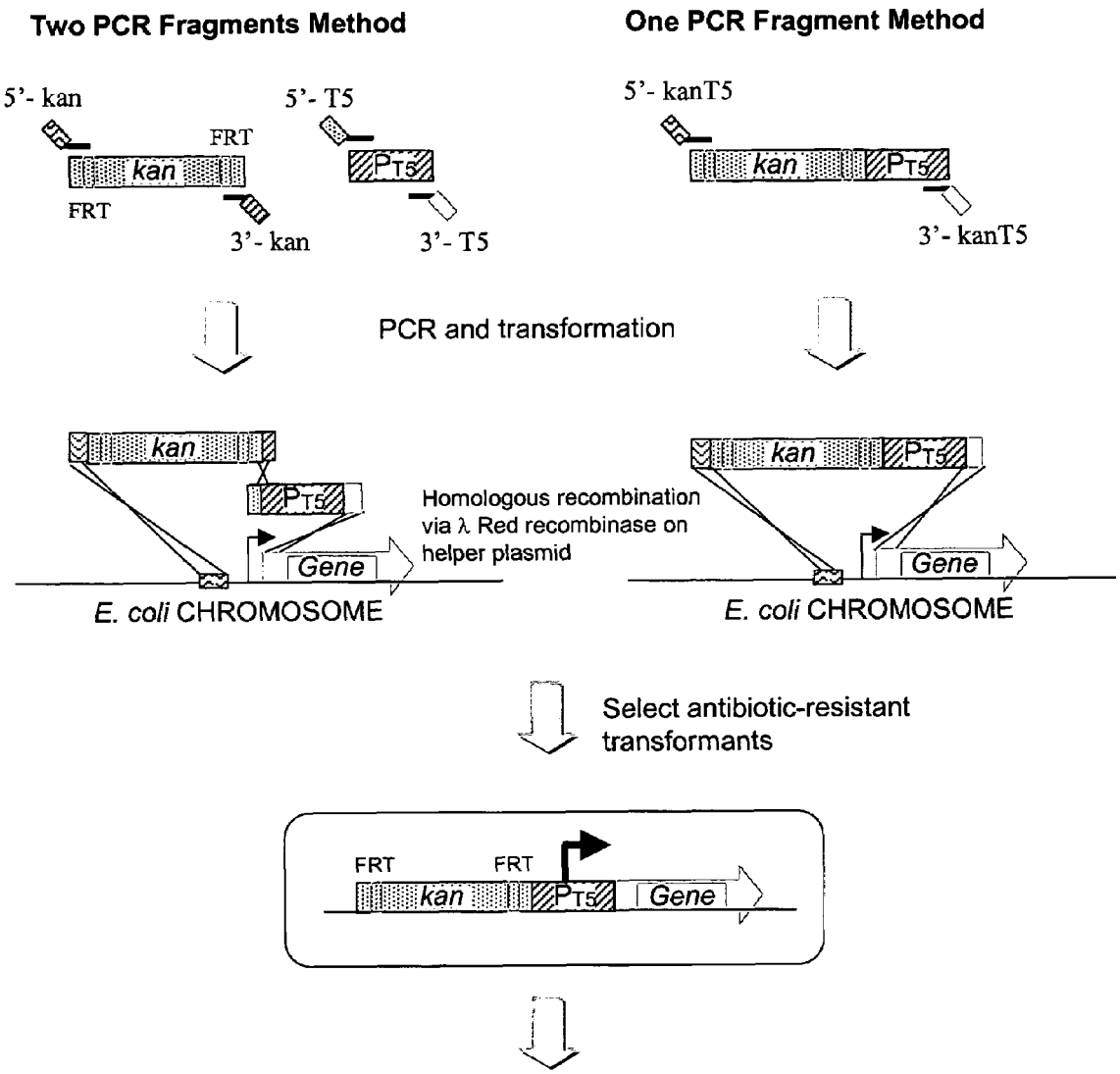
FIG. 3 illustrates the method of the invention for chromosomally integrating linear DNA using one or two PCR fragments.

As used in the present invention, "integration cassettes" are the linear double-stranded DNA fragments chromosomally integrated by homologous recombination via the use of two PCR-generated fragments or one PCR-generated fragment as seen in FIG. 3. The integration cassette comprises a nucleic acid integration fragment that contains a promoter and/or expressible DNA fragment and a selectable marker bounded by specific recombinase sites responsive to a site-specific recombinase and homology arms having homology to different portions of a donor cell chromosome. Typically, the integration cassette will have the general structure: 5'-RR1-RS-SM-RS-Y-RR2-3' wherein (i) RR1 is a first homology arm of about 10 to 100 bases;
(ii) RS is a recombination site responsive to a site-specific recombinase;
(iii) SM is a DNA fragment encoding a selectable marker;
(iv) Y is a first expressible DNA fragment; and
(v) RR2 is a second homology arm.

Expressible DNA fragments of the invention are those that will be useful in the genetic engineering of pathways. For example, it may be useful to engineer a strong promoter in place of a native promoter in certain pathways. Virtually any promoter is suitable for the present invention including, but not limited to lac, ara, tet, trp, $\lambda P_L$, $\lambda P_R$, T7, tac, $P_{T5}$, and trc (useful for expression in *Escherichia coli*) as well as the amy, apr, npr promoters and various phage promoters useful for expression in *Bacillus*, for example.

Typically the invention makes use of at least two integration cassettes, each having a single region of homology or homology arm to a portion of the chromosome. The use of two cassettes in this conformation is illustrated in FIG. 3 and will be referred to herein as the "two fragment method". The two fragment method provides high rates of integration and is useful for the elimination of additional cloning steps.

Alternatively, different coding regions may be introduced downstream of existing native promoters. In this manner new coding regions encoding members of a biosynthetic pathway may be introduced that add, remove, decrease, or enhance the desired activity of the targeted biosynthetic pathway. The biosynthetic pathway can either foreign or endogenous to the host cell. Preferably, one or more members of the biosynthetic pathway already exist in the host cell. These coding regions may be genes which retain their native promoters or may be chimeric genes operably linked to an inducible or constitutive strong promoter for increased expression of the genes in the targeted biosynthetic pathway. Preferred in the present invention are the genes of the isoprenoid and/or carotenoid biosynthetic pathway, which include dxs, dxr, ygbP, ychB, ygbB, idi, ispA, lytB, gcpE, ispB, gps, crtE, crtY, cryl, crtB, crtX, and crtZ, as defined above and illustrated in FIG. 1. In some situations the expressible DNA fragment may be in antisense orientation where it is desired to down-regulate certain elements of the pathway.

In the present invention it is preferred if the expressible DNA fragment is a promoter or a coding region useful for modulation of a biosynthetic pathway. Exemplified in the invention is the phage T5 promoter used for the modulation of the isoprenoid biosynthetic pathway in a recombination proficient *E. coli* host.

Generally, the preferred length of the homology arms is about 10 to about 100 base pairs in length, where about 50 bp is preferred. Given the relatively short lengths of the homology arms used in the present invention for homologous recombination, one would expect that the level of acceptable mismatched sequences should be kept to an absolute minimum for efficient recombination, preferably using sequences which are identical to those targeted for homologous recombination. From 20 to 40 base pairs of homology, the efficiency of homologous recombination increases by four orders of magnitude (Yu et al., *PNAS*, 97:5978-5983 (2000)). Therefore, multiple mismatching within homology arms may decrease the efficiency of homologous recombination; however, one skilled in the art can easily ascertain the acceptable level of mismatching.

The present invention makes use of a selectable marker on one of the two integration cassettes ("two fragment method"). Numerous selectable markers are known to those skilled in the art. The selectable marker is selected from the group consisting of antibiotic resistance markers, enzymatic markers (whereby the expressed marker catalyzes a chemical reaction creating a measurable difference in phenotypic appearance, for example, β-galactosidase), and amino acid biosynthesis enzymes which enable a normally auxotrophic bacteria to grow without the exogenously supplied amino acid. Examples of antibiotic resistance markers include ampicillin ($amp^r$), kanamycin ($kan^r$), and tetracycline ($tet^r$) resistance, to name a few. As used herein, the selectable markers are flanked by site-specific recombinase recognition sequences. After selection and construct verification, a site-specific recombinase is used to remove the selectable marker. The steps of the present method can then be repeated for additional in vivo chromosomal modifications. The integration cassette is bounded by site-specific recombinases for the eventual removal of the selectable marker. Site-specific recombinases, such as flippase (FLP) recombinase in the present invention, recognize specific recombination sequences (i.e. FRT sequences) and excise of the selectable marker. This aspect of the invention enables the repetitive use of the present method for multiple chromosomal modifications. The invention is not limited to the FLP-FRT recombinase system as several examples of site-specific recombinases and their associated specific recognition sequences are known in the art. Examples of other suitable site-specific recombinases and their corresponding recognition sequences include, but are not limited to Cre-lox, R/RS, Gin/gix, Xer/dif, Int/att, a pSR1 system, a cer system, and a fim system.

Recombination Proficient Host Cells

The present invention makes use of a recombination proficient host cell that is able to mediate efficient homologous recombination between the two integration cassettes and the host cell chromosome. Some organisms mediate homologous recombination very effectively (yeast for example) while others require genetic intervention. For example, *E. coli*, a host generally considered as one that does not undergo efficient transformation via homologous recombination naturally, may be altered to make it a recombination proficient host. Transformation with a helper plasmid containing the λ-Red recombinase system increases the rate of homologous recombination several orders of magnitude (Murphy et al., *Gene*, 246:321-330 (2000); Murphy, K., *J. Bacteriol.*, 180:2063-2071; Poteete and Fenton, *J. Bacteriol.*, 182:2336-2340 (2000); Poteete, A., *FEMS Microbiology Lett.*, 201:9-14 (2001); Datsenko and Wanner, supra; Yu et al., supra; Chaveroche et al., *Nucleic Acids Research*, 28:e97:1-6 (2000); U.S. Pat. No. 6,355,412; U.S. Pat. No. 6,509,156; and U.S. Ser. No. 60/434602). The λ-Red system can also be chromosomally integrated into the host. The λ-Red system contains three genes (exo, bet, and gam) which change the normally recombination deficient *E. coli* into a recombination proficient host.

Normally, *E. coli* efficiently degrade linear double-stranded (ds) DNA via its RecBCD endonuclease, resulting in transformation efficiencies not useful for chromosomal engineering. The gam gene encodes for a protein that binds to the *E. coli* RecBCD complex, inhibiting the undesirable endonuclease activity. The exo gene encodes for a λ-exonuclease that processively degrades the 5' end strand of double-stranded dsDNA and creates 3' single stranded overhangs. The protein encoded by bet complexes with the λ-exonuclease and binds to the single-stranded DNA overhangs and promotes renaturation of complementary strands and is capable of mediating exchange reactions. The λ-Red recombinase system enables the use of homologous recombination as a tool for in vivo chromosomal engineering in hosts normally considered difficult to transform by homologous recombination. The λ-Red system works in other bacteria as well (Poteete, A., supra, (2001)). The λ-Red system should be applicable to other hosts generally used for industrial production. These additional hosts include, but are not limited to *Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Paracoccus, Escherichia, Bacillus, Myxococcus, Salmonella, Yersinia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*.

λ-Red Recombinase System

The λ-Red recombinase system used in the present invention is contained on a helper plasmid (pKD46) and is comprised of three essential genes, exo, bet, and gam (Datsenko and Wanner, supra). The exo gene encodes an λ-exonuclease, which processively degrades the 5' end strand of double-stranded (ds) DNA and creates 3' single-stranded overhangs. Bet encodes for a protein which complexes with the λ-exonuclease and binds to the single stranded DNA and promotes renaturation of complementary strands and is capable of mediating exchange reactions. Gam encodes for a protein that binds to the *E. coli's* RecBCD complex and blocks the complex's endonuclease activity.

The λ-Red system is used in the present invention because homologous recombination in *E. coli* occurs at a very low frequency and usually requires extensive regions of homology. The λ-Red system facilitates the ability to use short regions of homology (10-50 bp) flanking linear dsDNA fragments for homologous recombination. Additionally, the RecBCD complex normally expressed in *E. coli* prevents the use of linear dsDNA for transformation as the complex's exonuclease activity efficiently degrades linear dsDNA. Inhibition of the RecBCD complex's endonuclease activity by gam is essential for efficient homologous recombination using linear dsDNA fragments.

Combinatorial P1 Transduction System

Transduction is a phenomenon in which bacterial DNA is transferred from one bacterial cell (the donor) to another (the recipient) by a phage particle containing bacterial DNA. When a population of donor bacteria is infected with a phage, the events of the phage lytic cycle may be initiated. During lytic infection, the enzymes responsible for packaging viral DNA into the bacteriophage sometimes package host DNA. The resulting particle is called a transducing particle. Upon lysis of the cell, these particles are released along with the normal virions. The lysate contains a mixture of normal virions and transducing particles. When the lysate is used to infect a population of recipient cells, most of the cells become infected with normal virus. However, a small proportion of the population receives transducing particles that inject the DNA they received from the previous host bacterium. This DNA can now undergo genetic recombination with the DNA of the recipient host. Conventional use of P1 transduction can move only one genetic trait (i.e. gene) at a time from one host to another.

It will be appreciated that a number of host systems may be used for purposes of the present invention including, but not limited to those with known transducing phages such as *Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Paracoccus, Escherichia, Bacillus, Myxococcus, Salmonella, Yersinia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. Examples of phages suitable for use in the present invention include P1, P2, lambda, ϕ80, ϕ3538, T1, T4, P22, P22 derivatives, ES18, Felix "o", P1-CmCs, Ffm, PY20, Mx4, Mx8, PBS-1, PMB-1, and PBT-1.

The present method provides a system for moving multiple genetic traits into an *E. coli* host in a parallel combinatorial fashion using the bacteriophage P1 lysate in combination with the site-specific recombinase system for removal of selection markers (FIG. 2). After transduction with the P1 lysate mixture made from various donor cells, the transduced recipient cells are screened for antibiotic resistance and assayed for increased production of the desired genetic end product (i.e. carotenoid production). After selection of the optimized transductants, the antibiotic resistance marker is removed by a site-specific recombinase. The selected transductants are used again as a recipient cell in additional rounds of P1 transduction in order to engineer multiple chromosomal modifications, optimizing production of the desired genetic end product. The present combinatorial P1 transduction method enables quick chromosomal trait stacking for optimal production of the desired genetic end product. The invention is very useful for continuous strain improvement toward a desired product.

Biosynthetic Pathway Optimization

The present method of combinatorial P1 transduction is applicable to the optimization of any biosynthetic pathway including isoprenoids, terpenoids, tetrapyrroles, polyketides, vitamins, amino acids, fatty acids, proteins, nucleic acids, carbohydrates, antimicrobial agents, anticancer agents and biological metabolites, to name a few.

The utility of the present invention is specifically illustrated by optimizing the isoprenoid and carotenoid biosynthetic pathways. Specifically, the method was used to identify the ispB gene by measuring its effects on the production of β-carotene. Carotenoid production (i.e. β-carotene) was enhanced by operably linking the phage T5 promoter to the coding sequence of the gene.

It will be appreciated that another pathway amenable to engineering by the present method is the heme biosynthetic pathway. One skilled in the art can prepare a series of strains where the promoters for each of the genes involved in the synthesis of tetrapyrroles, such as heme, are replaced by inducible promoters as described in this invention. Examples of the heme synthesis genes include for example: hemA, hemL, hemB, hemC, hemD, hemE, hemF, hemG, and hemH. The first step is chromosomally engineering changes to genes in the heme biosynthetic pathway by replacing the native gene promoters with a foreign promoter using λ-Red mediated homologous recombination. Next, combinatorial P1 transduction using P1 mixtures (FIG. 2) can be used to combinatorially stack the fused foreign promoter-heme genes for selecting a strain producing increased amounts of tetrapyrrole. One skilled in the art can select an appropriate promoter for use in the present method to optimize production of the desired genetic end product. The transductants are analyzed for production of heme and analyzed by traditional analytical methods, such as mass spectroscopy, UV-VIS spectrometry, bioassays or enzymatic coupled assays. A site-specific recombination system, such as the FLP/FRT or Cre-lox recombinase system, can be utilized to remove the markers from the strain after each stacking cycle. The process can be repeated, selecting those transductants for optimal production of the desired tetrapyrrole products.

Modulation of Genes Involved in Carotenoid Production.

The enzymatic pathway involved in the biosynthesis of carotenoids can be conveniently viewed in two parts, the upper isoprenoid pathway that facilitates the conversion of pyruvate and glyceraldehyde-3-phosphate to farnesyl pyrophosphate (FPP) and the lower carotenoid biosynthetic pathway, which provides for the synthesis of phytoene and all subsequently produced carotenoids (FIG. 1). The upper pathway is ubiquitous in many microorganisms. In these cases it will only be necessary to introduce genes that comprise the lower pathway for the biosynthesis of carotenoids. The key division between the two pathways concerns the synthesis of farnesyl pyrophosphate. Where FPP is naturally present, only elements of the lower carotenoid pathway will be needed. However, it will be appreciated that for the lower pathway carotenoid genes to be effective in the production of carotenoids, it will be necessary for the host cell to have suitable levels of FPP within the cell. Where the host cell does not provide a suitable level of FPP synthesis, it will be necessary to introduce chromosomal modifications (promoters, genes, etc.) necessary for the production of FPP. These modifications can be introduced in the host by using the present method. Each of these pathways will be discussed below in detail.

The Upper Isoprenoid Pathway

Isoprenoid biosynthesis occurs through either of two pathways, generating the common C5 isoprene subunit, isopentenyl pyrophosphate (IPP). First, isopentenyl pyrophosphate (IPP) may be synthesized through the well-known acetate/mevalonate pathway. However, recent studies have demonstrated that the mevalonate-dependent pathway does not operate in all living organisms. An alternate mevalonate-independent pathway for IPP biosynthesis has been characterized in bacteria and in green algae and higher plants (Horbach et al., *FEMS Microbiol. Lett.*, 111:135-140 (1993); Rohmer et al, *Biochem.*, 295: 517-524 (1993); Schwender et al., *Biochem.*, 316: 73-80 (1996); Eisenreich et al., *Proc. Natl. Acad. Sci. USA*, 93: 6431-6436 (1996)).

Many steps in the mevalonate-independent isoprenoid biosynthetic pathway are known (FIG. 1). For example, the initial steps of the alternate pathway leading to the production of IPP have been studied in *Mycobacterium tuberculosis* by Cole et al. (*Nature*, 393:537-544 (1998)). The first step of the pathway involves the condensation of two 3-carbon molecules (pyruvate and D-glyceraldehyde 3-phosphate) to yield a 5-carbon compound known as D-1-deoxyxylulose-5-phosphate. This reaction occurs by the DXS enzyme, encoded by the dxs gene. Next, the isomerization and reduction of D-1-deoxyxylulose-5-phosphate yields 2-C-methyl-D-erythritol-4-phosphate. One of the enzymes involved in the isomerization and reduction process is D-1-deoxyxylulose-5-phosphate reductoisomerase (DXR), encoded by the gene dxr (ispC). 2-C-methyl-D-erythritol-4-phosphate is subsequently converted into 4-diphosphocytidyl-2C-methyl-D-erythritol in a CTP-dependent reaction by the enzyme encoded by the non-annotated gene ygbP. The ygbP gene was recently renamed as ispD as a part of the isp gene cluster (SwissProtein Accession #Q46893).

Next, the $2^{nd}$ position hydroxy group of 4-diphosphocytidyl-2C-methyl-D-erythritol can be phosphorylated in an ATP-dependent reaction by the enzyme encoded by the ychB gene, recently renamed ispE (SwissProtein Accession #P24209). This product phosphorylates 4-diphosphocytidyl-2C-methyl-D-erythritol, resulting in 4-diphosphocytidyl-2C-methyl-D-erythritol 2-phosphate. The product of the ygbB gene converts 4-diphosphocytidyl-2C-methyl-D-erythritol 2-phosphate to 2C-methyl-D-erythritol 2,4-cyclodiphosphate in a CTP-dependent manner.

This gene has also been recently renamed as isp (SwissProtein Accession #P36663).

The enzymes encoded by the gcpE (ispG) and lytB (ispH) genes (and perhaps others) are thought to participate in the reactions leading to formation of isopentenyl pyrophosphate (IPP) and dimethylallyl pyrophosphate (DMAPP). IPP may be isomerized to DMAPP via IPP isomerase, encoded by the idi gene. However, this enzyme is not essential for survival and may be absent in some bacteria using 2-C-methyl-D-erythritol 4-phosphate (MEP) pathway. Recent evidence suggests that the MEP pathway branches before IPP and separately produces IPP and DMAPP via the lytB (ispH) gene product. A lytB (ispH) knockout mutation is lethal in *E. coli* except in media supplemented with both IPP and DMAPP.

The synthesis of FPP occurs via isomerization of IPP to dimethylallyl pyrophosphate (DMAPP). This reaction is followed by a sequence of two prenyltransferase reactions catalyzed by ispA, leading to the creation of geranyl pyrophosphate (GPP; a 10-carbon molecule) and farnesyl pyrophosphate (FPP; 15-carbon molecule).

Genes encoding elements of the upper pathway are known from a variety of plant, animal, and bacterial sources, as shown in Table 1.

TABLE 1

Sources of Genes Encoding the Upper Isoprene Pathway

| Gene | GenBank Accession Number and Source Organism |
|---|---|
| dxs (D-1-deoxyxylulose 5-phosphate synthase) | AF035440, *Escherichia coli*<br>Y18874, *Synechococcus* PCC6301<br>AB026631, *Streptomyces* sp. CL190<br>AB042821, *Streptomyces griseolosporeus*<br>AF111814, *Plasmodium falciparum*<br>AF143812, *Lycopersicon esculentum*<br>AJ279019, *Narcissus pseudonarcissus*<br>AJ291721, *Nicotiana tabacum* |
| dxr (ispC) (1-deoxy-D-xylulose 5-phosphate reductoisomerase) | AB013300, *Escherichia coli*<br>AB049187, *Streptomyces griseolosporeus*<br>AF111813, *Plasmodium falciparum*<br>AF116825, *Mentha x piperita*<br>AF148852, *Arabidopsis thaliana*<br>AF182287, *Artemisia annua*<br>AF250235, *Catharanthus roseus*<br>AF282879, *Pseudomonas aeruginosa*<br>AJ242588, *Arabidopsis thaliana* |

TABLE 1-continued

Sources of Genes Encoding the Upper Isoprene Pathway

| Gene | GenBank Accession Number and Source Organism |
|---|---|
| | AJ250714, *Zymomonas mobilis* strain ZM4<br>AJ292312, *Klebsiella pneumoniae*,<br>AJ297566, *Zea mays* |
| ygbP (ispD) (2-C-methyl-D-erythritol 4-phosphate cytidylyltransferase) | AB037876, *Arabidopsis thaliana*<br>AF109075, *Clostridium difficile*<br>AF230736, *Escherichia coli*<br>AF230737, *Arabidopsis thaliana* |
| ychB (ispE) (4-diphosphocytidyl-2-C-methyl-D-erythritol kinase) | AF216300, *Escherichia coli*<br>AF263101, *Lycopersicon esculentum*<br>AF288615, *Arabidopsis thaliana* |
| ygbB (ispF) (2-C-methyl-D-erythritol 2,4-cyclodiphosphate synthase) | AB038256, *Escherichia coli* mecs gene<br>AF230738, *Escherichia coli*<br>AF250236, *Catharanthus roseus* (MECS)<br>AF279661, *Plasmodium falciparum*<br>AF321531, *Arabidopsis thaliana* |
| gcpE (ispG) (1-hydroxy-2-methyl-2-(E)-butenyl 4-diphosphate synthase) | O67496, *Aquifex aeolicus*<br>P54482, *Bacillus subtilis*<br>Q9pky3, *Chlamydia muridarum*<br>Q9Z8H0, *Chlamydophila pneumoniae*<br>O84060, *Chlamydia trachomatis*<br>P27433, *Escherichia coli*<br>P44667, *Haemophilus influenzae*<br>Q9ZLL0, *Helicobacter pylori* J99<br>O33350, *Mycobacterium tuberculosis*<br>S77159, *Synechocystis* sp.<br>Q9WZZ3, *Thermotoga maritima*<br>O83460, *Treponema pallidum*<br>Q9JZ40, *Neisseria meningitidis*<br>Q9PPM1, *Campylobacter jejuni*<br>Q9RXC9, *Deinococcus radiodurans*<br>AAG07190, *Pseudomonas aeruginosa*<br>Q9KTX1, *Vibrio cholerae* |
| lytB (ispH) | AF027189, *Acinetobacter* sp. BD413<br>AF098521, *Burkholderia pseudomallei*<br>AF291696, *Streptococcus pneumoniae*<br>AF323927, *Plasmodium falciparum* gene<br>M87645, *Bacillus subtillis*<br>U38915, *Synechocystis* sp.<br>X89371, *C. jejunisp* O67496 |
| IspA (FPP synthase) | AB003187, *Micrococcus luteus*<br>AB016094, *Synechococcus elongatus*<br>AB021747, *Oryza sativa* FPPS1 gene for farnesyl diphosphate synthase<br>AB028044, *Rhodobacter sphaeroides*<br>AB028046, *Rhodobacter capsulatus*<br>AB028047, *Rhodovulum sulfidophilum*<br>AF112881 and AF136602, *Artemisia annua*<br>AF384040, *Mentha x piperita*<br>D00694, *Escherichia coli*<br>D13293, *B. stearothermophilus*<br>D85317, *Oryza sativa*<br>X75789, *A. thaliana*<br>Y12072, *G. arboreum*<br>Z49786, *H. brasiliensis*<br>U80605, *Arabidopsis thaliana* farnesyl diphosphate synthase precursor (FPS1) mRNA, complete cds<br>X76026, *K. lactis* FPS gene for farnesyl diphosphate synthetase, QCR8 gene for bc1 complex, subunit VIII<br>X82542, *P. argentatum* mRNA for farnesyl diphosphate synthase (FPS1)<br>X82543, *P. argentatum* mRNA for farnesyl diphosphate synthase (FPS2)<br>BC010004, *Homo sapiens*, farnesyl diphosphate synthase (farnesyl pyrophosphate synthetase, dimethylallyltranstransferase, geranyltranstransferase), clone MGC 15352 IMAGE, 4132071, mRNA, complete cds<br>AF234168, *Dictyostelium discoideum* farnesyl diphosphate synthase (Dfps) |

TABLE 1-continued

Sources of Genes Encoding the Upper Isoprene Pathway

| Gene | GenBank Accession Number and Source Organism |
|---|---|
| | L46349, *Arabidopsis thaliana* farnesyl diphosphate synthase (FPS2) mRNA, complete cds |
| | L46350, *Arabidopsis thaliana* farnesyl diphosphate synthase (FPS2) gene, complete cds |
| | L46367, *Arabidopsis thaliana* farnesyl diphosphate synthase (FPS1) gene, alternative products, complete cds |
| | M89945, Rat farnesyl diphosphate synthase gene, exons 1–8 |
| | NM_002004, *Homo sapiens* farnesyl diphosphate synthase (farnesyl pyrophosphate synthetase, dimethylallyltranstransferase, geranyltranstransferase) (FDPS), mRNA |
| | U36376, *Artemisia annua* farnesyl diphosphate synthase (fps1) mRNA, complete cds |
| | XM_001352, *Homo sapiens* farnesyl diphosphate synthase (farnesyl pyrophosphate synthetase, dimethylallyltranstransferase, geranyltranstransferase) (FDPS), mRNA |
| | XM_034497, *Homo sapiens* farnesyl diphosphate synthase (farnesyl pyrophosphate synthetase, dimethylallyltranstransferase, geranyltranstransferase) (FDPS), mRNA |
| | XM_034498, *Homo sapiens* farnesyl diphosphate synthase (farnesyl pyrophosphate synthetase, dimethylallyltranstransferase, geranyltranstransferase) (FDPS), mRNA |
| | XM_034499, *Homo sapiens* farnesyl diphosphate synthase (farnesyl pyrophosphate synthetase, dimethylallyltranstransferase, geranyltranstransferase) (FDPS), mRNA |
| | XM_0345002, *Homo sapiens* farnesyl diphosphate synthase (farnesyl pyrophosphate synthetase, dimethylallyltranstransferase, geranyltranstransferase) (FDPS), mRNA |

The Lower Carotenoid Biosynthetic Pathway

The division between the upper isoprenoid pathway and the lower carotenoid pathway is somewhat subjective. Because FPP synthesis is common in both carotenogenic and non-carotenogenic bacteria, the first step in the lower carotenoid biosynthetic pathway is considered to begin with the prenyltransferase reaction converting farnesyl pyrophosphate (FPP) to geranylgeranyl pyrophosphate (GGPP). The gene crtE, encoding GGPP synthetase is responsible for this prenyltransferase reaction which adds IPP to FPP to produce the 20-carbon molecule GGPP. A condensation reaction of two molecules of GGPP occurs to form phytoene (PPPP), the first 40-carbon molecule of the lower carotenoid biosynthesis pathway. This enzymatic reaction is catalyzed by crtB, encoding phytoene synthase.

Lycopene, which imparts a "red"-colored spectra, is produced from phytoene through four sequential dehydrogenation reactions by the removal of eight atoms of hydrogen, catalyzed by the gene crtI (encoding phytoene desaturase). Intermediaries in this reaction are phytofluene, zeta-carotene, and neurosporene.

Lycopene cyclase (crtY) converts lycopene to β-carotene. β-carotene is converted to zeaxanthin via a hydroxylation reaction resulting from the activity of β-carotene hydroxylase (encoded by the crtZ gene). β-cryptoxanthin is an intermediate in this reaction.

β-carotene is converted to canthaxanthin by β-carotene ketolase encoded by a crtW or crtO gene. Echinenone in an intermediate in this reaction. Canthaxanthin can then be converted to astaxanthin by β-carotene hydroxylase encoded by a crtZ or crtR gene. Adonbirubrin is an intermediate in this reaction.

Zeaxanthin can be converted to zeaxanthin-β-diglucoside. This reaction is catalyzed by zeaxanthin glucosyl transferase (crtX).

Zeaxanthin can be converted to astaxanthin by β-carotene ketolase encoded by ketolase encoded by crtW, crtO or bkt. The BKT/CrtW enzymes synthesized canthaxanthin via echinenone from β-carotene and 4-ketozeaxanthin. Adonixanthin is an intermediate in this reaction.

Spheroidene can be converted to spheroidenone by spheroidene monooxygenase encoded by crtA.

Neurosporene can be converted spheroidene and lycopene can be converted to spirilloxanthin by the sequential actions of hydroxyneurosporene synthase, methoxyneurosporene desaturase and hydroxyneurosporene-O-methyltransferase encoded by the crtC, crtD and crtF genes, respectively.

β-carotene can be converted to isorenieratene by β-carotene desaturase encoded by crtU.

Genes encoding elements of the lower carotenoid biosynthetic pathway are known from a variety of plant, animal, and bacterial sources, as shown in Table 2.

TABLE 2

Sources of Genes Encoding the Lower Carotenoid Biosynthetic Pathway

| Gene | GenBank Accession Number and Source Organism |
|---|---|
| crtE (GGPP Synthase) | AB000835, *Arabidopsis thaliana* |
| | AB016043 and AB019036, *Homo sapiens* |
| | AB016044, *Mus musculus* |
| | AB027705 and AB027706, *Daucus carota* |
| | AB034249, *Croton sublyratus* |
| | AB034250, *Scoparia dulcis* |
| | AF020041, *Helianthus annuus* |
| | AF049658, *Drosophila melanogaster* signal recognition particle 19 kDa protein (srp 19) gene, partial sequence; and geranylgeranyl pyrophosphate synthase (quemao) gene, complete cds |
| | AF049659, *Drosophila melanogaster* geranylgeranyl pyrophosphate synthase mRNA, complete cds |
| | AF139916, *Brevibacterium linens* |
| | AF279807, *Penicillium paxilli* geranylgeranyl pyrophosphate synthase (ggs1) gene, complete |
| | AF279808, *Penicillium paxilli* dimethylallyl tryptophan synthase (paxD) gene, partial cds; and cytochrome P450 monooxygenase (paxQ), cytochrome P450 monooxygenase (paxP), PaxC (paxC), monooxygenase (paxM), geranylgeranyl pyrophosphate synthase (paxG), PaxU (paxU), and metabolite transporter (paxT) genes, complete cds |
| | AJ010302, *Rhodobacter sphaeroides* |
| | AJ133724, *Mycobacterium aurum* |
| | AJ276129, *Mucor circinelloides* f. lusitanicus carG gene for geranylgeranyl pyrophosphate synthase, exons 1–6 |
| | D85029, *Arabidopsis thaliana* mRNA for geranylgeranyl pyrophosphate synthase, partial cds |
| | L25813, *Arabidopsis thaliana* |
| | L37405, *Streptomyces griseus* geranylgeranyl |

TABLE 2-continued

Sources of Genes Encoding the Lower Carotenoid Biosynthetic Pathway

| Gene | GenBank Accession Number and Source Organism |
|---|---|
| | pyrophosphate synthase (crtB), phytoene desaturase (crtE) and phytoene synthase (crtI) genes, complete cds |
| | U15778, *Lupinus albus* geranylgeranyl pyrophosphate synthase (ggps1) mRNA, complete cds |
| | U44876, *Arabidopsis thaliana* pregeranylgeranyl pyrophosphate synthase (GGPS2) mRNA, complete cds |
| | X92893, *C. roseus* |
| | X95596, *S. griseus* |
| | X98795, *S. alba* |
| | Y15112, *Paracoccus marcusii* |
| crtX (Zeaxanthin glucosylase) | D90087, *E. uredovora* |
| crtY (Lycopene-β-cyclase) | M87280 and M90698, *Pantoea agglomerans* |
| | AF139916, *Brevibacterium linens* |
| | AF152246, *Citrus x paradisi* |
| | AF218415, *Bradyrhizobium* sp. ORS278 |
| | AF272737, *Streptomyces griseus* strain IFO13350 |
| | AJ133724, *Mycobacterium aurum* |
| | AJ250827, *Rhizomucor circinelloides f. lusitanicus* carRP gene for lycopene cyclase/phytoene synthase, exons 1–2 |
| | AJ276965, *Phycomyces blakesleeanus* carRA gene for phytoene synthase/lycopene cyclase, exons 1–2 |
| | D58420, *Agrobacterium aurantiacum* |
| | D83513, *Erythrobacter longus* |
| | L40176, *Arabidopsis thaliana* lycopene cyclase (LYC) mRNA, complete cds |
| | M87280, *Pantoea agglomerans* |
| | U50738, *Arabodopsis thaliana* lycopene epsilon cyclase mRNA, complete cds |
| | U50739, *Arabidosis thaliana* lycopene β cyclase mRNA, complete cds |
| | U62808, *Flavobacterium* ATCC21588 |
| | X74599, *Synechococcus* sp. Icy gene for lycopene cyclase |
| | X81787, *N. tabacum* CrtL-1 gene encoding lycopene cyclase |
| | X86221, *C. annuum* |
| | X86452, *L. esculentum* mRNA for lycopene β-cyclase |
| | X95596, *S. griseus* |
| | X98796, *N. pseudonarcissus* |
| crtI (Phytoene desaturase) | AB046992, *Citrus unshiu* CitPDS1 mRNA for phytoene desaturase, complete cds |
| | AF039585, *Zea mays* phytoene desaturase (pds1) gene promoter region and exon 1 |
| | AF049356, *Oryza sativa* phytoene desaturase precursor (Pds) mRNA, complete cds |
| | AF139916, *Brevibacterium linens* |
| | AF218415, *Bradyrhizobium* sp. ORS278 |
| | AF251014, *Tagetes erecta* |
| | AF364515, *Citrus x paradisi* |
| | D58420, *Agrobacterium aurantiacum* |
| | D83514, *Erythrobacter longus* |
| | L16237, *Arabidopsis thaliana* |
| | L37405, *Streptomyces griseus* geranylgeranyl pyrophosphate synthase (crtB), phytoene desaturase (crtE) and phytoene synthase (crtI) genes, complete cds |
| | L39266, *Zea mays* phytoene desaturase (Pds) mRNA, complete cds |
| | M64704, Soybean phytoene desaturase |
| | M88683, *Lycopersicon esculentum* phytoene desaturase (pds) mRNA, complete cds |
| | S71770, carotenoid gene cluster |
| | U37285, *Zea mays* |
| | U46919, *Solanum lycopersicum* phytoene desaturase (Pds) gene, partial cds |
| | U62808, *Flavobacterium* ATCC21588 |
| | X55289, *Synechococcus* pds gene for phytoene desaturase |
| | X59948, *L. esculentum* |
| | X62574, *Synechocystis* sp. pds gene for phytoene desaturase |
| | X68058, *C. annuum* pds1 mRNA for phytoene desaturase |
| | X71023, *Lycopersicon esculentum* pds gene for phytoene desaturase |
| | X78271, *L. esculentum* (Ailsa Craig) PDS gene |
| | X78434, *P. blakesleeanus* (NRRL1555) carB gene |
| | X78815, *N. pseudonarcissus* |
| | X86783, *H. pluvialis* |
| | Y14807, *Dunaliella bardawil* |
| | Y15007, *Xanthophyllomyces dendrorhous* |
| | Y15112, *Paracoccus marcusii* |
| | Y15114, *Anabaena* PCC7210 crtP gene |
| | Z11165, *R. capsulatus* |
| crtB (Phytoene synthase) | AB001284, *Spirulina platensis* |
| | AB032797, *Daucus carota* PSY mRNA for phytoene synthase, complete cds |
| | AB034704, *Rubrivivax gelatinosus* |
| | AB037975, *Citrus unshiu* |
| | AF009954, *Arabidopsis thaliana* phytoene synthase (PSY) gene, complete cds |
| | AF139916, *Brevibacterium linens* |
| | AF152892, *Citrus x paradisi* |
| | AF218415, *Bradyrhizobium* sp. ORS278 |
| | AF220218, *Citrus unshiu* phytoene synthase (Psy1) mRNA, complete cds |
| | AJ010302, Rhodobacter |
| | AJ133724, *Mycobacterium aurum* |
| | AJ278287, *Phycomyces blakesleeanus* carRA gene for lycopene cyclase/phytoene synthase, |
| | AJ304825, *Helianthus annuus* mRNA for phytoene synthase (psy gene) |
| | AJ308385, *Helianthus annuus* mRNA for phytoene synthase (psy gene) |
| | D58420, *Agrobacterium aurantiacum* |
| | L23424, *Lycopersicon esculentum* phytoene synthase (PSY2) mRNA, complete cds |
| | L25812, *Arabidopsis thaliana* |
| | L37405, *Streptomyces griseus* geranylgeranyl pyrophosphate synthase (crtB), phytoene desaturase (crtE) and phytoene synthase (crtI) genes, complete cds |
| | M38424, *Pantoea agglomerans* phytoene synthase (crtE) gene, complete cds |
| | M87280, *Pantoea agglomerans* |
| | S71770, Carotenoid gene cluster |
| | U32636, *Zea mays* phytoene synthase (Y1) gene, complete cds |
| | U62808, *Flavobacterium* ATCC21588 |
| | U87626, *Rubrivivax gelatinosus* |
| | U91900, *Dunaliella bardawil* |
| | X52291, *Rhodobacter capsulatus* |
| | X60441, *L. esculentum* GTom5 gene for phytoene synthase |
| | X63873, *Synechococcus* PCC7942 pys gene for phytoene synthase |
| | X68017, *C. annuum* psy1 mRNA for phytoene synthase |
| | X69172, *Synechocystis* sp. pys gene for phytoene synthase |
| | X78814, *N. pseudonarcissus* |
| crtZ (β-carotene hydroxylase) | D58420, *Agrobacterium aurantiacum* |
| | D58422, *Alcaligenes* sp. |
| | D90087, *E. uredovora* |
| | M87280, *Pantoea agglomerans* |
| | U62808, *Flavobacterium* ATCC21588 |
| | Y15112, *Paracoccus marcusii* |

TABLE 2-continued

Sources of Genes Encoding the Lower Carotenoid Biosynthetic Pathway

| Gene | GenBank Accession Number and Source Organism |
|---|---|
| crtW (β-carotene ketolase) | AF218415, *Bradyrhizobium* sp. ORS278<br>D45881, *Haematococcus pluvialis*<br>D58420, *Agrobacterium aurantiacum*<br>D58422, *Alcaligenes* sp.<br>X86782, *H. pluvialis*<br>Y15112, *Paracoccus marcusii* |
| crtO (β-C4-ketolase) | X86782, *H. pluvialis*<br>Y15112, *Paracoccus marcusii* |
| crtU (β-carotene dehydrogenase) | AF047490, *Zea mays*<br>AF121947, *Arabidopsis thaliana*<br>AF139916, *Brevibacterium linens*<br>AF195507, *Lycopersicon esculentum*<br>AF272737, *Streptomyces griseus* strain IFO13350<br>AF372617, *Citrus* x *paradisi*<br>AJ133724, *Mycobacterium aurum*<br>AJ224683, *Narcissus pseudonarcissus*<br>D26095 and U38550, *Anabaena* sp.<br>X89897, *C. annuum*<br>Y15115, *Anabaena* PCC7210 crtQ gene |
| crtA (spheroidene monooxygenase) | AJ010302, *Rhodobacter sphaeroides*<br>Z11165 and X52291, *Rhodobacter capsulatus* |
| crtC (hydroxyneurosporene synthase) | AB034704, *Rubrivivax gelatinosus*<br>AF195122 and AJ010302, *Rhodobacter sphaeroides*<br>AF287480, *Chlorobium tepidum*<br>U73944, *Rubrivivax gelatinosus*<br>X52291 and Z11165, *Rhodobacter capsulatus*<br>Z21955, *M.xanthus* |
| crtD (carotenoid 3,4-desaturase) | AJ010302 and X63204, *Rhodobacter sphaeroides*<br>U73944, *Rubrivivax gelatinosus*<br>X52291 and Z11165, *Rhodobacter capsulatus* |
| crtF (1-OH-carotenoid methylase) | AB034704, *Rubrivivax gelatinosus*<br>AF288602, *Chloroflexus aurantiacus*<br>AJ010302, *Rhodobacter sphaeroides*<br>X52291 and Z11165, *Rhodobacter capsulatus* |

The majority of the most preferred crt genes are primarily from *Panteoa stewartii*. Sequences of these preferred genes are presented as the following SEQ ID numbers: the crtE gene (SEQ ID NO:1), the crtX gene (SEQ ID NO:3), crtY (SEQ ID NO:5), the crtI gene (SEQ ID NO:7), the crtB gene (SEQ ID NO:9) and the crtZ gene (SEQ ID NO:11).

By using various combinations of the genes presented in Table 2 and the preferred genes of the present invention, innumerable different carotenoids and carotenoid derivatives can be made using the methods of the present invention, provided that sufficient sources of FPP are available in the host organism. For example, the gene cluster crtEXYIB enables the production of β-carotene. Addition of the crtZ to crtEXYIB enables the production of zeaxanthin.

It is envisioned that useful products of the present invention will include any carotenoid compound as defined herein including, but not limited to antheraxanthin, adonixanthin, astaxanthin, canthaxanthin, capsorubrin, β-cryptoxanthin, didehydrolycopene, didehydrolycopene, β-carotene, ζ-carotene, δ-carotene, γ-carotene, keto-γ-carotene, ψ-carotene, ε-carotene, β,ψ-carotene, torulene, echinenone, gamma-carotene, zeta-carotene, alpha-cryptoxanthin, diatoxanthin, 7,8-didehydroastaxanthin, fucoxanthin, fucoxanthinol, isorenieratene, β-isorenieratene lactucaxanthin, lutein, lycopene, neoxanthin, neurosporene, hydroxyneurosporene, peridinin, phytoene, rhodopin, rhodopin glucoside, siphonaxanthin, spheroidene, spheroidenone, spirilloxanthin, uriolide, uriolide acetate, violaxanthin, zeaxanthin-β-diglucoside, zeaxanthin, and C30-carotenoids. Additionally, the invention encompasses derivitization of these molecules to create hydroxy-, methoxy-, oxo-, epoxy-, carboxy-, or aldehydic functional groups, or glycoside esters, or sulfates.

Description of the Preferred Embodiments

Publicly available sequences for several isoprenoid pathway genes in *E. coli* were used to synthesize integration cassettes for λ-Red mediated homologous recombination. One or two PCR-generated fragments were prepared and engineered to contain the phage T5 promoter and a selection marker (Example 1, Tables 1-3). Homology arms, approximately 40-50 bp in length were used on the ends of the PCR generated fragment(s). Homologous recombination, aided by the λ-Red recombinase system encoded on plasmid pKD46, occurred between the *E. coli* chromosome and the integration cassettes, effectively replacing the native promoter of the dxs, idi, lytB, dxr, ygbBygbP(ygbBP), ispA, ychB, gcpE, and ispB genes with the $P_{T5}$ strong promoter (FIGS. 1, 3, and 5). Colonies of transformants were obtained for each of these genes. Successful recombination was measured by the inclusion of a selectable marker (kanamycin). Chromosomal integration of the integration cassettes was confirmed via PCR analysis as described in Example 1 (FIG. 8). λ-Red mediated recombination can occur with one or more integration cassettes, however, the use of at least 2 linear, PCR-generated, cassettes is preferred (FIG. 3).

In another embodiment, a reporter strain of *E. coli* was constructed for assaying β-carotene production. Briefly, the *E. coli* reporter strain was created by cloning the gene cluster crtEXYIB from *Pantoea stewartii* into a helper plasmid (pPCB15; SEQ ID NO:40), which was subsequently used to transform the *E. coli* host strain (FIG. 6). The cluster contained many of the genes required for the synthesis of carotenoids (i.e. β-carotene). It should be noted that the crtZ gene (β-carotene hydroxylase) was included in the gene cluster. However, since no promoter was present to express the crtZ gene (organized in opposite orientation and adjacent to crtB gene) no zeaxanthin was produced, thus, the zeaxanthin glucosyl transferase enzyme (encoded by the crtX gene located within the gene cluster) had no substrate for its reaction. Increases in β-carotene production were reported as increases relative to the control strain production (FIG. 6).

Sequence analysis was conducted to confirm the identification of the gene cluster (Example 4, Table 4) In order to confirm the function of the various carotenoid genes on the helper plasmid, transposon mutagenesis (Example 5) was used. Using this method it was possible to assign function to each of the genes from the transposon mutagenesis results (Table 5). The function assigned to the various *Pantoea stewartii* crt genes was in agreement with that reported in the art (WO 02/079395 A2 and WO 03/016503).

The reporter plasmid, pPCB15, was used to monitor increased flux through the isoprenoid pathway. Modifications to the isoprenoid pathway, which altered the amount of FPP produced, were monitored by the production of β-carotene. Comparisons between the amount of β-carotene produced in the wild type *E. coli* strain and the various transformants were used to select for those strains exhibiting optimal β-carotene production.

In another embodiment, the present method illustrates the ability to use P1 transduction to create an *E. coli* strains having increased β-carotene production. The *E. coli* kan-$P_{T5}$-dxs strain created in Example 1 was infected with bacteriophage P1. Lysate was collected and used to infect *E. coli* MG1655 containing the β-carotene expression plasmid pPCB15 (Example 6, FIG. 6). Transductants were selected via the kanamycin selection marker. A temperature sensitive helper plasmid (pCP20), encoding a site-specific recombinase (FLP), was used to remove the selection marker (ATCC PTA-4455; Cherepanov and Wackernagel, supra; Example 6). The plasmid was cured after removal of the selection marker. PCR fragment analysis was used to confirm incorporation of the $P_{T5}$-dxs cassette and removal of the kanamycin marker (FIG. 8). *E. coli* $P_{T5}$-dxs exhibited approximately a 2.8 fold increase in β-carotene production in comparison to the wild type *E. coli* containing the reporter plasmid (Example 8, FIG. 9).

Figure 9:
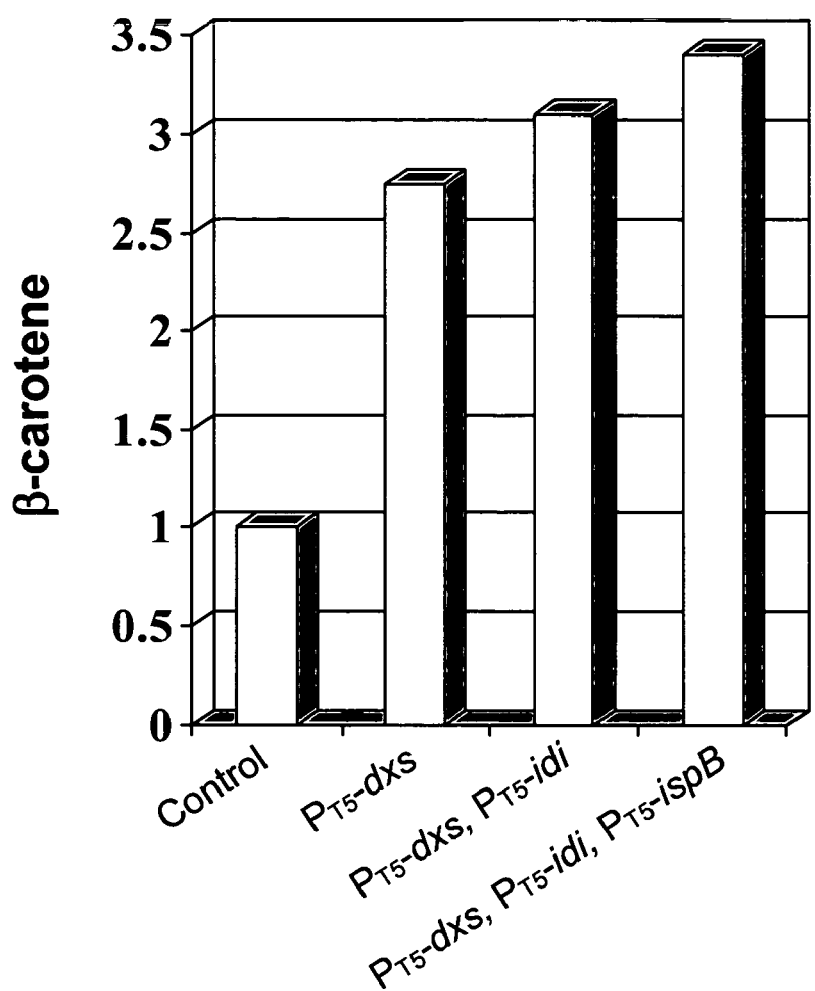
FIG. 9 illustrates increased levels of β-carotene yielded by E. coli strains engineered via the present method.

In order to optimize flux through the isoprenoid pathway, transformants were created containing multiple chromosomal modifications. Bacteriophage P1 transduction was used to create the multiple transformants. Each of the strains were prepared as described in Example 1 and infected with bacteriophage P1. The lytic cycle was allowed to proceed. The lysates of each strain were collected. A mixture of P1 lysates was prepared by mixing equal titers of P1 lysates from each of the individual strains (Example 2, FIG. 7). The P1 lysate mixture was used to infect the *E. coli* $P_{T5}$-dxs strain. Transductants were selected via the selection marker. Transductants exhibiting the deeper yellow pigmentation were selected. Once again, the selection marker was removed. PCR fragment analysis was performed to identify the location and type of insertion for each of the selected transductants (Example 9) and to identify removal of the selection marker (FIG. 8). Removal of the selection marker allowed for the selected strains to act as recipient cells for the next round of P1 transduction. The process was repeated, creating an optimized *E. coli* strain $P_{T5}$-dxs $P_{T5}$-idi $P_{T5}$-ispB exhibiting a 3.4-fold increase in β-carotene production in comparison to the control strain (FIG. 9). Using this process it was possible to efficiently engineer multiple chromosomal modifications into *E. coli*. The isoprenoid pathway was optimized to increase the production of β-carotene, the genetic end product of interest.

In another embodiment, the inclusion of ispB as one of the targets for up-regulation was unexpected as it was believe to divert the carbon flow from the isoprenoid pathway (FIGS. 1 and 9; Example 9). The present method allowed for identification of gene and gene combinations that may be altered using the present method to increased production β-carotene.

In another embodiment, the integration cassettes used in the present method may contain disrupted genes, such as those disrupted by transposon mutagenesis. Down-regulating or completely disrupting genes via chromosomal engineering allows one to divert carbon flow away of competing biosynthetic pathways. The present method facilitates assessment of various combinations of chromosomal modifications and their effect on the desired genetic end product of the targeted biosynthetic pathway.

In one embodiment, the bacterial host strain is engineered to contain multiple chromosomal modifications, including multiple promoter replacements so that the production efficiency of the desired genetic end product is increased. Multiple chromosomal modifications were integrated into one host strain using P1 transduction and a site-specific recombinase to remove selectable markers. Chromosomal modifications were integrated successively into a single strain by successive rounds of P1 transduction and marker removal.

The invention may be used for stacking a variety of targeted in vivo bacterial chromosomal modifications into a single host strain. The removal of the selectable marker using a site-specific recombinase allows for one to conduct multiple chromosomal modifications, necessary for engineering biosynthetic pathways and for optimizing production of industrially useful materials. A combinatorial approach to stacking traits allows the integration of chromosomal modifications with the most impact on the desired trait to be obtained more quickly in comparison to assessing the impact of individual modifications one at a time.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Bestfit" programs were used the default gap creation penalty of 50 and the default gap extension penalty of 3 were used. Multiple alignments were created using the FASTA program incorporating the Smith-Waterman algorithm (W. R. Pearson, *Comput. Methods Genome Res.*, [Proc. Int. Symp.] (1994), Meeting Date 1992, 111-120. Editor(s): Suhai, Sandor. Publisher: Plenum, New York, N.Y.). In any case where program parameters were not prompted for, in these or any other programs, default values were used.

The meaning of abbreviations is as follows: "h" means hour(s), "min" means minute(s), "sec" means second(s), "d" means day(s), "mL" means milliliters, "L" means liters, "µL" means microliters, and "rpm" means revolutions per minute.

Example 1

Synthesis of E. coli Strains with the Phage T5 Strong Promoter Chromosomally Integrated Upstream of the Isoprenoid Genes (Promoter Replacement)

The native promoters of the E. coli isoprenoid genes, dxs, idi, dxr, lytB, ygbBygbP(ygbBP), ispA, ychB, gcpE, and ispB (FIG. 1) were replaced with the phage T5 ($P_{T5}$) strong promoter using a PCR-fragment chromosomal integration method as described in FIG. 3. The method for replacement is based on homologous recombination via the λ Red recombinase encoded on a helper plasmid. Recombination occurs between the E. coli chromosome and one or two PCR fragments that contain 40-50 bp homology patches at both ends of PCR fragments (FIG. 3). Either a two PCR fragment or one PCR fragment method (FIG. 3) was used for chromosomal integration of the kanamycin selectable marker and phage T5 promoter (SEQ ID NO:43) in the front of the E coli isoprenoid genes, dxs, idi, lytB, dxr, ygbBygbP (ygbBP), ispA, ychB, gcpE, and ispB. For the two PCR fragment method, the two fragments included a linear DNA fragment (1489 bp) containing a kanamycin selectable marker flanked by site-specific recombinase target sequences (FRT) and a linear DNA fragment (154 bp) containing a phage T5 promoter ($P_{T5}$) comprising the −10 and −35 consensus promoter sequences, lac operator (lacO), and a ribosomal binding site (rbs). For the one PCR fragment method, the fused linear DNA fragment (1647 bp) contained a kanamycin selectable marker flanked by site-specific recombinase target sequences (FRT) and a linear DNA fragment (154 bp) containing a $P_{T5}$ promoter comprising the −10 and −35 consensus promoter sequences, lac operator (lacO), and a ribosomal binding site (rbs).

By using the two PCR fragment method, the kanamycin selectable marker and $P_{T5}$ promoter (kan-$P_{T5}$) were integrated upstream of the dxs, idi, lytB, dxr, and ygbBP genes, replacing the native promoter of each, yielding kan-$P_{T5}$-dxs, kan-$P_{T5}$-idi, kan-$P_{T5}$-lytB, kan-$P_{T5}$-dxr, and kan-$P_{T5}$-ygbBP. The linear DNA fragment (1489 bp) which contained a kanamycin selectable marker was synthesized by PCR from plasmid pKD4 (Datsenko and Wanner, supra) with primer pairs as follows in Table 3.

TABLE 3

Primers for Amplification of the Kanamycin Selectable Marker

| Primer Name | Primer Sequence | SEQ ID NO: |
|---|---|---|
| 5'-kan(dxs) | TGGAAGCGCTAGCGGACTACATCATCCAG CGTAATAAATAACGTCTTGAGCGATTGTGT AG[1] | 13 |
| 5'-kan(idi) | TCTGATGCGCAAGCTGAAGAAAAATGAGC ATGGAGAATAATATGACGTCTTGAGCGATT GTGTAG[1] | 14 |
| 5'-kan(lytB) | TTTGATATTGAAGTGCTGGAAATCGATCCG GCACTGGAGGCGTAACGTCTTGAGCGATT GTGTAG[1] | 15 |
| 5'-kan(dxr) | GAAGCGGCGCTGGCAGACAAAGAAGCAG AACTGATGCAGTTCTGACGTCTTGAGCGAT TGTGTAG[1] | 16 |
| 5'-kan(ygbBP) | GACGCGTCGAAGCGCGCACAGTCTGCGG GGCAAAACAATCGATAACGTCTTGAGCGA TTGTGTAG[1] | 17 |

TABLE 3-continued

Primers for Amplification of the Kanamycin Selectable Marker

| Primer Name | Primer Sequence | SEQ ID NO: |
|---|---|---|
| 3'-kan | GAAGACGAAAGGGCCTCGTGATACGCCTA TTTTTATAGGTTATATGAATATCCTCCTTAG TTCC[2] | 18 |

[1]The underlined sequences illustrate each respective homology arm chosen to match sequences in the upstream region of the chromosomal integration site, while the remainder is the priming sequence.
[2]The underlined sequences illustrate homology arm chosen to match sequences in the 5'-end region of the T5 promoter DNA fragment.

The second linear DNA fragment (154 bp) containing a $P_{T5}$ promoter was synthesized by PCR from pQE30 (QIAGEN, Inc. Valencia, Calif.) with primer pairs as follows in Table 4.

TABLE 4

Primers for Amplification of the T5 Promoter

| Primer Name | Primer Sequence | SEQ ID NO: |
|---|---|---|
| 5'-T5 | CTAAGGAGGATATTCATATAACCTATAAAAA TAGGCGTATCACGAGGCCC[1] | 19 |
| 3'-T5(dxs) | GGAGTCGACCAGTGCCAGGGTCGGGTATT TGGCAATATCAAAACTCATAGTTAATTTCTC CTCTTTAATG[2] | 20 |
| 3'-T5(idi) | TGGGAACTCCCTGTGCATTCAATAAAATGA CGTGTTCCGTTTGCATAGTTAATTTCTCCTC TTTAATG[2] | 21 |
| 3'-T5(lytB) | CTACCCCGGCACAAAAACCACGTGGGTTG GCCAACAGGATCTGCATAGTTAATTTCTCCT CTTTAATG[2] | 22 |
| 3'-T5(dxr) | TGCAACCAATCGAGCCGGTCGAGCCCAGA ATGGTGAGTTGCTTCATAGTTAATTTCTCCT CTTTAATG[2] | 23 |
| 3'-T5(ygbBP) | CGGCCGCCGGAACCACGGCGCAAACATCC AAATGAGTGGTTGCCATAGTTAATTTCTCCT CTTTAATG[2] | 24 |

[1]The underlined sequences illustrate homology arm chosen to match sequences in the 3'-end region of the kanamycin DNA fragment.
[2]The underlined sequences illustrate each respective homology arm chosen to match sequences in the downstream region of the chromosomal integration site.

For the one PCR fragment method, the kanamycin selectable marker and phage T5 promoter were integrated in the front of ispA, ychB, gcpE, and ispB genes, yielding kan-$P_{T5}$-ispA, kan-$P_{T5}$-ychB, kan-$P_{T5}$-gcpE, and kan-$P_{T5}$-ispB. The linear DNA fragment used for integration and which contained a fused kanamycin selectable marker-phage with $P_{T5}$ promoter was synthesized by PCR from pSUH5 (FIG. 4) with primer pairs as follows in Table 5.

TABLE 5

Primers for Amplification of the Fragment for the One PCR Fragment Method

| Primer Name | Primer Sequence | SEQ ID NO: |
|---|---|---|
| 5'-kanT5(ispA) | AACGAAGACGCCTCTCTAACCCCTTTTAC ACCGGACAATGAGTAACGTCTTGAGCGAT TGTGTAG[1] | 25 |

TABLE 5-continued

Primers for Amplification of the Fragment
for the One PCR Fragment Method

| Primer Name | Primer Sequence | SEQ ID NO: |
|---|---|---|
| 5'-kanT5(ychB) | <u>GGTCAACGCATCAAGTTAAAAATGGATAA CTGGATAGTGAAATAAC</u>GTCTTGAGCGAT TGTGTAG[1] | 26 |
| 5'-kanT5(gcpE) | <u>GTTGCGCGTCTGACCCTCAATGCCGAACA ATCACCGGCGCAGTAAC</u>GTCTTGAGCGAT TGTGTAG[1] | 27 |
| 5'-kanT5(ispB) | <u>ACCATAAACCCTAAGTTGCCTTTGTTCACA GTAAGGTAATCGGGGC</u>GTCTTGAGCGATT GTGTAG[1] | 28 |
| 3'-kanT5(ispA) | <u>CTGGTTGGCCTGCTTAACGCAGGCTTCGA GTTGCTGCGGAAAGTCC</u>ATAGTTAATTTC TCCTCTTTAATG[2] | 29 |
| 3'-kanT5(ychB) | <u>ATAAAAACAGATTAAGTTTTGCCGGAGAG GGCCACTGTGTCCGC</u>ATAGTTAATTTCTC CTCTTTAATG[2] | 30 |
| 3'-kanT5(gcpE) | <u>AAATACGTGTTGATTTTCTACGTTGAATTG GAGCCTGGTTATGCAT</u>AGTTAATTTCTCCT CTTTAATG[2] | 31 |
| 3'-kanT5(ispB) | <u>CGCCATATCTTGCGCGGTTAACTCATTGA TTTTTTCTAAATTCAT</u>AGTTAATTTCTCCTC TTTAATG[2] | 32 |

[1]The underlined sequences illustrate each respective homology arm chosen to match sequences in the upstream region of the chromosomal integration site.
[2]The underlined sequences illustrate each respective homology arm chosen to match sequences in the downstream region of the chromosomal integration site.

Standard PCR conditions were used to amplify the linear DNA fragments with AmpliTaq Gold® polymerase (Applied Biosystems, Foster City, Calif.) as follows:

| PCR reaction: | PCR reaction mixture: |
|---|---|
| Step1 94° C. 3 min | 0.5 μL plasmid DNA |
| Step2 93° C. 30 sec | 5 μL 10X PCR buffer |
| Step3 55° C. 1 min | 1 μL dNTP mixture (10 mM) |
| Step4 72° C. 3 min | 1 μL 5'-primer (20 μM) |
| Step5 Go To Step2, 30 cycles | 1 μL 3'-primer (20 μM) |
| Step6 72° C. 5 min | 0.5 μL AmpliTaq Gold ® polymerase |
|  | 41 μL sterilized dH$_2$O |

After completing the PCR reactions, 50 μL of each PCR reaction mixture was run on a 1% agarose gel and the PCR products were purified using the QIAquick Gel Extraction Kit™ as per the manufacturer's instructions (Cat. # 28704, QIAGEN Inc., Valencia, Calif.). The PCR products were eluted with 10 μL of distilled water. The DNA Clean & Concentrator™ kit (Zymo Research, Orange, Calif.) was used to further purify the PCR product fragments as per the manufacturer's instructions. The PCR products were eluted with 6-8 μL of distilled water to a concentration of 0.5-1.0 μg/μL.

The E. coli MC1061 strain, carrying a λ-Red recombinase expression plasmid pKD46 (amp$^R$) (FIG. 5), was used as a host strain for the chromosomal integration of the PCR fragments. The strain was constructed by transformation of E. coli strain MC1061 with the λ-Red recombinase expression plasmid, pKD46 (amp$^R$). The λ-Red recombinase in pKD46 is comprised of three genes exo, bet, and gam expressed under the control of an arabinose-inducible promoter. Transformants were selected on 100 μg/mL ampicillin LB plates at 30° C.

For transformation, electroporation was performed using 1-5 μg of the purified PCR products carrying the kanamycin marker and P$_{T5}$ promoter. Approximately one-half of the cells transformed were spread on LB plates containing 25 μg/mL kanamycin in order to select antibiotic resistant transformants. After incubating the plate at 37° C. overnight, antibiotic-resistant transformants were selected as follows: 10 colonies of kan-P$_{T5}$-dxs, 12 colonies of kan-P$_{T5}$-idi, 1 colony of kan-P$_{T5}$-lytB, 47 colonies of kan-P$_{T5}$-dxr, 10 colonies of kan-P$_{T5}$-ygbBP, 19 colonies of kan-P$_{T5}$-ispA, 700 colonies of kan-P$_{T5}$-ychB, 21 colonies of kan-P$_{T5}$-gcpE, and 3 colonies of kan-P$_{T5}$-ispB.

PCR analysis was used to screen the selected kan-P$_{T5}$ kanamycin-resistant transformants for integration of both the kanamycin selectable marker and the phage T5 promoter (P$_{T5}$) in the correct location on the E. coli chromosome. For PCR, a colony was resuspended in 50 μL of PCR reaction mixture containing 200 μM dNTPs, 2.5 U AmpliTaq™ (Applied Biosytems), and 0.4 μM of specific primer pairs. Test primers were chosen to match sequences of the regions located in the kanamycin (5'-primer) and the early coding-region of each isoprenoid gene (3'-primer). The PCR reaction was performed as described in above. Chromosomal integration of kan-P$_{T5}$ upstream of each isoprenoid gene was confirmed by PCR analysis. The resultant E. coli strains carrying each kan-P$_{T5}$-isoprenoid gene fusions on the chromosome were used for stacking multiple kan-P$_{T5}$-isoprenoid gene fusions in parallel on the chromosome in a combinatorial approach as described in Examples 7 and 9.

Example 2

Preparation of P1 Lysate Mixture Made with the E. coli kan-P$_{T5}$-dxs, kan-P$_{T5}$-idi, kan-P$_{T5}$-lytB kan-P$_{T5}$-dxr, kan-P$_{T5}$-yqbBP, kan-P$_{T5}$-ispA, kan-P$_{T5}$-ychB, kan-P$_{T5}$-qcpE, and kan-P$_{T5}$-ispB Strains P1 lysates of the E. coli kan-P$_{T5}$-dxs, kan-P$_{T5}$-idi, kan-P$_{T5}$-lytB, kan-P$_{T5}$-dxr, kan-P$_{T5}$-ygbBP, kan-P$_{T5}$-ispA, kan-P$_{T5}$-ychB, kan-P$_{T5}$-gcpE, and kan-P$_{T5}$-ispB strains were prepared by infecting a growing culture of bacteria with the P1 phage and allowing the cells to lyse. For P1 infection, each strain was inoculated in 4 mL LB medium with 25 μg/mL kanamycin, grown at 37° C. overnight, and then sub-cultured with 1:100 dilution of an overnight culture in 10 mL LB medium containing 5 mM CaCl$_2$. After 20-30 min of growth at 37° C., 10$^7$ P1$_{vir}$ phages were added. The cell-phage mixture was aerated for 2-3 hr at 37° C. until lysed, several drops of chloroform were added and the mixture vortexed for 30 sec and incubated for an additional 30 min at room temp. The mixture was then centrifuged for 10 min at 4500 rpm, and the supernatant transferred into a new tube to which several drops of chloroform were added. The lysates were stored at 4° C.

A mixture of P1 lysates was prepared by mixing equal titers of P1 lysate from E. coli kan-P$_{T5}$-dxs, kan-P$_{T5}$-idi, kan-P$_{T5}$-lytB, kan-P$_{T5}$-dxr, kan-P$_{T5}$-ygbBP, kan-P$_{T5}$-ispA, kan-P$_{T5}$-ychB, kan-P$_{T5}$-gcpE, or kan-P$_{T5}$-ispB strains. Titer measurements of the P1 lysates were determined as described in Maniatis.

Example 3

Cloning of β-Carotene Production Genes from Pantoea stewartii

Primers were designed using the sequence from *Erwinia uredovora* to amplify a fragment by PCR containing the crt genes. These sequences included 5'-3':

```
ATGACGGTCTGCGCAAAAAAACACG         SEQ ID 33
GAGAAATTATGTTGTGGATTTGGAATGC      SEQ ID 34
```

Chromosomal DNA was purified from *Pantoea stewartii* (ATCC no. 8199) and Pfu Turbo polymerase (Stratagene, La Jolla, Calif.) was used in a PCR amplification reaction under the following conditions: 94° C., 5 min; 94° C. (1 min)-60° C. (1 min)-72° C. (10 min) for 25 cycles, and 72° C. for 10 min. A single product of approximately 6.5-kb was observed following gel electrophoresis. Taq polymerase (Perkin Elmer, Foster City, Calif.) was used in a ten minute 72° C. reaction to add additional 3' adenosine nucleotides to the fragment for TOPO cloning into pCR4-TOPO (Invitrogen, Carlsbad, Calif.) to create the plasmid pPCB13. Following transformation to *E. coli* DH5α (Life Technologies, Rockville, Md.) by electroporation, several colonies appeared to be bright yellow in color indicating that they were producing a carotenoid compound. Following plasmid isolation as instructed by the manufacturer using the Qiagen (Valencia, Calif.) miniprep kit, the plasmid containing the 6.5 kb amplified fragment was transposed with pGPS1.1 using the GPS-1 Genome Priming System kit (New England Biolabs, Inc., Beverly, Mass.). A number of these transposed plasmids were sequenced from each end of the transposon. Sequence was generated on an ABI Automatic sequencer using dye terminator technology (U.S. Pat. No. 5,366,860; EP 272007) using transposon specific primers. Sequence assembly was performed with the Sequencher program (Gene Codes Corp., Ann Arbor Mich.).

Example 4

Identification and Characterization of Bacterial Genes

Genes encoding crtE, X, Y, I, B, and Z were identified by conducting BLAST (Basic Local Alignment Search Tool; Altschul, S. F., et al., *J. Mol. Biol.* 215:403-410 (1993)) searches for similarity to sequences contained in the BLAST "nr" database (comprising all non-redundant GenBank® CDS translations, sequences derived from the 3-dimensional structure Brookhaven Protein Data Bank, the SWISS-PROT protein sequence database, EMBL, and DDBJ databases). The sequences obtained in Example 3 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J., *Nature Genetics*, 3:266-272 (1993)) provided by the NCBI.

All comparisons were done using either the BLASTNnr or BLASTXnr algorithm. The results of the BLAST comparison are given in Table 6, which summarize the sequences to which they have the most similarity. Table 6 displays data based on the BLASTXnr algorithm with values reported in expect values. The Expected value estimates the statistical significance of the match, specifying the number of matches, with a given score, that are expected in a search of a database of this size absolutely by chance.

TABLE 6

| ORF Name | Gene Name | Similarity Identified | SEQ ID No. Nucleotide | SEQ ID No. Peptide | % Identity[a] | % Similarity[b] | E-value[c] | Citation |
|---|---|---|---|---|---|---|---|---|
| 1 | crtE | Geranylgeranyl pryophosphate synthetase (or GGPP synthetase, or farnesyltranstransferase) EC 2.5.1.29 gi\|117509\|sp\|P21684\|CRTE_PANAN GERANYLGERANYL PYROPHOSPHATE SYNTHETASE (GGPP SYNTHETASE) (FARNESYLTRANSTRANSFERASE) | 1 | 2 | 83 | 88 | e-137 | Misawa et al., J. Bacteriol. 172 (12), 6704-6712 (1990) |
| 2 | crtX | Zeaxanthin glucosyl transferase EC 2.4.1.- gi\|1073294\|pir\|S52583 crtX protein - *Erwinia herbicola* | 3 | 4 | 75 | 79 | 0.0 | Lin et al., Mol. Gen. Genet. 245 (4), 417-423 (1994) |
| 3 | crtY | Lycopene cyclase gi\|1073295\|pir\|S52585 lycopene cyclase - *Erwinia herbicola* | 5 | 6 | 83 | 91 | 0.0 | Lin et al., Mol. Gen. Genet. 245 (4), 417-423 (1994) |
| 4 | crtI | Phytoene desaturaseEC 1.3.-.- gi\|1073299\|pir\|S52586 phytoene dehydrogenase (EC 1.3.-.-)- *Erwinia herbicola* | 7 | 8 | 89 | 91 | 0.0 | Lin et al., Mol. Gen. Genet. 245 (4), 417-423 (1994) |
| 5 | crtB | Phytoene synthaseEC2.5.1- gi\|1073300\|pir\|S52587 prephytoene pyrophosphate synthase - *Erwinia herbicola* | 9 | 10 | 88 | 92 | e-150 | Lin et al., Mol. Gen. Genet. 245 (4), 417-423 (1994) |
| 6 | crtZ | Beta-carotene hydroxylase gi\|117526\|sp\|P21688\|CRTZ_PANAN BETA- | 11 | 12 | 88 | 91 | 3e-88 | Misawa et al., J. |

TABLE 6-continued

| ORF Gene Name | Gene Name | Similarity Identified | SEQ ID No. Nucleotide | SEQ ID No. Peptide | % Identity[a] | % Similarity[b] | E-value[c] | Citation |
|---|---|---|---|---|---|---|---|---|
| | | CAROTENE HYDROXYLASE | | | | | | Bacteriol. 172 (12), 6704-6712 (1990) |

[a] % Identity is defined as percentage of amino acids that are identical between the two proteins.
[b] % Similarity is defined as percentage of amino acids that are identical or conserved between the two proteins.
[c] Expect value. The Expect value estimates the statistical significance of the match, specifying the number of matches, with a given score, that are expected in a search of a database of this size absolutely by chance.

Example 5

Analysis of Gene Function by Transposon Mutagenesis

Several plasmids carrying transposes, which were inserted into each coding region including crtE, crtX, crtY, crtI, crtb, and crtZ, were chosen using sequence data generated in Example 3. These plasmid variants were transformed to *E. coli* MG1655 and grown in 100 mL Luria-Bertani broth in the presence of 100 µg/mL ampicillin. Cultures were grown for 18 hr at 26° C., and the cells were harvested by centrifugation. Carotenoids were extracted from the cell pellets using 10 mL of acetone. The acetone was dried under nitrogen and the carotenoids were resuspended in 1 mL of methanol for HPLC analysis. A Beckman System Gold® HPLC with Beckman Gold Nouveau Software (Columbia, Md.) was used for the study. The crude extraction (0.1 mL) was loaded onto a 125×4 mm RP8 (5 µm particles) column with corresponding guard column (Hewlett-Packard, San Fernando, Calif.). The flow rate was 1 mL/min, while the solvent program used was: 0-11.5 min 40% water/60% methanol; 11.5-20 min 100% methanol; 20-30 min 40% water/60% methanol. The spectrum data were collected by the Beckman photodiode array detector (model 168).

In the wild type clone with wild type crtEXYIBZ, the carotenoid was found to have a retention time of 15.8 min and an absorption spectra of 425, 450 and 478 nm. These values matched those of the β-carotene standard. This suggested that crtZ gene organized in the opposite orientation was not expressed in this construct. The transposon insertion in crtZ had no effect as expected (data not shown).

HPLC spectral analysis also revealed that a clone with transposon insertion in crtX also produced β-carotene. This is consistent with the proposed function of crtx encoding a zeaxanthin glucosyl transferase enzyme at a later step of the carotenoid pathway following synthesis of β-carotene.

The transposon insertion in crty did not produce β-carotene. The carotenoid's elution time (15.2 min) and absorption spectra (443 nm, 469 nm, 500 nm) agreed with those of the lycopene standard. Accumulation of lycopene in the crtY mutant confirmed the role crtY as a lycopene cyclase encoding gene.

The crtI extraction, when monitored at 286 nm, had a peak with retention time of 16.3 min and with absorption spectra of 276 nm, 286 nm, 297 nm, which agreed with the reported spectrum for phytoene. Detection of phytoene in the crtI mutant confirmed the function of the crtI gene as one encoding a phytoene dehydrogenase enzyme.

The acetone extracted from the crtE mutant or crtB mutant was clear. Loss of pigmented carotenoids in these mutants indicated that both the crtE gene and crtB genes are essential for carotenoid synthesis. No carotenoid was observed in either mutant, which is consistent with the proposed function of crtB encoding a prephytoene pyrophosphate synthase and crtE encoding a geranylgeranyl pyrophosphate synthetase. Both enzymes are required for β-carotene synthesis.

Results of the transposon mutagenesis experiments are shown below in Table 7. The site of transposon insertion into the gene cluster crtEXYIB is recorded, along with the color of the *E. coli* colonies observed on LB plates, the identity of the carotenoid compound (as determined by HPLC spectral analysis), and the experimentally assigned function of each gene.

TABLE 7

Transposon Insertion Analysis of Carotenoid Gene Function

| Transposon insertion site | Colony color | Carotenoid observed by HPLC | Assigned gene function |
|---|---|---|---|
| Wild Type (with no transposon insertion) | Yellow | β-carotene | |
| crtE | White | None | Geranylgeranyl pyrophosphate synthetase |
| crtB | White | None | Prephytoene pyrophosphate synthase |
| crtI | White | Phytoene | Phytoene dehydrogenase |
| crtY | Pink | Lycopene | Lycopene cyclase |
| crtZ | Yellow | β-carotene | β-carotene hydroxylase |
| crtX | Yellow | β-carotene | Zeaxanthin glucosyl transferase |

Example 6

Construction of *E. coli* $P_{T5}$-dxs that Produces β-Carotene

In order to characterize the effect of the phage T5 promoter on isoprenoid production, a strain, *E. coli* $P_{T5}$-dxs, containing a chromosomally integrated T5 promoter upstream from an isoprenoid gene, capable of producing β-carotene, was constructed.

P1 lysate made on *E. coli* kan-$P_{T5}$dxs strain was transduced into the recipient strain, *E. coli* MG1655 containing a β-carotene biosynthesis expression plasmid pPCB15 ($cam_R$) (FIG. 6). The plasmid pPCB15 ($cam^R$) contains the carotenoid biosynthesis gene cluster (crtEXYIB) from *Pantoea Stewartii* (ATCC no. 8199). The pPCB15 plasmid was constructed from ligation of SmaI digested pSU18 (Bartolome, B. et al., *Gene*, 102:75-78 (1991)) vector with a blunt-ended PmeI/NotI fragment carrying crtEXYIB from pPCB13 (Example 3). The *E. coli* MG1655 pPCB15 recipient cells were grown to mid-log phase (1-2×10$^8$ cells/mL) in 4 mL LB medium with 25 µg/mL chloramphenicol at 37° C. Cells were spun down for 10 min at 4500 rpm and resuspended in 2 mL of 10 mM MgSO$_4$ and 5 mM CaCl$_2$. Recipient cells (100 µL) were mixed with 1 µL, 2 µL, 5 µL, or 10 µL of P1 lysate stock (10$^7$ pfu/µL) made from the *E. coli* kan-P$_{T5}$dxs strain and incubated at 30° C. for 30 min. The recipient cell-lysate mixture was spun down at 6500 rpm for 30 sec, resuspended in 100 µL of LB medium with 10 mM of sodium citrate, and incubated at 37° C. for 1 h. Cells were plated on LB plates containing both 25 µg/mL kanamycin and 25 µg/mL of chloramphenicol in order to select for antibiotic-resistant transductants and incubated at 37° C. for 1 or 2 days. Sixteen transductants were selected.

To eliminate kanamycin selectable marker from the chromosome, a FLP recombinase expression plasmid pCP20 (amp$^R$) (ATCC PTA-4455) (Cherepanov and Wackernagel, *Gene*, 158:9-14 (1995)), which has a temperature-sensitive replication of origin, was transiently transformed into one of the kanamycin-resistant transductants by electroporation. Cells were spread onto LB agar containing 100 µg/mL ampicillin and 25 µg/mL chloramphenicol LB plates, and grown at 30° C. for 1 day. Colonies were picked and streaked on 25 µg/mL chloramphenicol LB plates without ampicillin antibiotics and incubated at 43° C. overnight. Plasmid pCP20 has a temperature sensitive origin of replication and was cured from the host cells by culturing cells at 43° C. The colonies were tested for ampicillin and kanamycin sensitivity to test loss of pCP20 and kanamycin selectable marker by streaking colonies on 100 µg/mL ampicillin LB plate or 25 µg/mL kanamycin LB plate. Elimination of the kanamycin selectable marker from the *E. coli* chromosome was confirmed by PCR analysis (FIG. 8, lane 1 and 2). The selected colonies were resuspended in 50 µL of PCR reaction mixture containing 200 µM dNTPs, 2.5 U AmpliTaq™ (Applied Biosytems), and 0.4 µM of different combination of specific primer pairs, T-kan (5'-ACCG-GATATCACCACTTAT CTGCTC-3')(SEQ ID NO:35) and B-dxs (5'-TGGCAACAGTCGTAGCTCCTGGG TGG-3') (SEQ ID NO:36), T-T5 (5'-TAACCTATAAAAATAGGCG-TATCACGAGG CCC-3')(SEQ ID NO:37) and B-dxs. Test primers were chosen to amplify regions located either in the kanamycin or the phage T5 promoter and the early region of dxs gene (FIG. 8). The PCR reaction was performed as described in Example 1. The PCR results (FIG. 8, lane 1 and 2) indicated the elimination of the kanamycin selectable marker from the *E coli* chromosome. The presence of the P$_{T5}$ promoter fragment upstream of the dxs coding sequence was confirmed based on the production of a PCR product of the expected size (229 bp). In this manner the *E. coli* P$_{T5}$-dxs strain was constructed.

Example 7

Combinatorial Stacking of Multiple kan-P$_{T5}$-Isoprenoid Gene Fusions in Parallel In order to create a bacterial strain capable of high level of carotenoid production, a method was devised for stacking P$_{T5}$ in front of multiple isoprenoid genes in parallel. Using this technique enabled one to then select for the best carotenoid producing strain.

Figure 7:
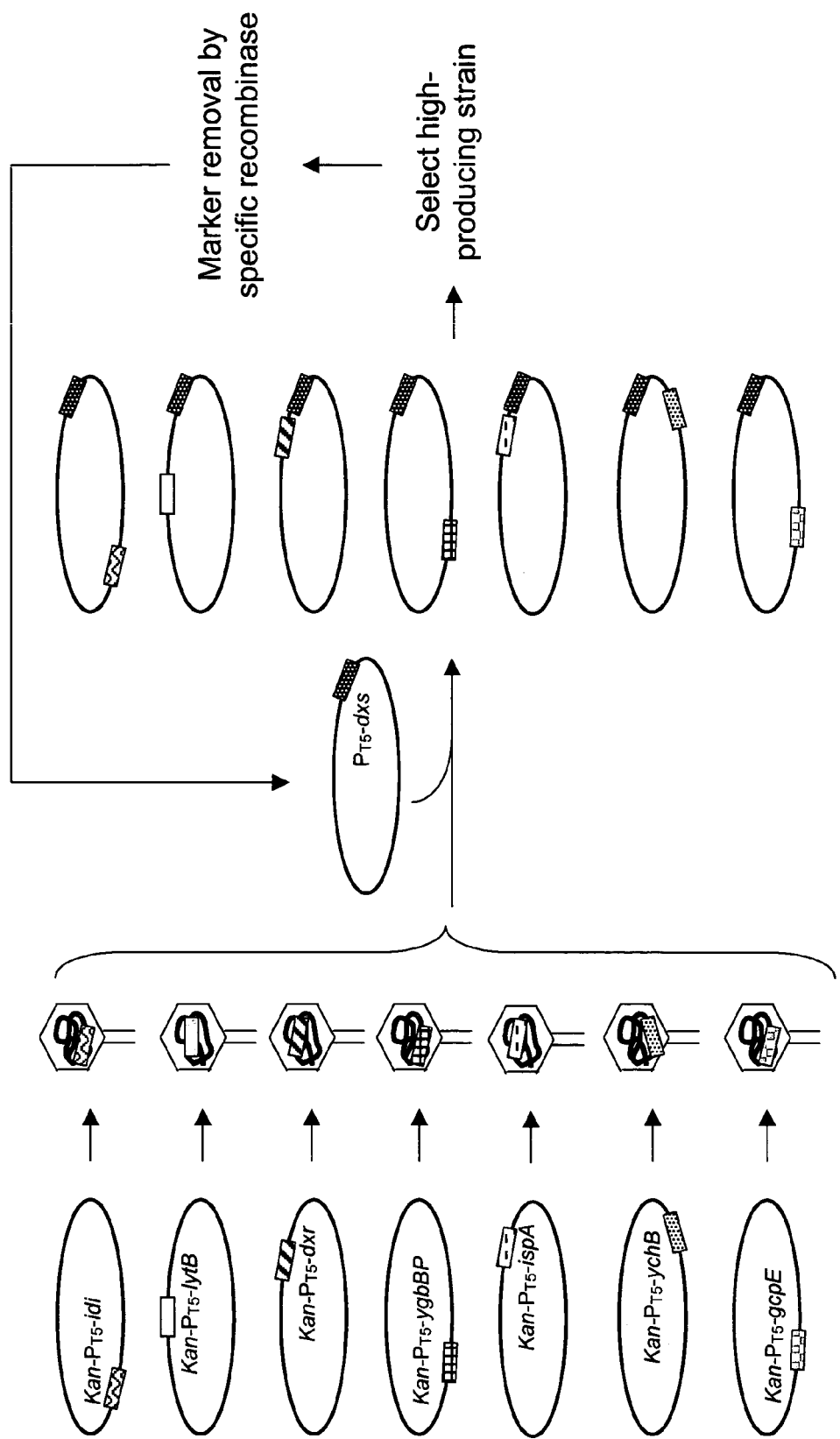
FIG. 7 illustrates the scheme for increasing β-carotene levels in E. coli via the method of the invention.

*E. coli* P$_{T5}$-dxs strain was transduced with P1 lysate mixture made with *E. coli* kan-P$_{T5}$-idi, kan-P$_{T5}$-lytB, kan-P$_{T5}$-dxr, kan-P$_{T5}$-ygbBP, kan-P$_{T5}$-ispA, kan-P$_{T5}$-ychB, kan-P$_{T5}$-gcpE, and kan-P$_{T5}$-ispB strains as described in Example 2, which allowed stacking kan-P$_{T5}$ cassettes in front of multiple isoprenoid genes in parallel (FIG. 7). For transduction, the recipient cells were prepared and transduction was carried out as in Example 6 using the P1 lysate mixture (10$^6$ pfu/µL). Cells were plated on LB plates containing both 25 µg/mL kanamycin and 25 µg/mL chloramphenicol in order to select antibiotic-resistant transductants. After incubation at 37° C. for 1-2 days, six colonies out of 430 kanamycin/chloramphenicol-resistant transductants that were most deeply pigmented with the characteristic yellow β-carotene color were selected. The kan-P$_{T5}$-isoprenoid gene fusions stacked on the chromosome in these six strains were identified by PCR analysis with a 5'-primer complementary to the middle region of the kanamycin gene and a 3'-primer complementary to the sequence within the first several hundred bp of each isoprenoid gene (idi, lytB, dxr, ygbBP, ispA, ychB, gcpE, or ispB). This PCR screening was performed as outlined in Example 1. PCR analysis showed that in addition to the P$_{T5}$-dxs, four colonies contained kan-P$_{T5}$-idi, one contained kan-PT$_5$-ispB, and one contained kan-P$_{T5}$-gcpE. Among these, colonies carrying kan-P$_{T5}$-idi showed the deepest yellow color on an LB plate containing both 25 µg/mL kanamycin and 25 µg/mL chloramphenicol after growth at 37° C. for 2 days, which suggested higher yields of β-carotene production.

The kanamycin selectable marker from the chromosome of *E. coli* P$_{T5}$-dxs kan-P$_{T5}$-idi was eliminated as described in Example 2, yielding *E. coli* P$_{T5}$-dxs P$_{T5}$-idi. The elimination of the kanamycin selectable marker was confirmed by PCR analysis as described in Example 1 using different combinations of specific primer pairs, T-kan and B-idi (5'-TCAT-GCTGACCTGGTGAAGGAATCC-3')(SEQ ID NO:38), T-T5 and B-idi. Test primers were chosen to amplify regions located either in the kanamycin or the P$_{T5}$ promoter and the beginning of the idi gene (FIG. 8). The PCR results (FIG. 8, lane 3 and 4) indicated the elimination of the kanamycin selectable marker from the *E. coli* chromosome. As before, the presence of the P$_{T5}$ promoter fragment in the front of chromosomal idi gene was confirmed based on the production of a PCR fragment of the expected size (274 bp).

Example 8

Measurement of β-carotene Production in *E. coli* P$_{T5}$-dxs P$_{T5}$-idi

β-carotene production of *E. coli* P$_{T5}$-dxs P$_{T5}$-idi, *E. coli* P$_{T5}$-dxs, and *E. coli* control strains all of which contain a β-carotene biosynthesis expression plasmid pPCB15 (cam$^R$) was quantified by a spectrophotometric method. The quantitative analysis of β-carotene production was achieved by measuring the spectra of β-carotene's characteristic λ$_{max}$ peaks at 425, 450 and 478 nm. *E. coli* P$_{T5}$-dxs P$_{T5}$-idi, *E. coli* P$_{T5}$-dxs and the *E. coli* control strains were grown in 5 mL LB containing 25 µg/mL chloramphenicol at 37° C. for 24 hr, and then harvested by centrifugation at 4,000 rpm for 10 min. The β-carotene pigment was extracted by resuspending cell pellet in 1 mL of acetone with vortexing for 1 min and then rocking the sample for 1 h at room temperature. Following centrifugation at 4,000 rpm for 10 min, the absorption spectrum of the acetone layer containing β-carotene was measured at λ 450 nm using an Ultrospec 3000 spectrophotometer (Amersham Biosciences, Piscataway, N.J.). The production of β-carotene in *E. coli* P$_{T5}$-dxs and *E. coli* P$_{T5}$-dxs P$_{T5}$-4idi was approximately 2.8-fold and 3.1-fold higher than that of the *E. coli* control strain, respectively (FIG. 9). The production of β-carotene in *E. coli* P$_{T5}$-dxs P$_{T5}$-idi increased approximately 12% when compared to the parental strain *E. coli* P$_{T5}$-dxs.

Example 9

Transduction of *E. coli* P$_{T5}$-dxs P$_{T5}$-idi with the P1 Lysate Mixture for Creation of a Better β-carotene Producer

*E. coli* P$_{T5}$-dxs P$_{T5}$-idi strain was transduced with P1 lysate mixture made on *E. coli* kan-P$_{T5}$-lytB, kan-P$_{T5}$-dxr, kan-P$_{T5}$-ygbBP, kan-P$_{T5}$-ispA, kan-P$_{T5}$-ychB, kan-P$_{T5}$-gcpE, and kan-P$_{T5}$-ispB strains (FIG. 7). P1 transduction was performed as described in Example 7. Greater than 1000 transductants were produced. Among these transductants, 10 colonies that exhibited deeper yellow color than the parental strain *E. coli* P$_{T5}$-dxs P$_{T5}$-idi were chosen and the location of the insertion of kan-P$_{T5}$ identified by PCR analysis as described in Example 7. PCR analysis showed that all ten colonies contained kan-P$_{T5}$-ispB as well as P$_{T5}$-dxs and P$_{T5}$-idi. *E. coli* P$_{T5}$-dxs P$_{T5}$-idi kan-P$_{T5}$-ispB strain exhibited deeper yellow color than the parental strain *E. coli* P$_{T5}$-dxs P$_{T5}$-idi on an LB plate containing both 25 µg/mL kanamycin and 25 µg/mL chloramphenicol after growing at 37° C. for 2 days, suggesting higher yields of β-carotene production.

The kanamycin selectable marker from the chromosome of *E. coli* P$_{T5}$-dxs P$_{T5}$-idi kan-P$_{T5}$-ispB was eliminated as described in Example 6, yielding *E. coli* P$_{T5}$-dxs P$_{T5}$-idi P$_{T5}$-ispB. The elimination of the kanamycin selectable marker was confirmed by PCR analysis (FIG. 8, lane 5 and 6). The specific primer pairs, T-kan (SEQ ID NO:35) and B-ispB (5'-ACCATAAACCCTAAGTTGCCTTT GTTCA-CAGTAAGGT AATCGGGG-3')(SEQ ID NO:39), T-T5 (SEQ ID NO:37) and B-ispB (SEQ ID NO:39) were used. Test primers were chosen to amplify regions located either in the kanamycin or the P$_{T5}$ promoter and the beginning of the ispB gene (FIG. 8). The PCR reaction was performed as described in Example 1. The PCR results (FIG. 8, lane 5 and 6) indicated the elimination of the kanamycin selectable marker from *E. coli* chromosome and the presence of the P$_{T5}$ promoter fragment in the front of chromosomal ispB gene based on the production of a band of the expected size (203 bp) which corresponds to the size of the P1 P$_{T5}$ promoter sequence.

β-carotene production of *E. coli* P$_{T5}$-dxs P$_{T5}$-idi P$_{T5}$-ispB, *E. coli* P$_{T5}$-dxs P$_{T5}$-idi, *E. coli* P$_{T5}$-dxs and *E. coli* control strains was compared using the spectrophotometric method as described in Example 8 (FIG. 9). The production of β-carotene in *E. coli* P$_{T5}$-dxs P$_{T5}$-idi P$_{T5}$-ispB was 3.4-fold higher than in the *E. coli* control strain (FIG. 9). The production of β-carotene in *E. coli* P$_{T5}$-dxs P$_{T5}$-idi P$_{T5}$-ispB increased approximately 10% when compared to the parental strain *E. Coli* P$_{T5}$-dxs P$_{T5}$-idi.

The present combinatorial P1 transduction method enabled, for the first time, isolation of the ispB gene capable of increasing the production of β-carotene under the control of the strong promoter. The isolation of ispB for increasing the production of β-carotene was an unexpected and non-obvious result because IspB, the enzyme octaprenyl diphosphate synthase, which supplied the precursor of the side chain of the isoprenoid quinones was expected to drain away the FPP precursor from the carotenoid biosynthetic pathway (FIG. 1). The mechanism of how overexpression of the ispB gene, under the control of phage T5 strong promoter, increased the β-carotene production is not clear yet. However, the result suggests that IspB may increase the flux of the carotenoid biosynthetic pathway. Combinatorial transduction is a powerful tool for the identification of new genes in biosynthetic pathway optimization.

---

What is claimed is:

1. A method for the optimization of the production of a genetic end product comprising:
   a) providing a multiplicity of integration cassettes, each cassette comprising:
   (i) a promoter;
   (ii) a selectable marker bounded by specific recombinase sites responsive to a recombinase;
   (iii) regions of homology to different portions of a P1 donor cell chromosome;
   b) transforming at least one donor cell with at least one of the multiplicity of integration cassettes of (a) for chromosomal integration;
   c) infecting the at least one transformed donor cell of (b) with a P1 phage wherein the phage replicates and the at least one transformed donor cell is lysed;
   d) isolating phage released by the lysis of the at least one transformed donor cell of (c);
   e) mixing equal number of isolated phage released by the lysis of a set of donor cells of (c) carrying different integration cassettes of (a);
   f) infecting at least one recipient cell with the mixture of the isolated phage of (e) wherein the integration cassettes each integrate into the at least one recipient cell chromosome at the point of homology to the homology arms;
   g) growing the at least one infected recipient cell of (f) so that a population of transduced recipient cells containing the selectable marker is produced;
   h) selecting transduced recipient cells of (g) on the basis of the selectable marker;
   i) screening the transduced recipient cells of (h) for the highest level of the genetic end product to identify a first overproducing strain;
   j) activating a recombinase in the first overproducing strain of (i) which excises the selectable marker from the chromosomally integrated integration cassette;
   k) infecting the first overproducing strain of (j) with the mixture of the isolated phage of (e) wherein the integration cassettes each integrate into the first overproducing strain chromosome at the point of homology on the homology arms;
   l) growing the first overproducing strain of (k) so that a population of first overproducing strain containing the selectable marker is produced;
   m) selecting first overproducing strain of (l) on the basis of the selectable marker;
   n) screening the first overproducing strain of (m) for the highest level of the genetic end product to identify a second overproducing strain; and
   o) comparing the levels of genetic end product produced by the first and second overproducing strains whereby the production of the genetic end product is optimized.

2. A method according to claim 1 wherein each promoter is a native promoter of a cell other than the donor cell or recipient cell.

3. A method according to claim 1 wherein the promoter is selected from the group consisting of lac, ara, tet, trp, $\lambda P_L$, $\lambda P_R$, T7, tac, $P_{T5}$, and trc.

4. A method according to claim 1 wherein the promoter is $P_{T5}$.

5. A method according to claim 1 wherein the donor cell and recipient cell have the genes that comprise the isoprenoid biosynthetic pathway.

6. A method according to claim 5 wherein the integration cassette integrates into the recipient chromosome so as to operably link the promoter and a gene of the isoprenoid biosynthetic pathway.

7. A method according to claim 6 wherein the gene of the isoprenoid biosynthetic pathway is selected from the group consisting of dxs, dxr, ygbP, ychB, ygbB, idi, ispA, lytB, gcpE, ispB, crtE, crtY, crtI, crtB, crtX, crtW, crtO, crtR, and crtZ.

8. A method according to claim 6 wherein the genetic end product is a carotenoid selected from the group consisting of antheraxanthin, adonixanthin, astaxanthin, canthaxanthin, capsorubrin, β-cryptoxanthin, didehydrolycopene, β-carotene, ζ-carotene, δ-carotene, Y-carotene, keto-Y-carotene, ψ-carotene, ε-carotene, β,ψ-carotene, torulene, echinenone, alpha-cryptoxanthin, diatoxanthin, 7,8-didehydroastaxanthin, fucoxanthin, fucoxanthinol, isorenieratene, β-isorenieratene, lactucaxanthin, lutein, lycopene, neoxanthin, neurosporene, hydroxyneurosporene, peridinin, phytoene, rhodopin, rhodopin glucoside, siphonaxanthin, spheroidene, spheroidenone, spirilloxanthin, uriolide, uriolide acetate, violaxanthin, zeaxanthin-β-diglucoside, zeaxanthin, and C30-carotenoids.

* * * * *

SEQUENCE LISTING

```
<160> NUMBER OF SEQ ID NOS: 43

<210> SEQ ID NO 1
<211> LENGTH: 912
<212> TYPE: DNA
<213> ORGANISM: Pantoea stewartii
<220> FEATURE:
<221> NAME/KEY: misc_feature
<222> LOCATION: (1)..(3)
<223> OTHER INFORMATION: Alternative start codon usage TTG instead of
      ATG

<400> SEQUENCE: 1
ttgacggtct gcgcaaaaaa acacgttcac cttactggca tttcggctga gcagttgctg      60
gctgatatcg atagccgcct tgatcagtta ctgccggttc agggtgagcg ggattgtgtg     120
ggtgccgcga tgcgtgaagg cacgctggca ccgggcaaac gtattcgtcc gatgctgctg     180
ttattaacag cgcgcgatct tggctgtgcg atcagtcacg ggggattact ggatttagcc     240
tgcgcggttg aaatggtgca tgctgcctcg ctgattctgg atgatatgcc ctgcatggac     300
gatgcgcaga tgcgtcgggg gcgtcccacc attcacacgc agtacggtga acatgtggcg     360
attctggcgg cggtcgcttt actcagcaaa gcgtttgggg tgattgccga ggctgaaggt     420
ctgacgccga tagccaaaac tcgcgcggtg tcggagctgt ccactgcgat tggcatgcag     480
```

-continued

```
ggtctggttc agggccagtt taaggacctc tcggaaggcg ataaacccccg cagcgccgat    540 gccatactgc taaccaatca gtttaaaacc agcacgctgt tttgcgcgtc aacgcaaatg    600
gcgtccattg cggccaacgc gtcctgcgaa gcgcgtgaga acctgcatcg tttctcgctc    660
gatctcggcc aggcctttca gttgcttgac gatcttaccg atggcatgac cgataccggc    720
aaagacatca atcaggatgc aggtaaatca acgctggtca atttattagg ctcaggcgcg    780
gtcgaagaac gcctgcgaca gcatttgcgc ctggccagtg aacacctttc cgcggcatgc    840
caaaacggcc attccaccac ccaactttt attcaggcct ggtttgacaa aaaactcgct    900
gccgtcagtt aa                                                         912
```

<210> SEQ ID NO 2
<211> LENGTH: 303
<212> TYPE: PRT
<213> ORGANISM: Pantoea stewartii

<400> SEQUENCE: 2

```
Met Thr Val Cys Ala Lys Lys His Val His Leu Thr Gly Ile Ser Ala
  1               5                  10                  15

Glu Gln Leu Leu Ala Asp Ile Asp Ser Arg Leu Asp Gln Leu Leu Pro
                 20                  25                  30

Val Gln Gly Glu Arg Asp Cys Val Gly Ala Ala Met Arg Glu Gly Thr
             35                  40                  45

Leu Ala Pro Gly Lys Arg Ile Arg Pro Met Leu Leu Leu Leu Thr Ala
         50                  55                  60

Arg Asp Leu Gly Cys Ala Ile Ser His Gly Gly Leu Leu Asp Leu Ala
 65                  70                  75                  80

Cys Ala Val Glu Met Val His Ala Ala Ser Leu Ile Leu Asp Asp Met
                 85                  90                  95

Pro Cys Met Asp Asp Ala Gln Met Arg Arg Gly Arg Pro Thr Ile His
            100                 105                 110

Thr Gln Tyr Gly Glu His Val Ala Ile Leu Ala Ala Val Ala Leu Leu
        115                 120                 125

Ser Lys Ala Phe Gly Val Ile Ala Glu Ala Glu Gly Leu Thr Pro Ile
    130                 135                 140

Ala Lys Thr Arg Ala Val Ser Glu Leu Ser Thr Ala Ile Gly Met Gln
145                 150                 155                 160

Gly Leu Val Gln Gly Gln Phe Lys Asp Leu Ser Glu Gly Asp Lys Pro
                165                 170                 175

Arg Ser Ala Asp Ala Ile Leu Leu Thr Asn Gln Phe Lys Thr Ser Thr
            180                 185                 190

Leu Phe Cys Ala Ser Thr Gln Met Ala Ser Ile Ala Ala Asn Ala Ser
        195                 200                 205

Cys Glu Ala Arg Glu Asn Leu His Arg Phe Ser Leu Asp Leu Gly Gln
    210                 215                 220

Ala Phe Gln Leu Leu Asp Asp Leu Thr Asp Gly Met Thr Asp Thr Gly
225                 230                 235                 240

Lys Asp Ile Asn Gln Asp Ala Gly Lys Ser Thr Leu Val Asn Leu Leu
                245                 250                 255

Gly Ser Gly Ala Val Glu Glu Arg Leu Arg Gln His Leu Arg Leu Ala
            260                 265                 270

Ser Glu His Leu Ser Ala Ala Cys Gln Asn Gly His Ser Thr Thr Gln
        275                 280                 285

Leu Phe Ile Gln Ala Trp Phe Asp Lys Lys Leu Ala Ala Val Ser
    290                 295                 300
```

-continued

```
                      290                 295                 300

<210> SEQ ID NO 3
<211> LENGTH: 1296
<212> TYPE: DNA
<213> ORGANISM: Pantoea stewartii
<220> FEATURE:
<221> NAME/KEY: CDS
<222> LOCATION: (1)..(1296)

<400> SEQUENCE: 3 atg agc cat ttt gcg gtg atc gca ccg ccc ttt ttc agc cat gtt cgc        48
Met Ser His Phe Ala Val Ile Ala Pro Pro Phe Phe Ser His Val Arg
1               5                  10                  15 gct ctg caa aac ctt gct cag gaa tta gtg gcc cgc ggt cat cgt gtt        96
Ala Leu Gln Asn Leu Ala Gln Glu Leu Val Ala Arg Gly His Arg Val
                20                  25                  30 acg ttt ttt cag caa cat gac tgc aaa gcg ctg gta acg ggc agc gat       144
Thr Phe Phe Gln Gln His Asp Cys Lys Ala Leu Val Thr Gly Ser Asp
            35                  40                  45 atc gga ttc cag acc gtc gga ctg caa acg cat cct ccc ggt tcc tta       192
Ile Gly Phe Gln Thr Val Gly Leu Gln Thr His Pro Pro Gly Ser Leu
        50                  55                  60 tcg cac ctg ctg cac ctg gcc gcg cac cca ctc gga ccc tcg atg tta       240
Ser His Leu Leu His Leu Ala Ala His Pro Leu Gly Pro Ser Met Leu
65                  70                  75                  80 cga ctg atc aat gaa atg gca cgt acc agc gat atg ctt tgc cgg gaa       288
Arg Leu Ile Asn Glu Met Ala Arg Thr Ser Asp Met Leu Cys Arg Glu
                85                  90                  95 ctg ccc gcc gct ttt cat gcg ttg cag ata gag ggc gtg atc gtt gat       336
Leu Pro Ala Ala Phe His Ala Leu Gln Ile Glu Gly Val Ile Val Asp
                100                 105                 110 caa atg gag ccg gca ggt gca gta gtc gca gaa gcg tca ggt ctg ccg       384
Gln Met Glu Pro Ala Gly Ala Val Val Ala Glu Ala Ser Gly Leu Pro
            115                 120                 125 ttt gtt tcg gtg gcc tgc gcg ctg ccg ctc aac cgc gaa ccg ggt ttg       432
Phe Val Ser Val Ala Cys Ala Leu Pro Leu Asn Arg Glu Pro Gly Leu
        130                 135                 140 cct ctg gcg gtg atg cct ttc gag tac ggc acc agc gat gcg gct cgg       480
Pro Leu Ala Val Met Pro Phe Glu Tyr Gly Thr Ser Asp Ala Ala Arg
145                 150                 155                 160 gaa cgc tat acc acc agc gaa aaa att tat gac tgg ctg atg cga cgt       528
Glu Arg Tyr Thr Thr Ser Glu Lys Ile Tyr Asp Trp Leu Met Arg Arg
                165                 170                 175 cac gat cgt gtg atc gcg cat cat gca tgc aga atg ggt tta gcc ccg       576
His Asp Arg Val Ile Ala His His Ala Cys Arg Met Gly Leu Ala Pro
                180                 185                 190 cgt gaa aaa ctg cat cat tgt ttt tct cca ctg gca caa atc agc cag       624
Arg Glu Lys Leu His His Cys Phe Ser Pro Leu Ala Gln Ile Ser Gln
            195                 200                 205 ttg atc ccc gaa ctg gat ttt ccc cgc aaa gcg ctg cca gac tgc ttt       672
Leu Ile Pro Glu Leu Asp Phe Pro Arg Lys Ala Leu Pro Asp Cys Phe
        210                 215                 220 cat gcg gtt gga ccg tta cgg caa ccc cag ggg acg ccg ggg tca tca       720
His Ala Val Gly Pro Leu Arg Gln Pro Gln Gly Thr Pro Gly Ser Ser
225                 230                 235                 240 act tct tat ttt ccg tcc ccg gac aaa ccc cgt att ttt gcc tcg ctg       768
Thr Ser Tyr Phe Pro Ser Pro Asp Lys Pro Arg Ile Phe Ala Ser Leu
                245                 250                 255 ggc acc ctg cag gga cat cgt tat ggc ctg ttc agg acc atc gcc aaa       816
Gly Thr Leu Gln Gly His Arg Tyr Gly Leu Phe Arg Thr Ile Ala Lys
```

-continued

```
                      260                 265                 270
gcc tgc gaa gag gtg gat gcg cag tta ctg ttg gca cac tgt ggc ggc       864
Ala Cys Glu Glu Val Asp Ala Gln Leu Leu Leu Ala His Cys Gly Gly
            275                 280                 285 ctc tca gcc acg cag gca ggt gaa ctg gcc cgg ggc ggg gac att cag       912
Leu Ser Ala Thr Gln Ala Gly Glu Leu Ala Arg Gly Gly Asp Ile Gln
        290                 295                 300 gtt gtg gat ttt gcc gat caa tcc gca gca ctt tca cag gca cag ttg       960
Val Val Asp Phe Ala Asp Gln Ser Ala Ala Leu Ser Gln Ala Gln Leu
305                 310                 315                 320 aca atc aca cat ggt ggg atg aat acg gta ctg gac gct att gct tcc      1008
Thr Ile Thr His Gly Gly Met Asn Thr Val Leu Asp Ala Ile Ala Ser
                325                 330                 335 cgc aca ccg cta ctg gcg ctg ccg ctg gca ttt gat caa cct ggc gtg      1056
Arg Thr Pro Leu Leu Ala Leu Pro Leu Ala Phe Asp Gln Pro Gly Val
            340                 345                 350 gca tca cga att gtt tat cat ggc atc ggc aag cgt gcg tct cgg ttt      1104
Ala Ser Arg Ile Val Tyr His Gly Ile Gly Lys Arg Ala Ser Arg Phe
        355                 360                 365 act acc agc cat gcg ctg gcg cgg cag att cga tcg ctg ctg act aac      1152
Thr Thr Ser His Ala Leu Ala Arg Gln Ile Arg Ser Leu Leu Thr Asn
370                 375                 380 acc gat tac ccg cag cgt atg aca aaa att cag gcc gca ttg cgt ctg      1200
Thr Asp Tyr Pro Gln Arg Met Thr Lys Ile Gln Ala Ala Leu Arg Leu
385                 390                 395                 400 gca ggc ggc aca cca gcc gcc gcc gat att gtt gaa cag gcg atg cgg      1248
Ala Gly Gly Thr Pro Ala Ala Ala Asp Ile Val Glu Gln Ala Met Arg
                405                 410                 415 acc tgt cag cca gta ctc agt ggg cag gat tat gca acc gca cta tga      1296
Thr Cys Gln Pro Val Leu Ser Gly Gln Asp Tyr Ala Thr Ala Leu
            420                 425                 430

<210> SEQ ID NO 4
<211> LENGTH: 431
<212> TYPE: PRT
<213> ORGANISM: Pantoea stewartii

<400> SEQUENCE: 4

Met Ser His Phe Ala Val Ile Ala Pro Pro Phe Phe Ser His Val Arg
1               5                   10                  15

Ala Leu Gln Asn Leu Ala Gln Glu Leu Val Ala Arg Gly His Arg Val
            20                  25                  30

Thr Phe Phe Gln Gln His Asp Cys Lys Ala Leu Val Thr Gly Ser Asp
        35                  40                  45

Ile Gly Phe Gln Thr Val Gly Leu Gln Thr His Pro Pro Gly Ser Leu
    50                  55                  60

Ser His Leu Leu His Leu Ala Ala His Pro Leu Gly Pro Ser Met Leu
65                  70                  75                  80

Arg Leu Ile Asn Glu Met Ala Arg Thr Ser Asp Met Leu Cys Arg Glu
                85                  90                  95

Leu Pro Ala Ala Phe His Ala Leu Gln Ile Glu Gly Val Ile Val Asp
            100                 105                 110

Gln Met Glu Pro Ala Gly Ala Val Val Ala Glu Ala Ser Gly Leu Pro
        115                 120                 125

Phe Val Ser Val Ala Cys Ala Leu Pro Leu Asn Arg Glu Pro Gly Leu
    130                 135                 140

Pro Leu Ala Val Met Pro Phe Glu Tyr Gly Thr Ser Asp Ala Ala Arg
145                 150                 155                 160
```

```
Glu Arg Tyr Thr Thr Ser Glu Lys Ile Tyr Asp Trp Leu Met Arg Arg
                165                 170                 175

His Asp Arg Val Ile Ala His Ala Cys Arg Met Gly Leu Ala Pro
            180                 185                 190

Arg Glu Lys Leu His His Cys Phe Ser Pro Leu Ala Gln Ile Ser Gln
        195                 200                 205

Leu Ile Pro Glu Leu Asp Phe Pro Arg Lys Ala Leu Pro Asp Cys Phe
    210                 215                 220

His Ala Val Gly Pro Leu Arg Gln Pro Gln Gly Thr Pro Gly Ser Ser
225                 230                 235                 240

Thr Ser Tyr Phe Pro Ser Pro Asp Lys Pro Arg Ile Phe Ala Ser Leu
            245                 250                 255

Gly Thr Leu Gln Gly His Arg Tyr Gly Leu Phe Arg Thr Ile Ala Lys
        260                 265                 270

Ala Cys Glu Glu Val Asp Ala Gln Leu Leu Ala His Cys Gly Gly
    275                 280                 285

Leu Ser Ala Thr Gln Ala Gly Glu Leu Ala Arg Gly Gly Asp Ile Gln
290                 295                 300

Val Val Asp Phe Ala Asp Gln Ser Ala Ala Leu Ser Gln Ala Gln Leu
305                 310                 315                 320

Thr Ile Thr His Gly Gly Met Asn Thr Val Leu Asp Ala Ile Ala Ser
            325                 330                 335

Arg Thr Pro Leu Leu Ala Leu Pro Leu Ala Phe Asp Gln Pro Gly Val
        340                 345                 350

Ala Ser Arg Ile Val Tyr His Gly Ile Gly Lys Arg Ala Ser Arg Phe
    355                 360                 365

Thr Thr Ser His Ala Leu Ala Arg Gln Ile Arg Ser Leu Leu Thr Asn
    370                 375                 380

Thr Asp Tyr Pro Gln Arg Met Thr Lys Ile Gln Ala Ala Leu Arg Leu
385                 390                 395                 400

Ala Gly Gly Thr Pro Ala Ala Ala Asp Ile Val Glu Gln Ala Met Arg
            405                 410                 415

Thr Cys Gln Pro Val Leu Ser Gly Gln Asp Tyr Ala Thr Ala Leu
        420                 425                 430

<210> SEQ ID NO 5
<211> LENGTH: 1149
<212> TYPE: DNA
<213> ORGANISM: Pantoea stewartii
<220> FEATURE:
<221> NAME/KEY: CDS
<222> LOCATION: (1)..(1149)

<400> SEQUENCE: 5 atg caa ccg cac tat gat ctc att ctg gtc ggt gcc ggt ctg gct aat      48
Met Gln Pro His Tyr Asp Leu Ile Leu Val Gly Ala Gly Leu Ala Asn
1               5                   10                  15 ggc ctt atc gcg ctc cgg ctt cag caa cag cat ccg gat atg cgg atc      96
Gly Leu Ile Ala Leu Arg Leu Gln Gln Gln His Pro Asp Met Arg Ile
            20                  25                  30 ttg ctt att gag gcg ggt cct gag gcg gga ggg aac cat acc tgg tcc     144
Leu Leu Ile Glu Ala Gly Pro Glu Ala Gly Gly Asn His Thr Trp Ser
        35                  40                  45 ttt cac gaa gag gat tta acg ctg aat cag cat cgc tgg ata gcg ccg     192
Phe His Glu Glu Asp Leu Thr Leu Asn Gln His Arg Trp Ile Ala Pro
    50                  55                  60
```

```
ctt gtg gtc cat cac tgg ccc gac tac cag gtt cgt ttc ccc caa cgc      240
Leu Val Val His His Trp Pro Asp Tyr Gln Val Arg Phe Pro Gln Arg
 65              70                  75                  80 cgt cgc cat gtg aac agt ggc tac tac tgc gtg acc tcc cgg cat ttc      288
Arg Arg His Val Asn Ser Gly Tyr Tyr Cys Val Thr Ser Arg His Phe
                 85                  90                  95 gcc ggg ata ctc cgg caa cag ttt gga caa cat tta tgg ctg cat acc      336
Ala Gly Ile Leu Arg Gln Gln Phe Gly Gln His Leu Trp Leu His Thr
            100                 105                 110 gcg gtt tca gcc gtt cat gct gaa tcg gtc cag tta gcg gat ggc cgg      384
Ala Val Ser Ala Val His Ala Glu Ser Val Gln Leu Ala Asp Gly Arg
        115                 120                 125 att att cat gcc agt aca gtg atc gac gga cgg ggt tac acg cct gat      432
Ile Ile His Ala Ser Thr Val Ile Asp Gly Arg Gly Tyr Thr Pro Asp
130                 135                 140 tct gca cta cgc gta gga ttc cag gca ttt atc ggt cag gag tgg caa      480
Ser Ala Leu Arg Val Gly Phe Gln Ala Phe Ile Gly Gln Glu Trp Gln
145                 150                 155                 160 ctg agc gcg ccg cat ggt tta tcg tca ccg att atc atg gat gcg acg      528
Leu Ser Ala Pro His Gly Leu Ser Ser Pro Ile Ile Met Asp Ala Thr
                165                 170                 175 gtc gat cag caa aat ggc tac cgc ttt gtt tat acc ctg ccg ctt tcc      576
Val Asp Gln Gln Asn Gly Tyr Arg Phe Val Tyr Thr Leu Pro Leu Ser
            180                 185                 190 gca acc gca ctg ctg atc gaa gac aca cac tac att gac aag gct aat      624
Ala Thr Ala Leu Leu Ile Glu Asp Thr His Tyr Ile Asp Lys Ala Asn
        195                 200                 205 ctt cag gcc gaa cgg gcg cgt cag aac att cgc gat tat gct gcg cga      672
Leu Gln Ala Glu Arg Ala Arg Gln Asn Ile Arg Asp Tyr Ala Ala Arg
210                 215                 220 cag ggt tgg ccg tta cag acg ttg ctg cgg gaa gaa cag ggt gca ttg      720
Gln Gly Trp Pro Leu Gln Thr Leu Leu Arg Glu Glu Gln Gly Ala Leu
225                 230                 235                 240 ccc att acg tta acg ggc gat aat cgt cag ttt tgg caa cag caa ccg      768
Pro Ile Thr Leu Thr Gly Asp Asn Arg Gln Phe Trp Gln Gln Gln Pro
                245                 250                 255 caa gcc tgt agc gga tta cgc gcc ggg ctg ttt cat ccg aca acc ggc      816
Gln Ala Cys Ser Gly Leu Arg Ala Gly Leu Phe His Pro Thr Thr Gly
            260                 265                 270 tac tcc cta ccg ctc gcg gtg gcg ctg gcc gat cgt ctc agc gcg ctg      864
Tyr Ser Leu Pro Leu Ala Val Ala Leu Ala Asp Arg Leu Ser Ala Leu
        275                 280                 285 gat gtg ttt acc tct tcc tct gtt cac cag acg att gct cac ttt gcc      912
Asp Val Phe Thr Ser Ser Ser Val His Gln Thr Ile Ala His Phe Ala
290                 295                 300 cag caa cgt tgg cag caa cag ggg ttt ttc cgc atg ctg aat cgc atg      960
Gln Gln Arg Trp Gln Gln Gln Gly Phe Phe Arg Met Leu Asn Arg Met
305                 310                 315                 320 ttg ttt tta gcc gga ccg gcc gag tca cgc tgg cgt gtg atg cag cgt     1008
Leu Phe Leu Ala Gly Pro Ala Glu Ser Arg Trp Arg Val Met Gln Arg
                325                 330                 335 ttc tat ggc tta ccc gag gat ttg att gcc cgc ttt tat gcg gga aaa     1056
Phe Tyr Gly Leu Pro Glu Asp Leu Ile Ala Arg Phe Tyr Ala Gly Lys
            340                 345                 350 ctc acc gtg acc gat cgg cta cgc att ctg agc ggc aag ccg ccc gtt     1104
Leu Thr Val Thr Asp Arg Leu Arg Ile Leu Ser Gly Lys Pro Pro Val
        355                 360                 365 ccc gtt ttc gcg gca ttg cag gca att atg acg act cat cgt tga         1149
Pro Val Phe Ala Ala Leu Gln Ala Ile Met Thr Thr His Arg
370                 375                 380
```

<210> SEQ ID NO 6
<211> LENGTH: 382
<212> TYPE: PRT
<213> ORGANISM: Pantoea stewartii

<400> SEQUENCE: 6

```
Met Gln Pro His Tyr Asp Leu Ile Leu Val Gly Ala Gly Leu Ala Asn
1               5                   10                  15

Gly Leu Ile Ala Leu Arg Leu Gln Gln Gln His Pro Asp Met Arg Ile
            20                  25                  30

Leu Leu Ile Glu Ala Gly Pro Glu Ala Gly Asn His Thr Trp Ser
        35                  40                  45

Phe His Glu Glu Asp Leu Thr Leu Asn Gln His Arg Trp Ile Ala Pro
    50                  55                  60

Leu Val Val His His Trp Pro Asp Tyr Gln Val Arg Phe Pro Gln Arg
65                  70                  75                  80

Arg Arg His Val Asn Ser Gly Tyr Tyr Cys Val Thr Ser Arg His Phe
                85                  90                  95

Ala Gly Ile Leu Arg Gln Gln Phe Gly Gln His Leu Trp Leu His Thr
            100                 105                 110

Ala Val Ser Ala Val His Ala Glu Ser Val Gln Leu Ala Asp Gly Arg
        115                 120                 125

Ile Ile His Ala Ser Thr Val Ile Asp Gly Arg Gly Tyr Thr Pro Asp
    130                 135                 140

Ser Ala Leu Arg Val Gly Phe Gln Ala Phe Ile Gly Gln Glu Trp Gln
145                 150                 155                 160

Leu Ser Ala Pro His Gly Leu Ser Ser Pro Ile Ile Met Asp Ala Thr
                165                 170                 175

Val Asp Gln Gln Asn Gly Tyr Arg Phe Val Tyr Thr Leu Pro Leu Ser
            180                 185                 190

Ala Thr Ala Leu Leu Ile Glu Asp Thr His Tyr Ile Asp Lys Ala Asn
        195                 200                 205

Leu Gln Ala Glu Arg Ala Arg Gln Asn Ile Arg Asp Tyr Ala Ala Arg
    210                 215                 220

Gln Gly Trp Pro Leu Gln Thr Leu Leu Arg Glu Glu Gln Gly Ala Leu
225                 230                 235                 240

Pro Ile Thr Leu Thr Gly Asp Asn Arg Gln Phe Trp Gln Gln Pro
                245                 250                 255

Gln Ala Cys Ser Gly Leu Arg Ala Gly Leu Phe His Pro Thr Thr Gly
            260                 265                 270

Tyr Ser Leu Pro Leu Ala Val Ala Leu Ala Asp Arg Leu Ser Ala Leu
        275                 280                 285

Asp Val Phe Thr Ser Ser Val His Gln Thr Ile Ala His Phe Ala
    290                 295                 300

Gln Gln Arg Trp Gln Gln Gly Phe Phe Arg Met Leu Asn Arg Met
305                 310                 315                 320

Leu Phe Leu Ala Gly Pro Ala Glu Ser Arg Trp Arg Val Met Gln Arg
                325                 330                 335

Phe Tyr Gly Leu Pro Glu Asp Leu Ile Ala Arg Phe Tyr Ala Gly Lys
            340                 345                 350

Leu Thr Val Thr Asp Arg Leu Arg Ile Leu Ser Gly Lys Pro Pro Val
        355                 360                 365

Pro Val Phe Ala Ala Leu Gln Ala Ile Met Thr Thr His Arg
```

<210> SEQ ID NO 7
<211> LENGTH: 1479
<212> TYPE: DNA
<213> ORGANISM: Pantoea stewartii
<220> FEATURE:
<221> NAME/KEY: CDS
<222> LOCATION: (1)..(1479)

<400> SEQUENCE: 7

| | | | | | | | | | | | | | | | | |
|---|---|---|---|---|---|---|---|---|---|---|---|---|---|---|---|---|
| atg | aaa | cca | act | acg | gta | att | ggt | gcg | ggc | ttt | ggt | ggc | ctg | gca | ctg | 48 |
| Met | Lys | Pro | Thr | Thr | Val | Ile | Gly | Ala | Gly | Phe | Gly | Gly | Leu | Ala | Leu | |
| 1 | | | | 5 | | | | | 10 | | | | | 15 | | |
| gca | att | cgt | tta | cag | gcc | gca | ggt | att | cct | gtt | ttg | ctg | ctt | gag | cag | 96 |
| Ala | Ile | Arg | Leu | Gln | Ala | Ala | Gly | Ile | Pro | Val | Leu | Leu | Leu | Glu | Gln | |
| | | | 20 | | | | | 25 | | | | | 30 | | | |
| cgc | gac | aag | ccg | ggt | ggc | cgg | gct | tat | gtt | tat | cag | gag | cag | ggc | ttt | 144 |
| Arg | Asp | Lys | Pro | Gly | Gly | Arg | Ala | Tyr | Val | Tyr | Gln | Glu | Gln | Gly | Phe | |
| | | 35 | | | | | 40 | | | | | 45 | | | | |
| act | ttt | gat | gca | ggc | cct | acc | gtt | atc | acc | gat | ccc | agc | gcg | att | gaa | 192 |
| Thr | Phe | Asp | Ala | Gly | Pro | Thr | Val | Ile | Thr | Asp | Pro | Ser | Ala | Ile | Glu | |
| 50 | | | | | 55 | | | | | 60 | | | | | | |
| gaa | ctg | ttt | gct | ctg | gcc | ggt | aaa | cag | ctt | aag | gat | tac | gtc | gag | ctg | 240 |
| Glu | Leu | Phe | Ala | Leu | Ala | Gly | Lys | Gln | Leu | Lys | Asp | Tyr | Val | Glu | Leu | |
| 65 | | | | | 70 | | | | | 75 | | | | | 80 | |
| ttg | ccg | gtc | acg | ccg | ttt | tat | cgc | ctg | tgc | tgg | gag | tcc | ggc | aag | gtc | 288 |
| Leu | Pro | Val | Thr | Pro | Phe | Tyr | Arg | Leu | Cys | Trp | Glu | Ser | Gly | Lys | Val | |
| | | | | 85 | | | | | 90 | | | | | 95 | | |
| ttc | aat | tac | gat | aac | gac | cag | gcc | cag | tta | gaa | gcg | cag | ata | cag | cag | 336 |
| Phe | Asn | Tyr | Asp | Asn | Asp | Gln | Ala | Gln | Leu | Glu | Ala | Gln | Ile | Gln | Gln | |
| | | | 100 | | | | | 105 | | | | | 110 | | | |
| ttt | aat | ccg | cgc | gat | gtt | gcg | ggt | tat | cga | gcg | ttc | ctt | gac | tat | tcg | 384 |
| Phe | Asn | Pro | Arg | Asp | Val | Ala | Gly | Tyr | Arg | Ala | Phe | Leu | Asp | Tyr | Ser | |
| | | 115 | | | | | 120 | | | | | 125 | | | | |
| cgt | gcc | gta | ttc | aat | gag | ggc | tat | ctg | aag | ctc | ggc | act | gtg | cct | ttt | 432 |
| Arg | Ala | Val | Phe | Asn | Glu | Gly | Tyr | Leu | Lys | Leu | Gly | Thr | Val | Pro | Phe | |
| | 130 | | | | | 135 | | | | | 140 | | | | | |
| tta | tcg | ttc | aaa | gac | atg | ctt | cgg | gcc | gcg | ccc | cag | ttg | gca | aag | ctg | 480 |
| Leu | Ser | Phe | Lys | Asp | Met | Leu | Arg | Ala | Ala | Pro | Gln | Leu | Ala | Lys | Leu | |
| 145 | | | | | 150 | | | | | 155 | | | | | 160 | |
| cag | gca | tgg | cgc | agc | gtt | tac | agt | aaa | gtt | gcc | ggc | tac | att | gag | gat | 528 |
| Gln | Ala | Trp | Arg | Ser | Val | Tyr | Ser | Lys | Val | Ala | Gly | Tyr | Ile | Glu | Asp | |
| | | | | 165 | | | | | 170 | | | | | 175 | | |
| gag | cat | ctt | cgg | cag | gcg | ttt | tct | ttt | cac | tcg | ctc | tta | gtg | ggg | ggg | 576 |
| Glu | His | Leu | Arg | Gln | Ala | Phe | Ser | Phe | His | Ser | Leu | Leu | Val | Gly | Gly | |
| | | | 180 | | | | | 185 | | | | | 190 | | | |
| aat | ccg | ttt | gca | acc | tcg | tcc | att | tat | acg | ctg | att | cac | gcg | tta | gaa | 624 |
| Asn | Pro | Phe | Ala | Thr | Ser | Ser | Ile | Tyr | Thr | Leu | Ile | His | Ala | Leu | Glu | |
| | | 195 | | | | | 200 | | | | | 205 | | | | |
| cgg | gaa | tgg | ggc | gtc | tgg | ttt | cca | cgc | ggt | gga | acc | ggt | gcg | ctg | gtc | 672 |
| Arg | Glu | Trp | Gly | Val | Trp | Phe | Pro | Arg | Gly | Gly | Thr | Gly | Ala | Leu | Val | |
| | 210 | | | | | 215 | | | | | 220 | | | | | |
| aat | ggc | atg | atc | aag | ctg | ttt | cag | gat | ctg | ggc | ggc | gaa | gtc | gtg | ctt | 720 |
| Asn | Gly | Met | Ile | Lys | Leu | Phe | Gln | Asp | Leu | Gly | Gly | Glu | Val | Val | Leu | |
| 225 | | | | | 230 | | | | | 235 | | | | | 240 | |
| aac | gcc | cgg | gtc | agt | cat | atg | gaa | acc | gtt | ggg | gac | aag | att | cag | gcc | 768 |
| Asn | Ala | Arg | Val | Ser | His | Met | Glu | Thr | Val | Gly | Asp | Lys | Ile | Gln | Ala | |
| | | | | 245 | | | | | 250 | | | | | 255 | | |
| gtg | cag | ttg | gaa | gac | ggc | aga | cgg | ttt | gaa | acc | tgc | gcg | gtg | gcg | tcg | 816 |
| Val | Gln | Leu | Glu | Asp | Gly | Arg | Arg | Phe | Glu | Thr | Cys | Ala | Val | Ala | Ser | |

```
                260                 265                 270
aac gct gat gtt gta cat acc tat cgc gat ctg ctg tct cag cat ccc    864
Asn Ala Asp Val Val His Thr Tyr Arg Asp Leu Leu Ser Gln His Pro
        275                 280                 285 gca gcc gct aag cag gcg aaa aaa ctg caa tcc aag cgt atg agt aac    912
Ala Ala Ala Lys Gln Ala Lys Lys Leu Gln Ser Lys Arg Met Ser Asn
    290                 295                 300 tca ctg ttt gta ctc tat ttt ggt ctc aac cat cat cac gat caa ctc    960
Ser Leu Phe Val Leu Tyr Phe Gly Leu Asn His His His Asp Gln Leu
305                 310                 315                 320 gcc cat cat acc gtc tgt ttt ggg cca cgc tac cgt gaa ctg att cac   1008
Ala His His Thr Val Cys Phe Gly Pro Arg Tyr Arg Glu Leu Ile His
                325                 330                 335 gaa att ttt aac cat gat ggt ctg gct gag gat ttt tcg ctt tat tta   1056
Glu Ile Phe Asn His Asp Gly Leu Ala Glu Asp Phe Ser Leu Tyr Leu
                    340                 345                 350 cac gca cct tgt gtc acg gat ccg tca ctg gca ccg gaa ggg tgc ggc   1104
His Ala Pro Cys Val Thr Asp Pro Ser Leu Ala Pro Glu Gly Cys Gly
                355                 360                 365 agc tat tat gtg ctg gcg cct gtt cca cac tta ggc acg gca aac ctc   1152
Ser Tyr Tyr Val Leu Ala Pro Val Pro His Leu Gly Thr Ala Asn Leu
    370                 375                 380 gac tgg gcg gta gaa gga ccc cga ctg cgc gat cgt att ttt gac tac   1200
Asp Trp Ala Val Glu Gly Pro Arg Leu Arg Asp Arg Ile Phe Asp Tyr
385                 390                 395                 400 ctt gag caa cat tac atg cct ggc ttg cga agc cag ttg gtg acg cac   1248
Leu Glu Gln His Tyr Met Pro Gly Leu Arg Ser Gln Leu Val Thr His
                405                 410                 415 cgt atg ttt acg ccg ttc gat ttc cgc gac gag ctc aat gcc tgg caa   1296
Arg Met Phe Thr Pro Phe Asp Phe Arg Asp Glu Leu Asn Ala Trp Gln
                    420                 425                 430 ggt tcg gcc ttc tcg gtt gaa cct att ctg acc cag agc gcc tgg ttc   1344
Gly Ser Ala Phe Ser Val Glu Pro Ile Leu Thr Gln Ser Ala Trp Phe
                435                 440                 445 cga cca cat aac cgc gat aag cac att gat aat ctt tat ctg gtt ggc   1392
Arg Pro His Asn Arg Asp Lys His Ile Asp Asn Leu Tyr Leu Val Gly
    450                 455                 460 gca ggc acc cat cct ggc gcg ggc att ccc ggc gta atc ggc tcg gcg   1440
Ala Gly Thr His Pro Gly Ala Gly Ile Pro Gly Val Ile Gly Ser Ala
465                 470                 475                 480 aag gcg acg gca ggc tta atg ctg gag gac ctg att tga               1479
Lys Ala Thr Ala Gly Leu Met Leu Glu Asp Leu Ile
                485                 490

<210> SEQ ID NO 8
<211> LENGTH: 492
<212> TYPE: PRT
<213> ORGANISM: Pantoea stewartii

<400> SEQUENCE: 8

Met Lys Pro Thr Thr Val Ile Gly Ala Gly Phe Gly Gly Leu Ala Leu
1               5                   10                  15

Ala Ile Arg Leu Gln Ala Ala Gly Ile Pro Val Leu Leu Leu Glu Gln
            20                  25                  30

Arg Asp Lys Pro Gly Gly Arg Ala Tyr Val Tyr Gln Glu Gln Gly Phe
        35                  40                  45

Thr Phe Asp Ala Gly Pro Thr Val Ile Thr Asp Pro Ser Ala Ile Glu
    50                  55                  60

Glu Leu Phe Ala Leu Ala Gly Lys Gln Leu Lys Asp Tyr Val Glu Leu
```

-continued

```
                65                  70                  75                  80
Leu Pro Val Thr Pro Phe Tyr Arg Leu Cys Trp Glu Ser Gly Lys Val
                        85                  90                  95
Phe Asn Tyr Asp Asn Asp Gln Ala Gln Leu Glu Ala Gln Ile Gln Gln
                100                 105                 110
Phe Asn Pro Arg Asp Val Ala Gly Tyr Arg Ala Phe Leu Asp Tyr Ser
                115                 120                 125
Arg Ala Val Phe Asn Glu Gly Tyr Leu Lys Leu Gly Thr Val Pro Phe
            130                 135                 140
Leu Ser Phe Lys Asp Met Leu Arg Ala Pro Gln Leu Ala Lys Leu
145                 150                 155                 160
Gln Ala Trp Arg Ser Val Tyr Ser Lys Val Ala Gly Tyr Ile Glu Asp
                165                 170                 175
Glu His Leu Arg Gln Ala Phe Ser Phe His Ser Leu Leu Val Gly Gly
                180                 185                 190
Asn Pro Phe Ala Thr Ser Ser Ile Tyr Thr Leu Ile His Ala Leu Glu
                195                 200                 205
Arg Glu Trp Gly Val Trp Phe Pro Arg Gly Gly Thr Gly Ala Leu Val
            210                 215                 220
Asn Gly Met Ile Lys Leu Phe Gln Asp Leu Gly Gly Glu Val Val Leu
225                 230                 235                 240
Asn Ala Arg Val Ser His Met Glu Thr Val Gly Asp Lys Ile Gln Ala
                245                 250                 255
Val Gln Leu Glu Asp Gly Arg Arg Phe Glu Thr Cys Ala Val Ala Ser
            260                 265                 270
Asn Ala Asp Val Val His Thr Tyr Arg Asp Leu Leu Ser Gln His Pro
            275                 280                 285
Ala Ala Ala Lys Gln Ala Lys Lys Leu Gln Ser Lys Arg Met Ser Asn
            290                 295                 300
Ser Leu Phe Val Leu Tyr Phe Gly Leu Asn His His His Asp Gln Leu
305                 310                 315                 320
Ala His His Thr Val Cys Phe Gly Pro Arg Tyr Arg Glu Leu Ile His
                325                 330                 335
Glu Ile Phe Asn His Asp Gly Leu Ala Glu Asp Phe Ser Leu Tyr Leu
                340                 345                 350
His Ala Pro Cys Val Thr Asp Pro Ser Leu Ala Pro Glu Gly Cys Gly
            355                 360                 365
Ser Tyr Tyr Val Leu Ala Pro Val Pro His Leu Gly Thr Ala Asn Leu
            370                 375                 380
Asp Trp Ala Val Glu Gly Pro Arg Leu Arg Asp Arg Ile Phe Asp Tyr
385                 390                 395                 400
Leu Glu Gln His Tyr Met Pro Gly Leu Arg Ser Gln Leu Val Thr His
                405                 410                 415
Arg Met Phe Thr Pro Phe Asp Phe Arg Asp Glu Leu Asn Ala Trp Gln
                420                 425                 430
Gly Ser Ala Phe Ser Val Glu Pro Ile Leu Thr Gln Ser Ala Trp Phe
            435                 440                 445
Arg Pro His Asn Arg Asp Lys His Ile Asp Asn Leu Tyr Leu Val Gly
            450                 455                 460
Ala Gly Thr His Pro Gly Ala Gly Ile Pro Gly Val Ile Gly Ser Ala
465                 470                 475                 480
Lys Ala Thr Ala Gly Leu Met Leu Glu Asp Leu Ile
                485                 490
```

```
<210> SEQ ID NO 9
<211> LENGTH: 891
<212> TYPE: DNA
<213> ORGANISM: Pantoea stewartii
<220> FEATURE:
<221> NAME/KEY: CDS
<222> LOCATION: (1)..(891)

<400> SEQUENCE: 9 atg gcg gtt ggc tcg aaa agc ttt gcg act gca tcg acg ctt ttc gac        48
Met Ala Val Gly Ser Lys Ser Phe Ala Thr Ala Ser Thr Leu Phe Asp
1               5                   10                  15 gcc aaa acc cgt cgc agc gtg ctg atg ctt tac gca tgg tgc cgc cac        96
Ala Lys Thr Arg Arg Ser Val Leu Met Leu Tyr Ala Trp Cys Arg His
            20                  25                  30 tgc gac gac gtc att gac gat caa aca ctg ggc ttt cat gcc gac cag       144
Cys Asp Asp Val Ile Asp Asp Gln Thr Leu Gly Phe His Ala Asp Gln
        35                  40                  45 ccc tct tcg cag atg cct gag cag cgc ctg cag cag ctt gaa atg aaa       192
Pro Ser Ser Gln Met Pro Glu Gln Arg Leu Gln Gln Leu Glu Met Lys
    50                  55                  60 acg cgt cag gcc tac gcc ggt tcg caa atg cac gag ccc gct ttt gcc       240
Thr Arg Gln Ala Tyr Ala Gly Ser Gln Met His Glu Pro Ala Phe Ala
65                  70                  75                  80 gcg ttt cag gag gtc gcg atg gcg cat gat atc gct ccc gcc tac gcg       288
Ala Phe Gln Glu Val Ala Met Ala His Asp Ile Ala Pro Ala Tyr Ala
                85                  90                  95 ttc gac cat ctg gaa ggt ttt gcc atg gat gtg cgc gaa acg cgc tac       336
Phe Asp His Leu Glu Gly Phe Ala Met Asp Val Arg Glu Thr Arg Tyr
            100                 105                 110 ctg aca ctg gac gat acg ctg cgt tat tgc tat cac gtc gcc ggt gtt       384
Leu Thr Leu Asp Asp Thr Leu Arg Tyr Cys Tyr His Val Ala Gly Val
        115                 120                 125 gtg ggc ctg atg atg gcg caa att atg ggc gtt cgc gat aac gcc acg       432
Val Gly Leu Met Met Ala Gln Ile Met Gly Val Arg Asp Asn Ala Thr
    130                 135                 140 ctc gat cgc gcc tgc gat ctc ggg ctg gct ttc cag ttg acc aac att       480
Leu Asp Arg Ala Cys Asp Leu Gly Leu Ala Phe Gln Leu Thr Asn Ile
145                 150                 155                 160 gcg cgt gat att gtc gac gat gct cag gtg ggc cgc tgt tat ctg cct       528
Ala Arg Asp Ile Val Asp Asp Ala Gln Val Gly Arg Cys Tyr Leu Pro
                165                 170                 175 gaa agc tgg ctg gaa gag gaa gga ctg acg aaa gcg aat tat gct gcg       576
Glu Ser Trp Leu Glu Glu Glu Gly Leu Thr Lys Ala Asn Tyr Ala Ala
            180                 185                 190 cca gaa aac cgg cag gcc tta agc cgt atc gcc ggg cga ctg gta cgg       624
Pro Glu Asn Arg Gln Ala Leu Ser Arg Ile Ala Gly Arg Leu Val Arg
        195                 200                 205 gaa gcg gaa ccc tat tac gta tca tca atg gcc ggt ctg gca caa tta       672
Glu Ala Glu Pro Tyr Tyr Val Ser Ser Met Ala Gly Leu Ala Gln Leu
    210                 215                 220 ccc tta cgc tcg gcc tgg gcc atc gcg aca gcg aag cag gtg tac cgt       720
Pro Leu Arg Ser Ala Trp Ala Ile Ala Thr Ala Lys Gln Val Tyr Arg
225                 230                 235                 240 aaa att ggc gtg aaa gtt gaa cag gcc ggt aag cag gcc tgg gat cat       768
Lys Ile Gly Val Lys Val Glu Gln Ala Gly Lys Gln Ala Trp Asp His
                245                 250                 255 cgc cag tcc acg tcc acc gcc gaa aaa tta acg ctt ttg ctg acg gca       816
Arg Gln Ser Thr Ser Thr Ala Glu Lys Leu Thr Leu Leu Leu Thr Ala
            260                 265                 270
```

```
tcc ggt cag gca gtt act tcc cgg atg aag acg tat cca ccc cgt cct    864
Ser Gly Gln Ala Val Thr Ser Arg Met Lys Thr Tyr Pro Pro Arg Pro
        275                 280                 285 gct cat ctc tgg cag cgc ccg atc tag                                891
Ala His Leu Trp Gln Arg Pro Ile
    290                 295
```

<210> SEQ ID NO 10
<211> LENGTH: 296
<212> TYPE: PRT
<213> ORGANISM: Pantoea stewartii

<400> SEQUENCE: 10

```
Met Ala Val Gly Ser Lys Ser Phe Ala Thr Ala Ser Thr Leu Phe Asp
1               5                   10                  15

Ala Lys Thr Arg Arg Ser Val Leu Met Leu Tyr Ala Trp Cys Arg His
            20                  25                  30

Cys Asp Asp Val Ile Asp Asp Gln Thr Leu Gly Phe His Ala Asp Gln
        35                  40                  45

Pro Ser Ser Gln Met Pro Glu Gln Arg Leu Gln Leu Glu Met Lys
    50                  55                  60

Thr Arg G

<220> FEATURE:
<221> NAME/KEY: CDS
<222> LOCATION: (1)..(528)

<400> SEQUENCE: 11

```
atg ttg tgg att tgg aat gcc ctg atc gtg ttt gtc acc gtg gtc ggc      48
Met Leu Trp Ile Trp Asn Ala Leu Ile Val Phe Val Thr Val Val Gly
1               5                   10                  15 atg gaa gtg gtt gct gca ctg gca cat aaa tac atc atg cac ggc tgg      96
Met Glu Val Val Ala Ala Leu Ala His Lys Tyr Ile Met His Gly Trp
            20                  25                  30 ggt tgg ggc tgg cat ctt tca cat cat gaa ccg cgt aaa ggc gca ttt     144
Gly Trp Gly Trp His Leu Ser His His Glu Pro Arg Lys Gly Ala Phe
        35                  40                  45 gaa gtt aac gat ctc tat gcc gtg gta ttc gcc att gtg tcg att gcc     192
Glu Val Asn Asp Leu Tyr Ala Val Val Phe Ala Ile Val Ser Ile Ala
    50                  55                  60 ctg att tac ttc ggc agt aca gga atc tgg ccg ctc cag tgg att ggt     240
Leu Ile Tyr Phe Gly Ser Thr Gly Ile Trp Pro Leu Gln Trp Ile Gly
65                  70                  75                  80 gca ggc atg acc gct tat ggt tta ctg tat ttt atg gtc cac gac gga     288
Ala Gly Met Thr Ala Tyr Gly Leu Leu Tyr Phe Met Val His Asp Gly
                85                  90                  95 ctg gta cac cag cgc tgg ccg ttc cgc tac ata ccg cgc aaa ggc tac     336
Leu Val His Gln Arg Trp Pro Phe Arg Tyr Ile Pro Arg Lys Gly Tyr
            100                 105                 110 ctg aaa cgg tta tac atg gcc cac cgt atg cat cat gct gta agg gga     384
Leu Lys Arg Leu Tyr Met Ala His Arg Met His His Ala Val Arg Gly
        115                 120                 125 aaa gag ggc tgc gtg tcc ttt ggt ttt ctg tac gcg cca ccg tta tct     432
Lys Glu Gly Cys Val Ser Phe Gly Phe Leu Tyr Ala Pro Pro Leu Ser
    130                 135                 140 aaa ctt cag gcg acg ctg aga gaa agg cat gcg gct aga tcg ggc gct     480
Lys Leu Gln Ala Thr Leu Arg Glu Arg His Ala Ala Arg Ser Gly Ala
145                 150                 155                 160 gcc aga gat gag cag gac ggg gtg gat acg tct tca tcc ggg aag taa     528
Ala Arg Asp Glu Gln Asp Gly Val Asp Thr Ser Ser Ser Gly Lys
                165                 170                 175
```

<210> SEQ ID NO 12
<211> LENGTH: 175
<212> TYPE: PRT
<213> ORGANISM: Pantoea stewartii

<400> SEQUENCE: 12

```
Met Leu Trp Ile Trp Asn Ala Leu Ile Val Phe Val Thr Val Val Gly
1               5                   10                  15

Met Glu Val Val Ala Ala Leu Ala His Lys Tyr Ile Met His Gly Trp
            20                  25                  30

Gly Trp Gly Trp His Leu Ser His His Glu Pro Arg Lys Gly Ala Phe
        35                  40                  45

Glu Val Asn Asp Leu Tyr Ala Val Val Phe Ala Ile Val Ser Ile Ala
    50                  55                  60

Leu Ile Tyr Phe Gly Ser Thr Gly Ile Trp Pro Leu Gln Trp Ile Gly
65                  70                  75                  80

Ala Gly Met Thr Ala Tyr Gly Leu Leu Tyr Phe Met Val His Asp Gly
                85                  90                  95

Leu Val His Gln Arg Trp Pro Phe Arg Tyr Ile Pro Arg Lys Gly Tyr
            100                 105                 110
```

```
Leu Lys Arg Leu Tyr Met Ala His Arg Met His His Ala Val Arg Gly
        115                 120                 125
Lys Glu Gly Cys Val Ser Phe Gly Phe Leu Tyr Ala Pro Pro Leu Ser
    130                 135                 140
Lys Leu Gln Ala Thr Leu Arg Glu Arg His Ala Ala Arg Ser Gly Ala
145                 150                 155                 160
Ala Arg Asp Glu Gln Asp Gly Val Asp Thr Ser Ser Ser Gly Lys
                165                 170                 175

<210> SEQ ID NO 13
<211> LENGTH: 61
<212> TYPE: DNA
<213> ORGANISM: Artificial sequence
<220> FEATURE:
<223> OTHER INFORMATION: Primer 5'kan(dxs)

<400> SEQUENCE: 13
tggaagcgct agcggactac atcatccagc gtaataaata acgtcttgag cgattgtgta      60
g                                                                     61

<210> SEQ ID NO 14
<211> LENGTH: 65
<212> TYPE: DNA
<213> ORGANISM: Artificial sequence
<220> FEATURE:
<223> OTHER INFORMATION: Primer 5'kan(idi)

<400> SEQUENCE: 14
tctgatgcgc aagctgaaga aaaatgagca tggagaataa tatgacgtct tgagcgattg      60
tgtag                                                                 65

<210> SEQ ID NO 15
<211> LENGTH: 65
<212> TYPE: DNA
<213> ORGANISM: Artificial sequence
<220> FEATURE:
<223> OTHER INFORMATION: Primer 5'kan(lytB)

<400> SEQUENCE: 15
tttgatattg aagtgctgga atcgatccg gcactggagg cgtaacgtct tgagcgattg       60
tgtag                                                                 65

<210> SEQ ID NO 16
<211> LENGTH: 65
<212> TYPE: DNA
<213> ORGANISM: Artificial sequence
<220> FEATURE:
<223> OTHER INFORMATION: Primer 5'kan(dxr)

<400> SEQUENCE: 16
gaagcggcgc tggcagacaa agaagcagaa ctgatgcagt tctgacgtct tgagcgattg      60
tgtag                                                                 65

<210> SEQ ID NO 17
<211> LENGTH: 65
<212> TYPE: DNA
<213> ORGANISM: Artificial sequence
<220> FEATURE:
<223> OTHER INFORMATION: Primer 5'kan(ygbBP)

<400> SEQUENCE: 17
gacgcgtcga agcgcgcaca gtctgcgggg caaaacaatc gataacgtct tgagcgattg      60
``` tgtag                                                                65

<210> SEQ ID NO 18
<211> LENGTH: 64
<212> TYPE: DNA
<213> ORGANISM: Artificial sequence
<220> FEATURE:
<223> OTHER INFORMATION: Primer 3'kan

<400> SEQUENCE: 18
gaagacgaaa gggcctcgtg atacgcctat ttttataggt tatatgaata tcctccttag   60
ttcc                                                                 64

<210> SEQ ID NO 19
<211> LENGTH: 50
<212> TYPE: DNA
<213> ORGANISM: Artificial sequence
<220> FEATURE:
<223> OTHER INFORMATION: Primer 5'-T5

<400> SEQUENCE: 19
ctaaggagga tattcatata acctataaaa ataggcgtat cacgaggccc                50

<210> SEQ ID NO 20
<211> LENGTH: 70
<212> TYPE: DNA
<213> ORGANISM: Artificial sequence
<220> FEATURE:
<223> OTHER INFORMATION: Primer 3'-T5(dxs)

<400> SEQUENCE: 20
ggagtcgacc agtgccaggg tcgggtattt ggcaatatca aaactcatag ttaatttctc   60
ctctttaatg                                                           70

<210> SEQ ID NO 21
<211> LENGTH: 68
<212> TYPE: DNA
<213> ORGANISM: Artificial sequence
<220> FEATURE:
<223> OTHER INFORMATION: Primer 3'-T5(idi)

<400> SEQUENCE: 21
tgggaactcc ctgtgcattc aataaaatga cgtgttccgt ttgcatagtt aatttctcct   60
ctttaatg                                                             68

<210> SEQ ID NO 22
<211> LENGTH: 68
<212> TYPE: DNA
<213> ORGANISM: Artificial sequence
<220> FEATURE:
<223> OTHER INFORMATION: Primer 3'-T5(lytB)

<400> SEQUENCE: 22
ctaccccggc acaaaaacca cgtgggttgg ccaacaggat ctgcatagtt aatttctcct   60
ctttaatg                                                             68

<210> SEQ ID NO 23
<211> LENGTH: 68
<212> TYPE: DNA
<213> ORGANISM: Artificial sequence
<220> FEATURE:
<223> OTHER INFORMATION: Primer 3'-T5(dxr)

-continued

```
<400> SEQUENCE: 23
tgcaaccaat cgagccggtc gagcccagaa tggtgagttg cttcatagtt aatttctcct      60
ctttaatg                                                              68

<210> SEQ ID NO 24
<211> LENGTH: 68
<212> TYPE: DNA
<213> ORGANISM: Artificial sequence
<220> FEATURE:
<223> OTHER INFORMATION: Primer 3'-T5(ygbBP)

<400> SEQUENCE: 24
cggccgccgg aaccacggcg caaacatcca aatgagtggt tgccatagtt aatttctcct     60
ctttaatg                                                              68

<210> SEQ ID NO 25
<211> LENGTH: 65
<212> TYPE: DNA
<213> ORGANISM: Artificial sequence
<220> FEATURE:
<223> OTHER INFORMATION: Primer 5'-kanT5(ispA)

<400> SEQUENCE: 25
aacgaagacg cctctctaac ccctttttaca ccggacaatg agtaacgtct tgagcgattg    60
tgtag                                                                 65

<210> SEQ ID NO 26
<211> LENGTH: 65
<212> TYPE: DNA
<213> ORGANISM: Artificial sequence
<220> FEATURE:
<223> OTHER INFORMATION: Primer 5'-kanT5(ychB)

<400> SEQUENCE: 26
ggtcaacgca tcaagttaaa aatggataac tggatagtga ataacgtct tgagcgattg      60 tgtag                                                                 65

<210> SEQ ID NO 27
<211> LENGTH: 65
<212> TYPE: DNA
<213> ORGANISM: Artificial sequence
<220> FEATURE:
<223> OTHER INFORMATION: Primer 5'-kanT5(gcpE)

<400> SEQUENCE: 27
gttgcgcgtc tgaccctcaa tgccgaacaa tcaccggcgc agtaacgtct tgagcgattg     60
tgtag                                                                 65

<210> SEQ ID NO 28
<211> LENGTH: 65
<212> TYPE: DNA
<213> ORGANISM: Artificial sequence
<220> FEATURE:
<223> OTHER INFORMATION: Primer 5'-kanT5(ispB)

<400> SEQUENCE: 28
accataaacc ctaagttgcc tttgttcaca gtaaggtaat cggggcgtct tgagcgattg     60
tgtag                                                                 65

<210> SEQ ID NO 29
<211> LENGTH: 70
```

```
<212> TYPE: DNA
<213> ORGANISM: Artificial sequence
<220> FEATURE:
<223> OTHER INFORMATION: Primer 3'-kanT5(ispA)

<400> SEQUENCE: 29
ctggttggcc tgcttaacgc aggcttcgag ttgctgcgga aagtccatag ttaatttctc    60
ctctttaatg                                                           70

<210> SEQ ID NO 30
<211> LENGTH: 68
<212> TYPE: DNA
<213> ORGANISM: Artificial sequence
<220> FEATURE:
<223> OTHER INFORMATION: Primer 3'-kanT5(ychB)

<400> SEQUENCE: 30
ataaaaacag attaagtttt gccggagagg gccactgtgt ccgcatagtt aatttctcct    60
ctttaatg                                                             68

<210> SEQ ID NO 31
<211> LENGTH: 68
<212> TYPE: DNA
<213> ORGANISM: Artificial sequence
<220> FEATURE:
<223> OTHER INFORMATION: Primer 3'-kanT5(gcpE)

<400> SEQUENCE: 31
aaatacgtgt tgattttcta cgttgaattg gagcctggtt atgcatagtt aatttctcct    60
ctttaatg                                                             68

<210> SEQ ID NO 32
<211> LENGTH: 67
<212> TYPE: DNA
<213> ORGANISM: Artificial sequence
<220> FEATURE:
<223> OTHER INFORMATION: Primer 3'-kanT5(ispB)

<400> SEQUENCE: 32
cgccatatct tgcgcggtta actcattgat tttttctaaa ttcatagtta atttctcctc    60
tttaatg                                                              67

<210> SEQ ID NO 33
<211> LENGTH: 25
<212> TYPE: DNA
<213> ORGANISM: Artificial sequence
<220> FEATURE:
<223> OTHER INFORMATION: Forward primer for crt gene cluster

<400> SEQUENCE: 33
atgacggtct gcgcaaaaaa acacg                                          25

<210> SEQ ID NO 34
<211> LENGTH: 28
<212> TYPE: DNA
<213> ORGANISM: Artificial sequence
<220> FEATURE:
<223> OTHER INFORMATION: Reverse primer for crt gene cluster

<400> SEQUENCE: 34
gagaaattat gttgtggatt tggaatgc                                       28

<210> SEQ ID NO 35
```

<211> LENGTH: 25
<212> TYPE: DNA
<213> ORGANISM: Artificial sequence
<220> FEATURE:
<223> OTHER INFORMATION: Primer T-kan

<400> SEQUENCE: 35
accggatatc accacttatc tgctc                                    25

<210> SEQ ID NO 36
<211> LENGTH: 26
<212> TYPE: DNA
<213> ORGANISM: Artificial sequence
<220> FEATURE:
<223> OTHER INFORMATION: Primer B-dxs

<400> SEQUENCE: 36
tggcaacagt cgtagctcct gggtgg                                   26

<210> SEQ ID NO 37
<211> LENGTH: 32
<212> TYPE: DNA
<213> ORGANISM: Artificial sequence
<220> FEATURE:
<223> OTHER INFORMATION: Primer T-T5

<400> SEQUENCE: 37
taacctataa aataggcgt atcacgaggc cc                             32

<210> SEQ ID NO 38
<211> LENGTH: 25
<212> TYPE: DNA
<213> ORGANISM: Artificial sequence
<220> FEATURE:
<223> OTHER INFORMATION: Primer B-idi

<400> SEQUENCE: 38
tcatgctgac ctggtgaagg aatcc                                    25

<210> SEQ ID NO 39
<211> LENGTH: 45
<212> TYPE: DNA
<213> ORGANISM: Artificial sequence
<220> FEATURE:
<223> OTHER INFORMATION: Primer B-ispB

<400> SEQUENCE: 39
accataaacc ctaagttgcc tttgttcaca gtaaggtaat cgggg              45

<210> SEQ ID NO 40
<211> LENGTH: 8609
<212> TYPE: DNA
<213> ORGANISM: Artificial sequence
<220> FEATURE:
<223> OTHER INFORMATION: Plasmid pPCB15

<400> SEQUENCE: 40
cgtatggcaa tgaaagacgg tgagctggtg atatgggata gtgttcaccc ttgttacacc    60
gttttccatg agcaaactga aacgttttca tcgctctgga gtgaatacca cgacgatttc   120
cggcagtttc tacacatata ttcgcaagat gtggcgtgtt acggtgaaaa cctggcctat   180
ttccctaaag ggtttattga gaatatgttt ttcgtctcag ccaatccctg ggtgagtttc   240
accagttttg atttaaacgt ggccaatatg gacaacttct tcgccccgt tttcaccatg    300 ggcaaatatt atacgcaagg cgacaaggtg ctgatgccgc tggcgattca ggttcatcat   360

-continued

```
gccgtctgtg atggcttcca tgtcggcaga atgcttaatg aattacaaca gtactgcgat    420
gagtggcagg gcgggcgta atttttttaa ggcagttatt ggtgcctaga aatattttat    480
ctgattaata agatgatctt cttgagatcg ttttggtctg cgcgtaatct cttgctctga    540
aaacgaaaaa accgccttgc agggcggttt ttcgaaggtt ctctgagcta ccaactcttt    600
gaaccgaggt aactggcttg gaggagcgca gtcaccaaaa cttgtccttt cagtttagcc    660
ttaaccggcg catgacttca agactaactc ctctaaatca attaccagtg gctgctgcca    720
gtggtgcttt tgcatgtctt tccgggttgg actcaagacg atagttaccg gataaggcgc    780
agcggtcgga ctgaacgggg ggttcgtgca tacagtccag cttggagcga actgcctacc    840
cggaactgag tgtcaggcgt ggaatgagac aaacgcggcc ataacagcgg aatgacaccg    900
gtaaaccgaa aggcaggaac aggagagcgc acgagggagc cgccagggga aacgcctggt    960
atctttatag tcctgtcggg tttcgccacc actgatttga gcgtcagatt tcgtgatgct   1020
tgtcaggggg gcggagccta tggaaaaacg gctttgccgc ggccctctca cttccctgtt   1080
aagtatcttc ctggcatctt ccaggaaatc tccgccccgt tcgtaagcca tttccgctcg   1140
ccgcagtcga acgaccgagc gtagcgagtc agtgagcgag gaagcggaat atatcctgta   1200
tcacatattc tgctgacgca ccggtgcagc ctttttctc ctgccacatg aagcacttca   1260
ctgacaccct catcagtgcc aacatagtaa gccagtatat acactccgct agcgcccaat   1320
acgcaaaccg cctctccccg cgcgttggcc gattcattaa tgcagctggc acgacaggtt   1380
tcccgactgg aaagcgggca gtgagcgcaa cgcaattaat gtgagttagc tcactcatta   1440
ggcaccccag gctttacact ttatgcttcc ggctcgtatg ttgtgtggaa ttgtgagcgg   1500
ataacaattt cacacaggaa acagctatga ccatgattac gaattcgagc tcggtaccca   1560
aacgaattcg ccctttttgac ggtctgcgca aaaaaacacg ttcaccttac tggcatttcg   1620
gctgagcagt tgctggctga tatcgatagc cgccttgatc agttactgcc ggttcagggt   1680
gagcgggatt gtgtgggtgc cgcgatgcgt gaaggcacgc tggcaccggg caaacgtatt   1740
cgtccgatgc tgctgttatt aacagcgcgc gatcttggct gtgcgatcag tcacggggga   1800
ttactggatt tagcctgcgc ggttgaaatg gtgcatgctg cctcgctgat tctggatgat   1860
atgccctgca tggacgatgc gcagatgcgt cgggggcgtc ccaccattca cacgcagtac   1920
ggtgaacatg tggcgattct ggcggcggtc gctttactca gcaaagcgtt tggggtgatt   1980
gccgaggctg aaggtctgac gccgatagcc aaaactcgcg cggtgtcgga gctgtccact   2040
gcgattggca tgcagggtct ggttcagggc cagtttaagg acctctcgga aggcgataaa   2100
ccccgcagcg ccgatgccat actgctaacc aatcagttta aaaccagcac gctgttttgc   2160
gcgtcaacgc aaatggcgtc cattgcggcc aacgcgtcct gcgaagcgcg tgagaacctg   2220
catcgttcct cgctcgatct cggccaggcc tttcagttgc ttgacgatct taccgatggc   2280
atgaccgata ccggcaaaga catcaatcag gatgcaggta aatcaacgct ggtcaattta   2340
ttaggctcag gcgcggtcga agaacgcctg cgacagcatt tgcgcctggc cagtgaacac   2400
ctttccgcgg catgccaaaa cggccattcc accacccaac tttttattca ggcctggttt   2460
gacaaaaaac tcgctgccgt cagttaagga tgctgcatga ccatttttgc ggtgatcgca   2520 ccgcccttt tcagccatgt tcgcgctctg caaaaccttg ctcaggaatt agtggcccgc   2580
ggtcatcgtg ttacgttttt tcagcaacat gactgcaaag cgctggtaac gggcagcgat   2640
atcggattcc agaccgtcgg actgcaaacg catcctcccg gttccttatc gcacctgctg   2700
```

```
cacctggccg cgcacccact cggaccctcg atgttacgac tgatcaatga aatggcacgt    2760
accagcgata tgctttgccg ggaactgccc gccgcttttc atgcgttgca gatagagggc    2820
gtgatcgttg atcaaatgga gccggcaggt gcagtagtcg cagaagcgtc aggtctgccg    2880
tttgtttcgg tggcctgcgc gctgccgctc aaccgcgaac cgggtttgcc tctggcggtg    2940
atgcctttcg agtacggcac cagcgatgcg gctcggaac gctataccac cagcgaaaaa     3000
atttatgact ggctgatgcg acgtcacgat cgtgtgatcg cgcatcatgc atgcagaatg    3060
ggtttagccc cgcgtgaaaa actgcatcat tgttttctc cactggcaca aatcagccag     3120
ttgatccccg aactggattt tccccgcaaa gcgctgccag actgctttca tgcggttgga    3180
ccgttacggc aacccaggg gacgccgggg tcatcaactt cttattttcc gtccccggac      3240
aaacccgta tttttgcctc gctgggcacc ctgcaggaca tcgttatgg cctgttcagg       3300
accatcgcca aagcctgcga agaggtggat gcgcagttac tgttggcaca ctgtggcggc    3360
ctctcagcca cgcaggcagg tgaactggcc cggggcgggg acattcaggt tgtggatttt    3420
gccgatcaat ccgcagcact ttcacaggca cagttgacaa tcacacatgg tgggatgaat   3480
acggtactgg acgctattgc ttcccgcaca ccgctactgg cgctgccgct ggcatttgat    3540
caacctggcg tggcatcacg aattgtttat catggcatcg gcaagcgtgc gtctcggttt    3600
actaccagcc atgcgctggc gcggcagatt cgatcgctgc tgactaacac cgattacccg    3660
cagcgtatga caaaaattca ggccgcattg cgtctggcag cggcacacc agccgccgcc     3720
gatattgttg aacaggcgat gcggacctgt cagccagtac tcagtgggca ggattatgca    3780
accgcactat gatctcattc tggtcggtgc cggtctggct aatggcctta tcgcgctccg    3840
gcttcagcaa cagcatccgg atatgcggat cttgcttatt gaggcgggtc ctgaggcggg    3900
agggaaccat acctggtcct ttcacgaaga ggatttaacg ctgaatcagc atcgctggat    3960
agcgccgctt gtggtccatc actgcccga ctaccaggtt cgtttccccc aacgccgtcg     4020
ccatgtgaac agtggctact actgcgtgac ctcccggcat ttcgccggga tactccggca   4080
acagtttgga caacatttat ggctgcatac cgcggtttca gccgttcatg ctgaatcggt    4140
ccagttagcg gatggccgga ttattcatgc cagtacagtg atcgacggac ggggttacac    4200
gcctgattct gcactacgcg taggattcca ggcatttatc ggtcaggagt ggcaactgag    4260
cgcgccgcat ggtttatcgt caccgattat catggatgcg acggtcgatc agcaaaatgg    4320
ctaccgcttt gttatacccc tgccgctttc cgcaaccgca ctgctgatcg aagacacaca    4380
ctacattgac aaggctaatc ttcaggccga acgggcgcgt cagaacattc gcgattatgc    4440
tgcgcgacag ggttggccgt tacagacgtt gctgcgggaa gaacagggtg cattgcccat    4500
tacgttaacg ggcgataatc gtcagttttg gcaaacagcaa ccgcaagcct gtagcggatt    4560
acgcgccggg ctgtttcatc cgacaaccgg ctactcccta ccgctcgcgg tggcgctggc    4620
cgatcgtctc agcgcgctgg atgtgtttac ctcttcctct gttcaccaga cgattgctca    4680
ctttgcccag caacgttggc agcaacaggg gttttccgc atgctgaatc gcatgttgtt     4740
tttagccgga ccgccgagt cacgctggcg tgtgatgcag cgtttctatg gcttacccga    4800
ggatttgatt gcccgctttt atgcgggaaa actcaccgtg accgatcggc tacgcattct    4860
gagcggcaag ccgcccgttc ccgttttcgc ggcattgcag gcaattatga cgactcatcg    4920
ttgaagagcg actacatgaa accaactacg gtaattggtg cgggctttgg tggcctggca    4980
ctggcaattc gttacaggc cgcaggtatt cctgttttgc tgcttgagca gcgcgacaag    5040
ccgggtggcc gggcttatgt ttatcaggag cagggcttta cttttgatgc aggccctacc    5100
```

```
gttatcaccg atcccagcgc gattgaagaa ctgtttgctc tggccggtaa acagcttaag    5160
gattacgtcg agctgttgcc ggtcacgccg ttttatcgcc tgtgctggga gtccggcaag    5220
gtcttcaatt acgataacga ccaggcccag ttagaagcgc agatacagca gtttaatccg    5280
cgcgatgttg cgggttatcg agcgttcctt gactattcgc gtgccgtatt caatgagggc    5340
tatctgaagc tcggcactgt gccttttta tcgttcaaag acatgcttcg ggccgcgccc      5400
cagttggcaa agctgcaggc atggcgcagc gtttacagta agttgccgg ctacattgag      5460 gatgagcatc ttcggcaggc gttttctttt cactcgctct tagtgggggg gaatccgttt    5520
gcaacctcgt ccatttatac gctgattcac gcgttagaac gggaatgggg cgtctggttt    5580
ccacgcggtg gaaccggtgc gctggtcaat ggcatgatca agctgtttca ggatctgggc    5640
ggcgaagtcg tgcttaacgc ccgggtcagt catatggaaa ccgttgggga caagattcag    5700
gccgtgcagt tggaagacgg cagacggttt gaaacctgcg cggtggcgtc gaacgctgat    5760
gttgtacata cctatcgcga tctgctgtct cagcatcccg cagccgctaa gcaggcgaaa    5820
aaactgcaat ccaagcgtat gagtaactca ctgtttgtac tctattttgg tctcaaccat    5880
catcacgatc aactcgccca tcataccgtc tgttttgggc cacgctaccg tgaactgatt    5940
cacgaaattt ttaaccatga tggtctggct gaggattttt cgctttattt acacgcacct    6000
tgtgtcacgg atccgtcact ggcaccggaa gggtgcggca gctattatgt gctggcgcct    6060
gttccacact taggcacggc gaacctcgac tgggcggtag aaggaccccg actgcgcgat    6120
cgtatttttg actaccttga gcaacattac atgcctggct tgcgaagcca gttggtgacg    6180
caccgtatgt ttacgccgtt cgatttccgc gacgagctca atgcctggca aggttcggcc    6240
ttctcggttg aacctattct gacccagagc gcctggttcc gaccacataa ccgcgataag    6300
cacattgata atctttatct ggttggcgca ggcacccatc ctggcgcggg cattcccggc    6360
gtaatcggct cggcgaaggc gacggcaggc ttaatgctgg aggacctgat ttgacgaata    6420
cgtcattact gaatcatgcc gtcgaaacca tggcggttgg ctcgaaaagc tttgcgactg    6480
catcgacgct tttcgacgcc aaaacccgtc gcagcgtgct gatgctttac gcatggtgcc    6540
gccactgcga cgacgtcatt gacgatcaaa cactgggctt tcatgccgac cagccctctt    6600
cgcagatgcc tgagcagcgc ctgcagcagc ttgaaatgaa aacgcgtcag gcctacgccg    6660
gttcgcaaat gcacgagccc gcttttgccg cgtttcagga ggtcgcgatg gcgcatgata    6720
tcgctcccgc ctacgcgttc gaccatctgg aaggttttgc catggatgtg cgcgaaacgc    6780
gctacctgac actggacgat acgctgcgtt attgctatca cgtcgccggt gttgtgggcc    6840
tgatgatggc gcaaattatg ggcgttcgcg ataacgccac gctcgatcgc gcctgcgatc    6900
tcgggctggc tttccagttg accaacattg cgcgtgatat tgtcgacgat gctcaggtgg    6960
gccgctgtta tctgcctgaa agctggctgg aagaggaagg actgacgaaa gcgaattatg    7020
ctgcgccaga aaaccggcag gccttaagcc gtatcgccgg gcgactggta cgggaagcgg    7080
aaccctatta cgtatcatca atggccggtc tggcacaatt acccttacgc tcggcctggg    7140
ccatcgcgac agcgaagcag gtgtaccgta aaattggcgt gaagttgaa caggccggta      7200 agcaggcctg ggatcatcgc cagtccacgt ccaccgccga aaaattaacg cttttgctga    7260
cggcatccgg tcaggcagtt acttcccgga tgaagacgta tccacccgt cctgctcatc       7320 tctggcagcg cccgatctag ccgcatgcct ttctctcagc gtcgcctgaa gtttagataa    7380
cggtggcgcg tacagaaaac caaaggacac gcagccctct tttcccctta cagcatgatg    7440
```

-continued

```
catacggtgg gccatgtata accgtttcag gtagcctttg cgcggtatgt agcggaacgg    7500
ccagcgctgg tgtaccagtc cgtcgtggac cataaaatac agtaaaccat aagcggtcat    7560
gcctgcacca atccactgga gcggccagat tcctgtactg ccgaagtaaa tcagggcaat    7620
cgacacaatg gcgaatacca cggcatagag atcgttaact tcaaatgcgc ctttacgcgg    7680
ttcatgatgt gaaagatgcc agccccaacc ccagccgtgc atgatgtatt tatgtgccag    7740
tgcagcaacc acttccatgc cgaccacggt gacaaacacg atcagggcat tccaaatcca    7800
caacataatt tctcaagggc gaattcgcgg ggatcctcta gagtcgacct gcaggcatgc    7860
aagcttggca ctggccgtcg ttttacaacg tcgtgactgg gaaaaccctg gcgttaccca    7920
acttaatcgc cttgcagcac atccccettt cgccagctgg cgtaatagcg aagaggcccg    7980
caccgatcgc ccttcccaac agttgcgcag cctgaatggc gaatggcgct gatgtccggc    8040
ggtgcttttg ccgttacgca ccaccccgtc agtagctgaa caggagggac agctgataga    8100
aacagaagcc actggagcac ctcaaaaaca ccatcataca ctaaatcagt aagttggcag    8160
catcacccga cgcactttgc gccgaataaa tacctgtgac ggaagatcac ttcgcagaat    8220
aaataaatcc tggtgtccct gttgataccg ggaagccctg ggccaacttt tggcgaaaat    8280
gagacgttga tcggcacgta agaggttcca actttcacca taatgaaata agatcactac    8340
cgggcgtatt ttttgagtta tcgagatttt caggagctaa ggaagctaaa atggagaaaa    8400
aaatcactgg atataccacc gttgatatat cccaatggca tcgtaaagaa catttgagg    8460 catttcagtc agttgctcaa tgtacctata accagaccgt tcagctggat attacggcct    8520
ttttaaagac cgtaaagaaa aataagcaca gtttttatcc ggcctttatt cacattcttg    8580
cccgcctgat gaatgctcat ccggaattt                                      8609
```

<210> SEQ ID NO 41
<211> LENGTH: 6329
<212> TYPE: DNA
<213> ORGANISM: Artificial sequence
<220> FEATURE:
<223> OTHER INFORMATION: Plasmid pKD46

<400> SEQUENCE: 41

```
catcgattta ttatgacaac ttgacggcta catcattcac ttttcttca caaccggcac     60 ggaactcgct cgggctggcc ccggtgcatt ttttaaatac ccgcgagaaa tagagttgat    120
cgtcaaaacc aacattgcga ccgacggtgg cgataggcat ccgggtggtg ctcaaaagca    180
gcttcgcctg gctgatacgt tggtcctcgc gccagcttaa gacgctaatc cctaactgct    240
ggcggaaaag atgtgacaga cgcgacggcg acaagcaaac atgctgtgcg acgctggcga    300
tatcaaaatt gctgtctgcc aggtgatcgc tgatgtactg acaagcctcg cgtacccgat    360
tatccatcgg tggatggagc gactcgttaa tcgcttccat cgcccgcagt aacaattgct    420
caagcagatt tatcgccagc agctccgaat agcgcccttc ccttgcccg gcgttaatga    480 tttgcccaaa caggtcgctg aaatgcggct ggtgcgcttc atccgggcga agaaccccg    540 tattggcaaa tattgacggc cagttaagcc attcatgcca gtaggcgcgc ggacgaaagt    600
aaacccactg gtgataccat tcgcgagcct ccggatgacg accgtagtga tgaatctctc    660
ctggcgggaa cagcaaaata tcacccgtc ggcaaacaaa ttctcgtccc tgatttttca    720
ccaccccctg accgcgaatg gtgagattga gaatataacc tttcattccc agcggtcggt    780
cgataaaaaa atcgagataa ccgttggcct caatcggcgt taaacccgcc accagatggg    840
cattaaacga gtatcccggc agcagggat cattttgcgc ttcagccata cttttcatac    900
```

-continued

```
tcccgccatt cagagaagaa accaattgtc catattgcat cagacattgc cgtcactgcg      960
tcttttactg gctcttctcg ctaaccaaac cggtaacccc gcttattaaa agcattctgt     1020
aacaaagcgg gaccaaagcc atgacaaaaa cgcgtaacaa aagtgtctat aatcacggca     1080
gaaaagtcca cattgattat ttgcacggcg tcacactttg ctatgccata gcattttat      1140
ccataagatt agcggatcct acctgacgct ttttatcgca actctctact gtttctccat     1200
acccgttttt ttgggaattc gagctctaag gaggttataa aaatggata ttaatactga      1260
aactgagatc aagcaaaagc attcactaac cccctttcct gttttcctaa tcagcccggc     1320
atttcgcggg cgatattttc acagctattt caggagttca gccatgaacg cttattacat     1380
tcaggatcgt cttgaggctc agagctgggc gcgtcactac cagcagctcg cccgtgaaga     1440
gaaagaggca gaactggcag acgacatgga aaaaggcctg ccccagcacc tgtttgaatc     1500
gctatgcatc gatcatttgc aacgccacgg ggccagcaaa aaatccatta cccgtgcgtt     1560
tgatgacgat gttgagtttc aggagcgcat ggcagaacac atccggtaca tggttgaaac     1620
cattgctcac caccaggttg atattgattc agaggtataa aacgaatgag tactgcactc     1680
gcaacgctgg ctgggaagct ggctgaacgt gtcggcatgg attctgtcga cccacaggaa     1740
ctgatcacca ctcttcgcca gacggcattt aaaggtgatg ccagcgatgc gcagttcatc     1800
gcattactga tcgttgccaa ccagtacggc cttaatccgt ggacgaaaga aatttacgcc     1860
tttcctgata agcagaatgg catcgttccg gtggtgggcg ttgatggctg gtccgcatc      1920
atcaatgaaa accagcagtt tgatggcatg gactttgagc aggacaatga atcctgtaca     1980
tgccggattt accgcaagga ccgtaatcat ccgatctgcg ttaccgaatg gatggatgaa     2040
tgccgccgcg aaccattcaa aactcgcgaa ggcagagaaa tcacgggcc gtggcagtcg      2100
catcccaaac ggatgttacg tcataaagcc atgattcagt gtgcccgtct ggccttcgga     2160
tttgctggta tctatgacaa ggatgaagcc gagcgcattg tcgaaaatac tgcatacact     2220
gcagaacgtc agccggaacg cgacatcact ccggttaacg atgaaaccat gcaggagatt     2280
aacactctgc tgatcgccct ggataaaaca tgggatgacg acttattgcc gctctgttcc     2340
cagatatttc gccgcgacat tcgtgcatcg tcagaactga cacaggccga agcagtaaaa     2400
gctcttggat tcctgaaaca gaaagccgca gagcagaagg tggcagcatg acaccggaca     2460
ttatcctgca gcgtaccggg atcgatgtga gagctgtcga acagggggat gatgcgtggc     2520
acaaattacg gctcggcgtc atcaccgctt cagaagttca aacgtgata gcaaaacccc      2580
gctccggaaa gaagtggcct gacatgaaaa tgtcctactt ccacaccctg cttgctgagg     2640
tttgcaccgg tgtggctccg gaagttaacg ctaaagcact ggcctgggga aaacagtacg     2700
agaacgacgc cagaaccctg tttgaattca cttccggcgt gaatgttact gaatccccga     2760
tcatctatcg cgacgaaagt atgcgtaccg cctgctctcc cgatggttta tgcagtgacg     2820
gcaacggcct tgaactgaaa tgcccgttta cctcccggga tttcatgaag ttccggctcg     2880
gtggtttcga ggccataaag tcagcttaca tggcccaggt gcagtacagc atgtgggtga     2940
cgcgaaaaaa tgcctggtac tttgccaact atgacccgcg tatgaagcgt gaaggcctgc     3000
attatgtcgt gattgagcgg gatgaaaagt acatggcgag ttttgacgag atcgtgccgg     3060
agttcatcga aaaatggac gaggcactgg ctgaaattgg ttttgtattt ggggagcaat      3120
ggcgatgacg catcctcacg ataatatccg ggtaggcgca atcactttcg tctactccgt     3180
tacaaagcga ggctgggtat ttcccggcct ttctgttatc cgaaatccac tgaaagcaca     3240
```

-continued

```
gcggctggct gaggagataa ataataaacg aggggctgta tgcacaaagc atcttctgtt    3300
gagttaagaa cgagtatcga gatggcacat agccttgctc aaattggaat caggtttgtg    3360
ccaataccag tagaaacaga cgaagaatcc atgggtatgg acagttttcc ctttgatatg    3420
taacggtgaa cagttgttct acttttgttt gttagtcttg atgcttcact gatagataca    3480
agagccataa gaacctcaga tccttccgta tttagccagt atgttctcta gtgtggttcg    3540 ttgttttgc gtgagccatg agaacgaacc attgagatca tacttacttt gcatgtcact    3600
caaaaatttt gcctcaaaac tggtgagctg aattttgca gttaaagcat cgtgtagtgt    3660
ttttcttagt ccgttacgta ggtaggaatc tgatgtaatg gttgttggta ttttgtcacc    3720
attcattttt atctggttgt tctcaagttc ggttacgaga tccatttgtc tatctagttc    3780
aacttggaaa atcaacgtat cagtcgggcg gcctcgctta tcaaccacca atttcatatt    3840
gctgtaagtg tttaaatctt tacttattgg tttcaaaacc cattggttaa gccttttaaa    3900
ctcatggtag ttattttcaa gcattaacat gaacttaaat tcatcaaggc taatctctat    3960
atttgccttg tgagttttct tttgtgttag ttcttttaat aaccactcat aaatcctcat    4020
agagtatttg ttttcaaaag acttaacatg ttccagatta tattttatga atttttttaa    4080
ctggaaaaga taaggcaata tctcttcact aaaaactaat tctaattttt cgcttgagaa    4140
cttggcatag tttgtccact ggaaaatctc aaagccttta accaaggat tcctgatttc    4200 cacagttctc gtcatcagct ctctggttgc tttagctaat acaccataag cattttccct    4260
actgatgttc atcatctgag cgtattggtt ataagtgaac gataccgtcc gttcttttcct    4320 tgtagggttt tcaatcgtgg ggttgagtag tgccacacag cataaaatta gcttggtttc    4380
atgctccgtt aagtcatagc gactaatcgc tagttcattt gctttgaaaa caactaattc    4440
agacatacat ctcaattggt ctaggtgatt ttaatcacta taccaattga gatgggctag    4500
tcaatgataa ttactagtcc tttttccttttg agttgtgggt atctgtaaat tctgctagac    4560 cttttgctgga aaacttgtaa attctgctag accctctgta aattccgcta gacctttgtg    4620
tgtttttttt gtttatattc aagtggttat aatttataga ataagaaag aataaaaaaa    4680 gataaaaaga atagatccca gccctgtgta taactcacta ctttagtcag ttccgcagta    4740
ttacaaaagg atgtcgcaaa cgctgtttgc tcctctacaa aacagacctt aaaacccctaa    4800 aggcttaagt agcaccctcg caagctcggt tgcggccgca atcgggcaaa tcgctgaata    4860
ttccttttgt ctccgaccat caggcacctg agtcgctgtc ttttttcgtga cattcagttc    4920 gctgcgctca cggctctggc agtgaatggg ggtaaatggc actacaggcg ccttttatgg    4980
attcatgcaa ggaaactacc cataatacaa gaaaagcccg tcacgggctt ctcagggcgt    5040
tttatggcgg gtctgctatg tggtgctatc tgactttttg ctgttcagca gttcctgccc    5100
tctgattttc cagtctgacc acttcggatt atcccgtgac aggtcattca gactggctaa    5160
tgcacccagt aaggcagcgg tatcatcaac ggggtctgac gctcagtgga acgaaaactc    5220
acgttaaggg attttggtca tgagattatc aaaaaggatc ttcacctaga tccttttaaa    5280
ttaaaaatga agttttaaat caatctaaag tatatatgag taaacttggt ctgacagtta    5340
ccaatgctta atcagtgagg cacctatctc agcgatctgt ctatttcgtt catccatagt    5400
tgcctgactc cccgtcgtgt agataactac gatacgggag ggcttaccat ctggccccag    5460
tgctgcaatg ataccgcgag acccacgctc accggctcca gatttatcag caataaacca    5520
gccagccgga agggccgagc gcagaagtgg tcctgcaact ttatccgcct ccatccagtc    5580
tattaattgt tgccgggaag ctagagtaag tagttcgcca gttaatagtt tgcgcaacgt    5640
```

-continued

```
tgttgccatt gctacaggca tcgtggtgtc acgctcgtcg tttggtatgg cttcattcag      5700
ctccggttcc caacgatcaa ggcgagttac atgatccccc atgttgtgca aaaaagcggt      5760
tagctccttc ggtcctccga tcgttgtcag aagtaagttg ccgcagtgt tatcactcat       5820 ggttatggca gcactgcata attctcttac tgtcatgcca tccgtaagat gcttttctgt      5880
gactggtgag tactcaacca agtcattctg agaatagtgt atgcggcgac cgagttgctc      5940
ttgcccggcg tcaatacggg ataataccgc gccacatagc agaactttaa aagtgctcat      6000
cattggaaaa cgttcttcgg ggcgaaaact ctcaaggatc ttaccgctgt tgagatccag      6060
ttcgatgtaa cccactcgtg cacccaactg atcttcagca tcttttactt tcaccagcgt      6120
ttctgggtga gcaaaaacag gaaggcaaaa tgccgcaaaa aagggaataa gggcgacacg      6180
gaaatgttga atactcatac tcttcctttt tcaatattat tgaagcattt atcagggtta      6240
ttgtctcatg agcggataca tatttgaatg tatttagaaa aataaacaaa tagggggttcc      6300 gcgcacattt ccccgaaaag tgccacctg                                         6329
```

<210> SEQ ID NO 42
<211> LENGTH: 3423
<212> TYPE: DNA
<213> ORGANISM: Artificial sequence
<220> FEATURE:
<223> OTHER INFORMATION: Plasmid pSUH5

<400> SEQUENCE: 42

```
agattgcagc attacacgtc ttgagcgatt gtgtaggctg gagctgcttc gaagttccta        60
tactttctag agaataggaa cttcggaata ggaacttcaa gatcccctca cgctgccgca       120
agcactcagg gcgcaagggc tgctaaagga agcggaacac gtagaaagcc agtccgcaga       180
aacggtgctg accccggatg aatgtcagct actgggctat ctggacaagg gaaaacgcaa       240
gcgcaaagag aaagcaggta gcttgcagtg ggcttacatg gcgatagcta gactgggcgg       300
ttttatggac agcaagcgaa ccggaattgc cagctggggc gccctctggt aaggttggga       360
agccctgcaa agtaaactgg atggctttct tgccgccaag gatctgatgg cgcaggggat       420
caagatctga tcaagagaca ggatgaggat cgtttcgcat gattgaacaa gatggattgc       480
acgcaggttc tccggccgct tgggtggaga ggctattcgg ctatgactgg gcacaacaga       540
caatcggctg ctctgatgcc gccgtgttcc ggctgtcagc gcagggcgc ccggttcttt        600 ttgtcaagac cgacctgtcc ggtgccctga atgaactgca ggacgaggca gcgcggctat       660
cgtggctggc cacgacgggc gttccttgcg cagctgtgct cgacgttgtc actgaagcgg       720
gaagggactg gctgctattg ggcgaagtgc cggggcagga tctcctgtca tctcaccttg       780
ctcctgccga gaaagtatcc atcatggctg atgcaatgcg gcggctgcat acgcttgatc       840
cggctacctg cccattcgac caccaagcga aacatcgcat cgagcgagca cgtactcgga       900
tggaagccgg tcttgtcgat caggatgatc tggacgaaga gcatcagggg ctcgcgccag       960
ccgaactgtt cgccaggctc aaggcgcgca tgcccgacgg cgaggatctc gtcgtgaccc      1020
atggcgatgc ctgcttgccg aatatcatgg tggaaaatgg ccgcttttct ggattcatcg      1080
actgtggccg gctgggtgtg gcggaccgct atcaggacat agcgttggct acccgtgata      1140
ttgctgaaga gcttggcggc gaatgggctg accgcttcct cgtgctttac ggtatcgccg      1200
ctcccgattc gcagcgcatc gccttctatc gccttcttga cgagttcttc tgagcgggac      1260
tctggggttc gaaatgaccg accaagcgac gcccaacctg ccatcacgag atttcgattc      1320
```

```
caccgccgcc ttctatgaaa ggttgggctt cggaatcgtt ttccgggacg ccggctggat      1380
gatcctccag cgcggggatc tcatgctgga gttcttcgcc cacccagct tcaaaagcgc       1440 tctgaagttc ctatactttc tagagaatag gaacttcgga ataggaacta aggaggatat      1500
tcactataaa aataggcgta tcacgaggcc ctttcgtctt cacctcgaga atcataaaa       1560 aatttatttg ctttgtgagc ggataacaat tataatagat tcaattgtga gcggataaca      1620
atttcacaca gaattcatta agaggagaa attaactcat atggaccatg gctaattccc       1680
atgtcagccg ttaagtgttc ctgtgtcact gaaaattgct ttgagaggct ctaagggctt      1740
ctcagtgcgt tacatccctg gcttgttgtc cacaaccgtt aaaccttaaa agctttaaaa      1800
gccttatata ttcttttttt tcttataaaa cttaaaacct tagaggctat ttaagttgct      1860
gatttatatt aattttattg ttcaaacatg agagcttagt acgtgaaaca tgagagctta      1920
gtacgttagc catgagagct tagtacgtta gccatgaggg tttagttcgt taaacatgag      1980
agcttagtac gttaaacatg agagcttagt acgtgaaaca tgagagctta gtacgtacta      2040
tcaacaggtt gaactgcgga tcttgcggcc gcaaaaatta aaatgaagt tttaaatcaa       2100 tctaaagtat atatgagtaa acttggtctg acagttacca atgcttaatc agtgaggcac      2160
ctatctcagc gatctgtcta tttcgttcat ccatagttgc ctgactcccc gtcgtgtaga      2220
taactacgat acgggagggc ttaccatctg gccccagtgc tgcaatgata ccgcgagacc      2280
cacgctcacc ggctccagat ttatcagcaa taaaccagcc agccggaagg gccgagcgca      2340
gaagtggtcc tgcaacttta tccgcctcca tccagtctat taattgttgc cgggaagcta      2400
gagtaagtag ttcgccagtt aatagtttgc gcaacgttgt tgccattgct acaggcatcg      2460
tggtgtcacg ctcgtcgttt ggtatggctt cattcagctc cggttcccaa cgatcaaggc      2520
gagttacatg atcccccatg ttgtgcaaaa aagcggttag ctccttcggt cctccgatcg      2580
ttgtcagaag taagttggcc gcagtgttat cactcatggt tatggcagca ctgcataatt      2640
ctcttactgt catgccatcc gtaagatgct tttctgtgac tggtgagtac tcaaccaagt      2700
cattctgaga atagtgtatg cggcgaccga gttgctcttg cccggcgtca atacgggata      2760
ataccgcgcc acatagcaga actttaaaag tgctcatcat tggaaaacgt tcttcggggc      2820
gaaaactctc aaggatctta ccgctgttga gatccagttc gatgtaaccc actcgtgcac      2880
ccaactgatc ttcagcatct tttactttca ccagcgtttc tgggtgagca aaaacaggaa      2940
ggcaaaatgc cgcaaaaaag ggaataaggg cgacacggaa atgttgaata ctcatactct      3000
tcctttttca atattattga agcatttatc agggttattg tctcatgagc ggatacatat      3060
ttgaatgtat ttagaaaaat aaacaaatag gggttccgcg cacatttccc cgaaaagtgc      3120
cacctgcatc gatggccccc cgatggtagt gtgggtctc cccatgcgag agtagggaac       3180
tgccaggcat caaataaaac gaaaggctca gtcgaaagac tgggcctttc gttttatctg      3240
ttgtttgtcg gtgaacgctc tcctgagtag gacaaatccg ccgggagcgg atttgaacgt      3300
tgcgaagcaa cggcccggag ggtggcgggc aggacgcccg ccataaactg ccaggcatca      3360
aattaagcag aaggccatcc tgacggatgg ccttttttgcg tggccagtgc caagcttgca      3420
tgc                                                                    3423
```

<210> SEQ ID NO 43
<211> LENGTH: 156
<212> TYPE: DNA
<213> ORGANISM: Artificial sequence
<220> FEATURE:
<223> OTHER INFORMATION: Promoter PT5

```
<400> SEQUENCE: 43
ctataaaaat aggcgtatca cgaggcccctt tcgtcttcac ctcgagaaat cataaaaaat      60
ttatttgctt tgtgagcgga taacaattat aatagattca attgtgagcg gataacaatt     120
tcacacagaa ttcattaaag aggagaaatt aactca                               156
```